US011850410B2

(12) United States Patent
Daily et al.

(10) Patent No.: US 11,850,410 B2
(45) Date of Patent: Dec. 26, 2023

(54) AUTOMATICALLY RETRACTING SAFETY NEEDLE ASSEMBLY

(71) Applicant: Dali Medical Devices Ltd., Yavne (IL)

(72) Inventors: David Daily, Herzliya (IL); Lior Raday, Kibbutz Bror-Hail (IL); Gad Lewkonya, Neve Mivtach (IL); Ehoud Carmel, Yehud-Monosson (IL); Elyasaf Laybovitch, Nehalim (IL); Dmitri Sarkorov, Rosh HaAyin (IL); Nir Benarous, Holon (IL); Guy Keenan, Tel Aviv (IL)

(73) Assignee: DALI MEDICAL DEVICES LTD, Yavne (IL)

( * ) Notice: Subject to any disclaimer, the term of this patent is extended or adjusted under 35 U.S.C. 154(b) by 0 days.

(21) Appl. No.: 17/189,685

(22) Filed: Mar. 2, 2021

(65) Prior Publication Data

US 2022/0323691 A1    Oct. 13, 2022

Related U.S. Application Data

(60) Provisional application No. 63/093,309, filed on Oct. 19, 2020.

(30) Foreign Application Priority Data

May 3, 2020 (IL) .......................................... 273097

(51) Int. Cl.
*A61M 5/32* (2006.01)
(52) U.S. Cl.
CPC .......... *A61M 5/326* (2013.01); *A61M 5/3234* (2013.01); *A61M 2005/3261* (2013.01); *A61M 2005/3267* (2013.01)

(58) Field of Classification Search
CPC ...... A61M 5/326; A61M 5/3234; A61M 5/28; A61M 2005/3264; A61M 2005/3261
See application file for complete search history.

(56) References Cited

U.S. PATENT DOCUMENTS 8,337,467 B2 * 12/2012 Rimlinger ............. A61M 5/326
604/263
9,186,462 B2 * 11/2015 Lanzi ................... A61M 5/3135
(Continued)

FOREIGN PATENT DOCUMENTS

WO    WO2019158538 A1    8/2019

*Primary Examiner* — Laura A Bouchelle
(74) *Attorney, Agent, or Firm* — Naomi S. Rosenman-Helfand

(57) ABSTRACT

An automatically retracting safety needle assembly configured to receive a syringe. The assembly has distal and proximal ends, and comprises:
a housing, with internal housing (IH), and a base wall.
A moving sleeve (MOS): at least partially within the IH; having a flange wall; axially movable.
A biasing element (BE), within the IH, biasing the MOS proximally.
A syringe, receiving a plunger rod; movable axially within the IH, and coupled to the MOS.
An activation fork (AF), partially disposed within the IH. AF has a guiding arm coupled with the IH and the MOS; preventing motion of the MOS during non-deployment state.
An automatic retraction mechanism, retracting the syringe after injection.
Deployment: advance plunger rod and the AF axially (distally), until AF guiding arm allows proximal movement of the MOS, retracting the syringe. Distal advancement of plunger rod is constant without an abrupt increase in resistive force; allowing safe disposal.

20 Claims, 43 Drawing Sheets

(56) References Cited

U.S. PATENT DOCUMENTS 9,220,848 B2 * 12/2015 Chevallier ............ A61M 5/326
2019/0125978 A1 5/2019 Daily et al.

* cited by examiner

AUTOMATICALLY RETRACTING SAFETY NEEDLE ASSEMBLY

FIELD OF THE INVENTION

The present invention generally relates to hypodermic needles and syringes, and particularly to safety needle assemblies for safe disposal of hypodermic needles after use.

BACKGROUND OF THE INVENTION

A hypodermic needle fitted to a syringe is used for administering injections, such as to inject a medication or drug into a body. The injection is implemented by piercing skin tissue with the needle at a selected body region and then manually depressing a plunger attached to the needle, which forces out the injectant substance through the needle aperture. The needle may be reusable or disposable. For disposable or single use needles, the syringe (and/or the overall assembly encompassing the syringe and the needle) may include safety features to prevent needle reuse, in order to preclude contamination and to prevent potential injury from the exposed needle. Needle reuse can result in the transmission of infectious diseases, especially blood-borne viruses (BBVs), such as for example: the Human Immunodeficiency Virus (HIV) which leads to Acquired Immune Deficiency Syndrome (AIDS); the hepatitis B virus (HBV); and the hepatitis C virus (HCV). The needle/syringe safety features may include a needle guard or sheath to cover the needle when not in use, and a retraction mechanism to retract the needle inside a chamber after completion of the injection. The retraction may be implemented manually, requiring a special action by the user, or implemented automatically via a built-in mechanism configured to automatically retract the needle after use, such as a spring-based retraction mechanism. In a manual or "actively" implemented retractable syringe, the user must actively perform a particular step, such as manually pulling a sheath or needle guard to cover the potentially contaminated needle after use. An automatically implemented retraction may be "fully automated" or "passive", requiring no user action to activate the retraction mechanism. Alternatively, an automatically implemented retraction may be "partially automated" which still requires a certain action by the user. For example, the user may encounter a mechanical resistance when depressing the syringe plunger in a partially automated retractable syringe, such as due to the activation of the retraction mechanism, and must actively apply an additional force in order to activate the mechanism. An automated retraction mechanism may be configured to be activated only after the injection process has been completed. For example, there may be some type of retraction restraint which is only released when the injection is fully executed.

Many conventional syringes include some form of indication to the user (e.g., a medical clinician administering the injection with the syringe) to signify that the injection has been successfully executed. For example, the syringe may provide a visual and/or audible indication, such as via a designated sound such as a "click", to signify completion of the injection. In syringes configured with automated retraction mechanisms, the designated indication may be provided by the mechanism and may also signify the release of the retraction mechanism restraint. Accordingly, when the user depresses the syringe plunger and hears the designated indication sound, he/she is aware that the substance has been fully injected from the needle, and also that the retraction restraint has been released to enable subsequent activation of the needle retraction. However, a user (especially an inexperienced user) may not always fully depress the plunger as a result of the additional resistance (i.e., in addition to the substance injection resistance) caused by the retraction mechanism activation, making it difficult to push the plunger fully all the way. The user may incorrectly perceive the resistance as signifying that the injection was carried out, even though the plunger was not actually fully depressed and no indication was provided. In such a case, the injectant substance may not be expelled fully (or even partially) into the body, and the retraction restraint would not be released thereby preventing the subsequent activation of the automated needle retraction, leading to possible contamination and needlestick injury from the still extended and used needle.

Various safety needle assembly configurations are known in the art. Some examples include: U.S. Pat. No. 6,030,366 to Mitchell, entitled: "Syringe guard system for a unit dose syringe"; U.S. Pat. No. 6,613,022 to Doyle, entitled: "Passive needle guard for syringes"; U.S. Pat. No. 7,255,689 to Westbye, entitled: "Syringe with anti-rotation for luer lock"; U.S. Pat. No. 8,328,765 to Daily et al., entitled: "Automatic needle device"; U.S. Pat. No. 9,044,378 to Verespej et al., entitled: "Anti-needle stick safety device or system for use with drugs requiring reconstitution"; U.S. Pat. No. 9,345,831 to Raday et al., entitled: "Automatic injection device"; U.S. Pat. No. 9,526,846 to Dowds et al., entitled: "Patient-contact activated needle stick safety device"; U.S. Pat. No. 9,616,173 to Slate et al., entitled: "System and method for an injection using a syringe needle"; U.S. Pat. No. 9,642,971 to Newman et al., entitled: "Safety needle assembly"; and U.S. Pat. No. 9,844,634 to Lewkonya et al., entitled: "Automatic needle apparatus".

SUMMARY OF THE INVENTION

In accordance with one aspect of the present invention, there is thus provided an automatically retracting safety needle assembly. The assembly has a distal end and a proximal end. The assembly includes a housing, which includes an internal housing (IH), which includes an inner tube concentric with an outer tube, and a base wall situated at the distal end of the IH. The assembly further includes a moving sleeve (MOS), disposed within the IH. The MOS includes a flange wall, at the proximal end thereof, and the MOS is axially movable. The assembly further includes a biasing element (BE), disposed within the IH. The BE is supported at its distal end by the base wall of the IH and is supported at its proximal end by the flange wall of the MOS. The BE biases the MOS to the proximal direction. The assembly further includes a syringe, disposed in and movable axially within the inner tube of the IH, and coupled to the MOS. The syringe includes: a syringe chamber, containing an injectant substance; a plunger rod, slidably advanceable within the syringe chamber; a plunger stopper, disposed on the distal end of the plunger rod; and a needle, extending from a distal end of the syringe. The assembly further includes an activation fork (AF), disposed within the IH. The AF includes an end member at a proximal end thereof, and at least one guiding arm extending distally from the end member and aligned axially. The guiding arm is coupled with the IH and the MOS so as to prevent proximal motion of the MOS when the assembly is in a non-deployment state. The assembly further includes a retraction mechanism, configured to automatically retract the needle upon completion of injection. The assembly is configured to be deployed for injection by inserting the needle into an injection site, and advancing the plunger rod and the AF axially in the distal direction with respect to the IH, urging the plunger stopper to advance distally within the syringe chamber to expel the injectant substance therefrom through the needle, the plunger rod advancing until the guiding arm of the AF allows movement of the MOS, where the distal advancement of the plunger rod is substantially constant without an abrupt increase in resistive force to overcome for activating the retraction mechanism, allowing for safe disposal of the needle assembly with the needle retracted within the housing. The assembly may further include an indicator, configured to provide an indication of completion of the injection. The assembly may further include a removable needle guard, configured to cover the distal end of the needle when the needle assembly is in the non-deployment state, and to be removed before the injection. The housing may further include an external housing, where the internal housing is fixedly coupled to the external housing at the proximal end thereof. The movable sleeve (MOS) may be a rotating sleeve (ROS), which includes at least one extending arm, extending distally from the flange wall. The ROS further includes a guiding slot on the extending arm, the guiding slot including: a helical-shaped slot portion at the proximal edge of the guiding slot; an elongated straight slot portion distal of the helical-shaped slot portion; and an extension slot portion extending from the straight slot portion. The ROS further includes at least one notched flange, protruding radially outwards from the flange wall, the notched flange including a wide notch. The ROS further includes at least one holding snap, projecting proximally from the edge of the flange wall. The inner tube of the IH may further include at least one direction protrusion positioned inside the guiding slot. The guiding arm of the AF may be coupled with the IH and the ROS by insertion into guiding ribs of the outer tube of the IH, and by insertion into the wide notch of the notched flange of the ROS. The syringe may be coupled to the ROS via the holding snap of the ROS, preventing axial motion of the syringe flange relative to the ROS when the assembly is in the non-deployment state. The flange wall of the ROS may include at least one arc-shaped opening, and the inner tube of the IH may further includes at least one orienting protrusion, configured to prevent rotation of the syringe, where the orienting protrusion is positioned through the arc-shaped opening of the flange wall of the ROS. After the needle is inserted into the injection site, the plunger may advance until the guiding arms of the AF passes through the wide notch of the notched flange of the ROS, allowing for rotation of the ROS inside the end member of the AF, and allowing the biasing force of the BE to move the ROS in the proximal direction, resulting in the directing protrusion urging rotation of the ROS, until the directing protrusion is guided from the helical slot into the straight slot of the guiding slot of the ROS, allowing for further axial movement of the ROS in the proximal direction. The inner tube of the IH may further include at least one locking snap, where further axial movement of the ROS in the proximal direction causes the locking snap of the IH to engage the distal end of the guiding slot and to bend radially to allow continuation of the ROS axial movement, with reciprocal axial movement of the syringe so as to proximally retract the syringe chamber with the needle into the housing, until the distal end of the guiding slot engages the directing protrusion of the IH, and the distal end of the extended arm of the ROS is positioned between the locking snap and the directing protrusion of the IH, such that the directing protrusion prevents further proximal axial movement of the ROS and the syringe, and the locking snap prevents further distal axial movement of the ROS and the syringe, while the alignment of the guiding arm of the AF relative to the notched flange of the ROS prevents detachment of the AF. The movable sleeve (MOS) may be a locking sleeve (LOS), which includes at least one extending arm, extending distally from the flange wall. The LOS further includes a respective gripping snap, disposed on the extending arm, the gripping snap including an extending protrusion with a radially facing slope at the distal end thereof. The LOS further includes at least one holding snap, projecting proximally from the edge of the flange wall. The AF may further include an activation opening, disposed on the guiding arm, where the the guiding arm of the AF is positioned between the gripping snap of the LOS and the IH, such that the guiding arm prevents the gripping snap from deflecting radially, and prevents proximal movement of the LOS, when the assembly is in a non-deployment position. The LOS may further include a respective locking snap, disposed on the extending arm, the locking snap including an extending protrusion with a deflecting slope at the distal end thereof. The LOS may further include at least one LOS stopping protrusion, extending distally from the flange wall. The AF may further include a locking opening, disposed on the guiding arm of the AF. The IH may further include at least one IH stopping protrusion, extending radially inwards from the proximal inner portion of the outer tube. The gripping snap and the locking snap may be a single unified snap, and the activation opening and the locking opening may be a single unified opening. After the needle is inserted into the injection site, the plunger rod may be advanced until the activation opening of the guiding arm of the AF aligns with the gripping snap of the LOS, causing the gripping snap to deflect radially through the activation opening, allowing for proximal movement of the LOS due to the biasing force of the BE, with reciprocal axial movement of the syringe so as to proximally retract the syringe chamber with the needle into the housing, until the gripping snap passes the proximal end of the IH and returns to a non-deflected position. After the needle is inserted into the injection site, the plunger rod may be advanced until the locking opening of the guiding arm of the AF aligns with the locking snap of the LOS, causing the locking snap to deflect radially through the locking opening, during proximal movement of the LOS due to the biasing force of the BE, with reciprocal axial movement of the syringe so as to proximally retract the syringe chamber with the needle into the housing, until the locking snap passes the proximal end of the IH and returns to a non-deflected position, and the LOS stopping protrusion engages the IH stopping protrusion preventing further proximal movement of the LOS, and the locking snap restricts further distal movement of the LOS. The LOS may further include: a first locking window, disposed on the extending arm, distally of the gripping snap, a second locking window, disposed on the extending arm, distally of the first locking window, and at least one LOS stopping protrusion, disposed at the distal end of the extending arm, where the IH further includes at least one IH locking snap, disposed on a distally extending portion of the inner tube of the IH, the IH locking snap including a locking tooth at a proximal end thereof, where the LOS stopping protrusion is aligned angularly with the IH locking snap, and where the locking tooth of the IH locking snap is positioned within the first locking window, when the assembly is in a non-deployment position. The assembly may further include a removable needle guard, configured to cover the distal end of the needle when the assembly is in the non-deployment state, where the needle guard includes a proximal ring and a distal ring, radially encircling the outer circumferential surface of the needle guard, the diameter of the distal ring being smaller than the diameter of the proximal ring, and the assembly may further include an outer cap, positioned at the distal end of an external housing (EH) of the housing, the IH fixedly coupled to the EH at the proximal end thereof, the outer cap including: a cap body, a cap tube, proximal to the cap body, a connecting wall, separating the cap body from the cap tube, and at least one cap snap, disposed within the cap body and inclined radially inward, where the distal end of the cap snap is positioned proximal of the distal ring of the needle guard and the inner portion of the connecting wall is positioned distal of the proximal ring of the needle guard, such that the distal end of the cap snap engages with the distal ring so as to distally pull the needle guard with the outer cap upon distal pulling of the outer cap. The outer cap may further include at least one thick rib and at least one thin rib, extending longitudinally on the outer circumferential surface of the cap tube, the thick rib positioned orthogonal to the thin rib, where the outer cap is configured to cover the needle guard, where the cap tube is positioned within an EH distal tube of the EH and the cap body is positioned distally of a distal opening of the EH, and where the thick ribs and the thin ribs are correspondingly positioned within respective thick slots and thin slots on the EH distal tube, so as to orient the outer cap in relation to the EH. During proximal movement of the LOS due to the biasing force of the BE, with reciprocal axial movement of the syringe so as to proximally retract the syringe chamber with the needle into the housing, the stopping protrusion of the LOS may engage the distal end of the IH preventing further proximal movement of the LOS, and the locking snap of the IH may be aligned such that the locking tooth is positioned within the second locking window of the LOS, causing the locking snap to return to a non-deflected position, and the proximal end of the locking tooth may engage the proximal end of the second locking window, preventing further distal movement of the LOS and the syringe.

In accordance with another aspect of the present invention, there is thus provided a method for automatically retracting a safety needle assembly. The method includes the procedure of providing an automatically retracting safety needle assembly, the assembly having a distal end and a proximal end, the assembly including a housing, which includes an internal housing (IH), which includes an inner tube concentric with an outer tube, and a base wall situated at the distal end of the IH, the assembly further including a moving sleeve (MOS), disposed within the outer tube of the IH, the MOS including a flange wall, at the proximal end thereof, the MOS axially movable, the assembly further including a biasing element (BE), disposed within the IH, the BE supported at its distal end by the base wall of the IH and supported at its proximal end by the flange wall of the MOS, the BE biasing the MOS to the proximal direction, the assembly further including a syringe, disposed in and movable axially within the inner tube of the IH, and coupled to the MOS, the syringe including: a syringe chamber, containing an injectant substance; a plunger rod, slidably advanceable within the syringe chamber; a plunger stopper, disposed on the distal end of the plunger rod; and a needle, extending from a distal end of the syringe, the assembly further including an activation fork (AF), disposed within the IH, the AF including an end member at a proximal end thereof, and at least one guiding arm extending distally from the end member and aligned axially, the guiding arm coupled with the IH and the MOS so as to prevent proximal motion of the MOS when the assembly is in a non-deployment state, the assembly further including a retraction mechanism, configured to automatically retract the needle upon completion of injection. The method further includes the procedure of inserting the needle into an injection site. The method further includes the procedure of advancing the plunger rod and the AF axially in the distal direction with respect to the IH, urging the plunger stopper to advance distally within the syringe chamber to expel the injectant substance therefrom through the needle, the plunger rod advancing until the guiding arm of the AF allows movement of the MOS, where the distal advancement of the plunger rod is substantially constant without an abrupt increase in resistive force to overcome for activating the retraction mechanism, allowing for safe disposal of the needle assembly with the needle retracted within the housing. The method may further include the procedure of providing an indication of completion of the injection using an indicator of the assembly. The movable sleeve (MOS) may be a rotating sleeve (ROS), which includes at least one extending arm, extending distally from the flange wall, the ROS further including a guiding slot on the extending arm, the guiding slot including: a helical-shaped slot portion at the proximal edge of the guiding slot; an elongated straight slot portion distal of the helical-shaped slot portion; and an extension slot portion extending from the straight slot portion, the ROS further including at least one notched flange, protruding radially outwards from the flange wall, the notched flange including a wide notch, the ROS further including at least one holding snap, projecting proximally from the edge of the flange wall, where the inner tube of the IH further includes at least one direction protrusion positioned inside the guiding slot, and where the guiding arm of the AF is coupled with the IH and the ROS by insertion into guiding ribs of the outer tube of the IH, and by insertion into the wide notch of the notched flange of the ROS. The method may further include the procedure of releasing the pressing force upon completion of the injection, to allow the biasing force of the BE to move the ROS in the proximal direction, resulting in the directing protrusion of the IH urging the rotation of the ROS, until the directing protrusion is guided from the helical slot into the straight slot of the guiding slot of the ROS, allowing for further axial movement of the ROS in the proximal direction. The inner tube of the IH may further include at least one locking snap, where the further axial movement of the ROS in the proximal direction causes the locking snap of the IH to engage the distal end of the guiding slot and to bend radially to allow continuation of the ROS axial movement, with reciprocal axial movement of the syringe so as to proximally retract the syringe chamber with the needle into the housing, until the distal end of the guiding slot engages the directing protrusion of the IH, and the distal end of the extended arm of the ROS is positioned between the locking snap and the directing protrusion of the IH, such that the directing protrusion prevents further proximal axial movement of the ROS and the syringe, and the locking snap prevents further distal axial movement of the OS and the syringe, while the alignment of the guiding arm of the AF relative to the notched flange of the ROS prevents detachment of the AF. The movable sleeve (MOS) may be a locking sleeve (LOS), which includes at least one extending arm, extending distally from the flange wall, the LOS further including a respective gripping snap, disposed on the extending arm, the gripping snap including an extending protrusion with a radially facing slope at the distal end thereof, the LOS further including at least one holding snap, projecting proximally from the edge of the flange wall, where the AF further includes an activation opening, disposed on the guiding arm, and where the the guiding arm of the AF is positioned between the gripping snap of the LOS and the IH, such that the guiding arm prevents the gripping snap from deflecting radially, and prevents proximal movement of the LOS, when the assembly is in a non-deployment position. The LOS may further include a respective locking snap, disposed on the extending arm, the locking snap including an extending protrusion with a deflecting slope at the distal end thereof, the LOS further including at least one LOS stopping protrusion, extending distally from the flange wall, where the AF further includes a locking opening, disposed on the guiding arm of the AF, and where the IH further includes at least one IH stopping protrusion, extending radially inwards from the proximal inner portion of the outer tube. The method may further include the procedure of distally advancing the plunger rod and the AF, after the needle is inserted into the injection site, until the activation opening of the guiding arm of the AF aligns with the gripping snap of the LOS, causing the gripping snap to deflect radially through the activation opening, allowing for proximal movement of the LOS due to the biasing force of the BE, with reciprocal axial movement of the syringe so as to proximally retract the syringe chamber with the needle into the housing, until the gripping snap passes the proximal end of the IH and returns to a non-deflected position. The method may further include the procedure of distally advancing the plunger rod and the AF, after the needle is inserted into the injection site, until the locking opening of the guiding arm of the AF aligns with the locking snap of the LOS, causing the locking snap to deflect radially through the locking opening, during proximal movement of the LOS due to the biasing force of the BE, with reciprocal axial movement of the syringe so as to proximally retract the syringe chamber with the needle into the housing, until the locking snap passes the proximal end of the IH and returns to a non-deflected position, and the LOS stopping protrusion engages the IH stopping protrusion preventing further proximal movement of the LOS, and the locking snap restricts further distal movement of the LOS. The LOS may further include: a first locking window, disposed on the extending arm, distally of the gripping snap, a second locking window, disposed on the extending arm, distally of the first locking window, and at least one LOS stopping protrusion, disposed at the distal end of the extending arm, where the IH further includes at least one IH locking snap, disposed on a distally extending portion of the inner tube of the IH, the IH locking snap including a locking tooth at a proximal end thereof, where the LOS stopping protrusion is aligned angularly with the IH locking snap, and where the locking tooth of the IH locking snap is positioned within the first locking window, when the assembly is in a non-deployment position. The assembly may further include a removable needle guard, configured to cover the distal end of the needle when the assembly is in the non-deployment state, where the needle guard includes a proximal ring and a distal ring, radially encircling the outer circumferential surface of the needle guard, the diameter of the distal ring being smaller than the diameter of the proximal ring, and the assembly may further include an outer cap, positioned at the distal end of an external housing (EH) of the housing, the IH fixedly coupled to the EH at the proximal end thereof, the outer cap including: a cap body, a cap tube, proximal to the cap body, a connecting wall, separating the cap body from the cap tube, and at least one cap snap, disposed within the cap body and inclined radially inward, where the distal end of the cap snap is positioned proximal of the distal ring of the needle guard and the inner portion of the connecting wall is positioned distal of the proximal ring of the needle guard, such that the distal end of the cap snap engages with the distal ring so as to distally pull the needle guard with the outer cap upon distal pulling of the outer cap. The method may further include the procedure of proximally retracting the syringe chamber with the needle into the housing, during proximal movement of the LOS due to the biasing force of the BE, with reciprocal axial movement of the syringe such that the stopping protrusion of the LOS engages the distal end of the IH, preventing further proximal movement of the LOS, and aligning the locking snap of the IH such that the locking tooth is positioned within the second locking window of the LOS, causing the locking snap to return to a non-deflected position, and the proximal end of the locking tooth engages the proximal end of the second locking window, preventing further distal movement of the LOS and the syringe.

BRIEF DESCRIPTION OF THE DRAWINGS

The present invention will be understood and appreciated more fully from the following detailed description taken in conjunction with the drawings in which.

DETAILED DESCRIPTION OF THE EMBODIMENTS

The present invention overcomes the disadvantages of the prior art by providing an automatically retracting safety needle assembly that activates a safety retraction mechanism after completion of the injection, while minimizing the likelihood of the user inadvertently terminating the syringe plunger depression before the injection has fully completed, and without requiring the application of additional force by the user (i.e., in addition to the basic injection force) in order to activate the safety mechanism. When the user depresses the syringe plunger to perform the injection, the safety needle assembly does not exert an additional opposing resistance force with an abrupt resistance increase for activation of the safety mechanism, as common in conventional spring-loaded safety syringes. Rather, the user encounters a relatively constant resistance force throughout the advancement of the syringe plunger along the syringe chamber that compels a continuous depressing of the syringe plunger, thus enabling full completion of the injection process with high reliability and avoiding its premature termination, and substantially ensuring the activation of the safety mechanism. The completion of the injection, as signified by at least one visual/audible/tactile indicator on the safety needle assembly, provides for full expulsion of the injectant substance via the syringe needle and enables the release of the retraction mechanism restraints. This is followed by the automated syringe retraction, allowing for safe discarding of the needle to prevent potential hazards by a contaminated exposed needle, such as needlestick injury.

Figure 1:
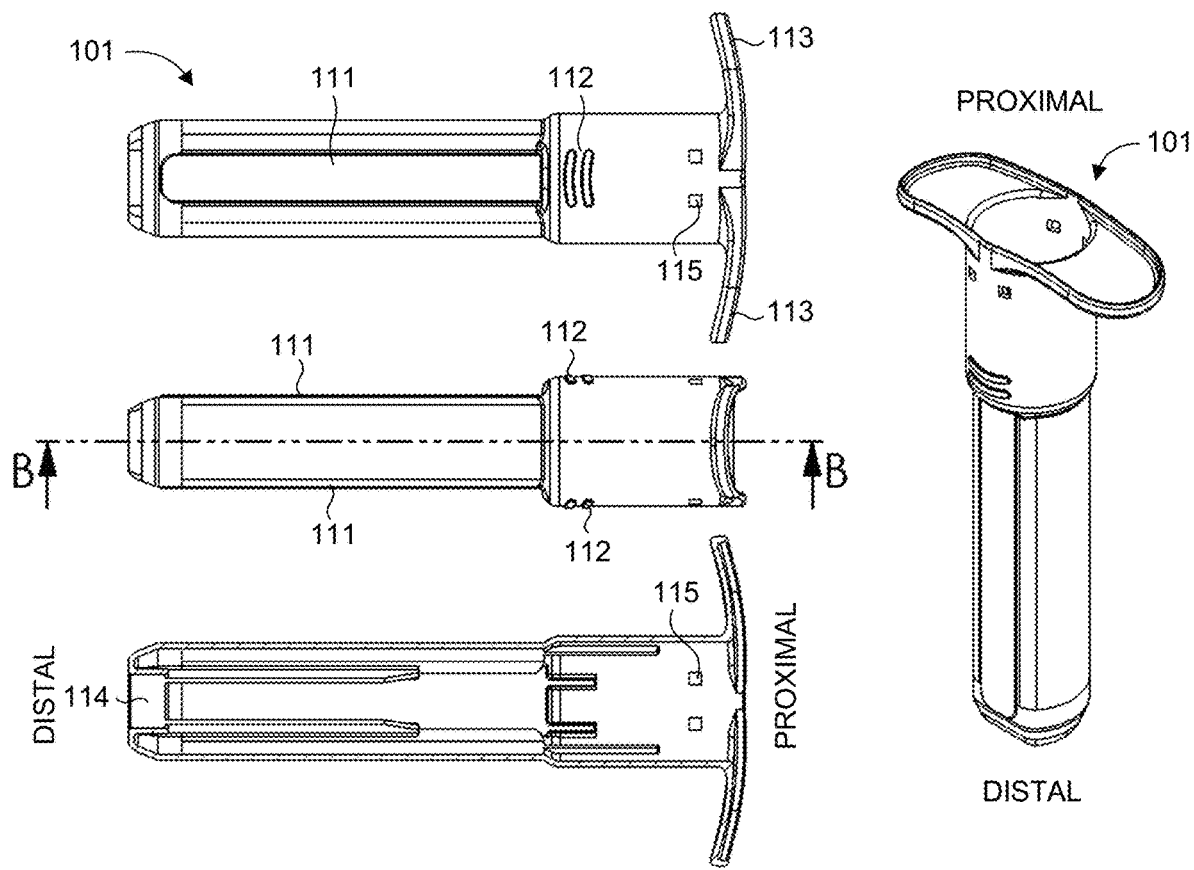
FIG. 1 is an illustration of an external housing for a safety needle assembly, constructed and operative in accordance with a first embodiment of the present invention, the illustration including a perspective view, orthogonal side views, and a sectional view of the external housing.

Reference is now made to FIGS. 1 through 14, which collectively illustrate a safety needle assembly, generally referenced 100, according to a first embodiment of the present invention. Assembly 100 includes an external housing (EH) 101, an internal housing (IH) 102, a rotating sleeve (ROS) 103, a biasing element (BE) 104, an activation fork (AF) 105, and a syringe 106. Assembly 100 has a distal end and a proximal end, which is depicted in FIG. 1 in the context of external housing 101, where the distal end faces away from the user holding assembly 100 and towards the injection site. Assembly 100 is also defined by a longitudinal axis, extending lengthwise along the assembly between the proximal and distal ends, where an "axial" direction corresponds to a direction parallel to the longitudinal axis (i.e., towards or away from the proximal or distal ends), whereas a "radial" direction corresponds to a direction orthogonal to the longitudinal axis, and extending radially therefrom.

FIG. 1 is an illustration of external housing 1 of safety needle assembly 100, including a perspective view, orthogonal side views, and a sectional view thereof. External housing 101 is primarily cylindrical or tubular shaped and encases the other components of assembly 100. External housing 101 includes at least one grip 112, disposed at a proximal portion on the exterior surface of external housing 101, by which the user can hold onto or grip assembly 100. External housing 101 further includes a pair of transparent windows 111, arranged lengthwise on the exterior surface of external housing 101 between grip 112 and the distal end of external housing 101. Windows 111 are configured to provide a view of the injectant substance prior to and during the injection process, such that the user can observe relevant characteristics relating to the substance, such as the substance quality, as well as if and how much of the substance is actually being injected. While two windows 111 are depicted for exemplary purposes, external housing 101 may generally include any number of windows, and may be characterized by any suitable size or shape. External housing 101 further includes a flange 113, consisting of opposing ledges or protrusions projecting radially outward at the proximal end of external housing 101, such that the user can press his fingers against flange 113 to provide a counterforce when depressing the syringe plunger (e.g., by applying a clamping force with his fingers between flange 113 and the syringe plunger rod 161 of syringe 106 as described hereinbelow). An opening 114 at the distal end of external housing 101 allows the syringe needle to extend through opening 114 during the injection process. A plurality of small apertures 115 are symmetrically arranged on opposing sides of external housing 101 at the proximal end of grip 112 distally of flange 113, with two apertures positioned adjacently on each side. It is appreciated that external housing 101 may be considered optional and assembly 100 may alternatively be configured without external housing 101, for example, where associated external housing components, such as grip 112 and flange 113, may alternatively be disposed directly on internal housing 102.

Figure 2:
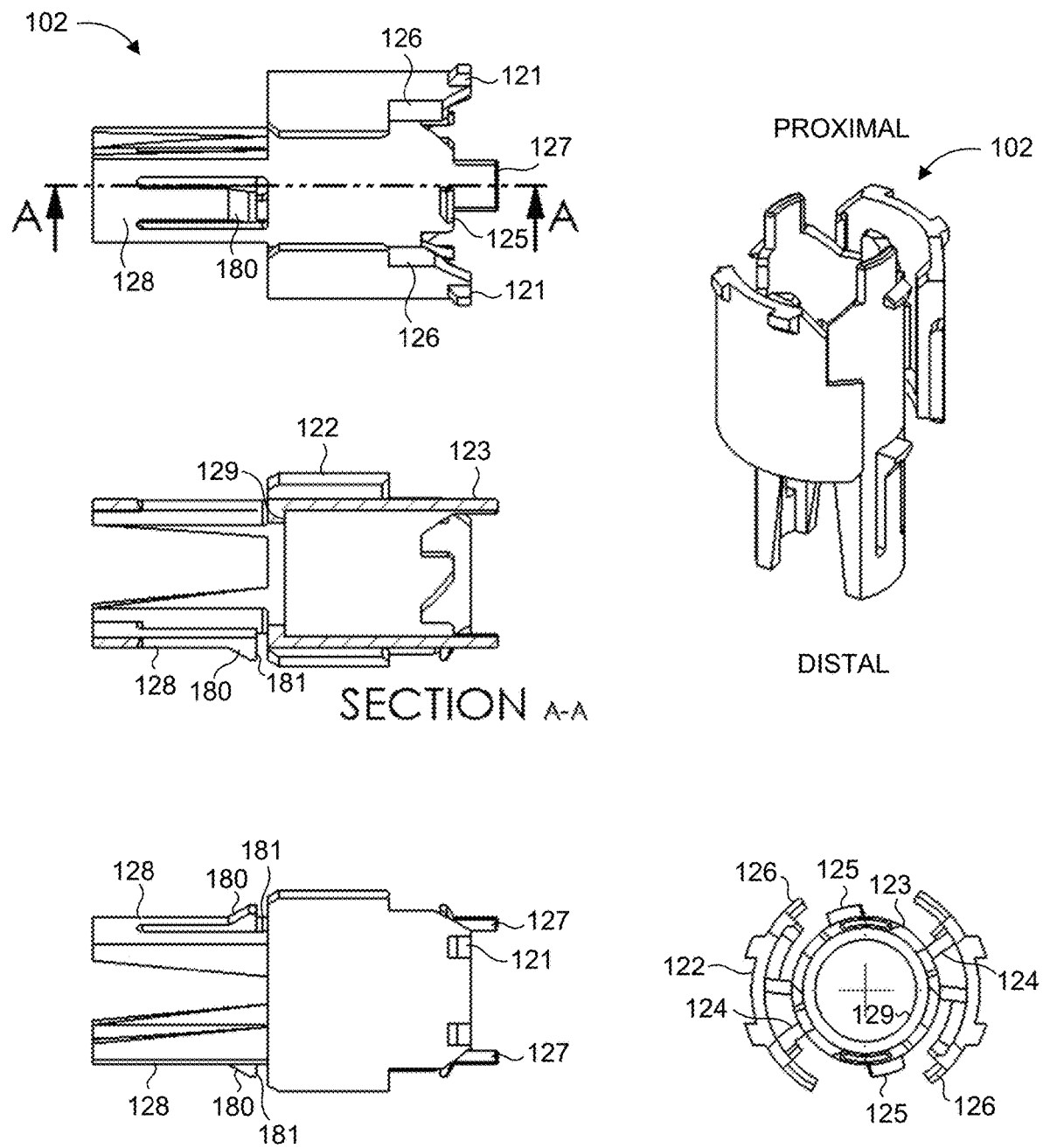
FIG. 2 is an illustration of an internal housing for a safety needle assembly, constructed and operative in accordance with a first embodiment of the present invention, the illustration including a perspective view, side and top views, and a sectional view of the internal housing.

FIG. 2 is an illustration of internal housing (IH) 102 of safety needle assembly 100, including a perspective view, side and top views, and a sectional view thereof. Internal housing 102 includes an inner tube 123 concentrically disposed within an outer tube 122, where inner tube 123 is affixed to outer tube 122 via a pair of radially extending connecting ribs 124. A base wall 129 is positioned within inner tube 123. A pair of directing protrusions 125 project outwards radially from the outer wall of inner tube 123. Guiding ribs 126 are situated on opposite sides on the inner part of outer tube 122. Internal housing 102 includes two pairs of short connecting protrusions 121, each pair extending radially outwards at the proximal end of outer tube 122 at a respective side thereof. Internal housing 102 further includes a pair of short orienting protrusions 127 extending axially and located at the proximal end of inner tube 123. Internal housing 102 further includes a pair of locking snaps 128, which are larger elongated projections extending axially from opposite sides at the distal end of internal housing 102. Each locking snap 128 is characterized by a substantially straight proximal surface 181. Locking snap 128 includes a triangular-shaped ridge 180 protruding radially outwards from the outer surface of locking snap 128 and generally facing distally.

It should be noted that the "external housing" and the "internal housing" can be considered two parts of a single component which can be collectively referred to as a "housing". Accordingly, external housing 101 and internal housing 102 are represented herein as two separated pieces or components for convenience of manufacturing considerations, but can alternatively can be manufactured as a single integral component using different manufacturing technologies.

Figure 3:
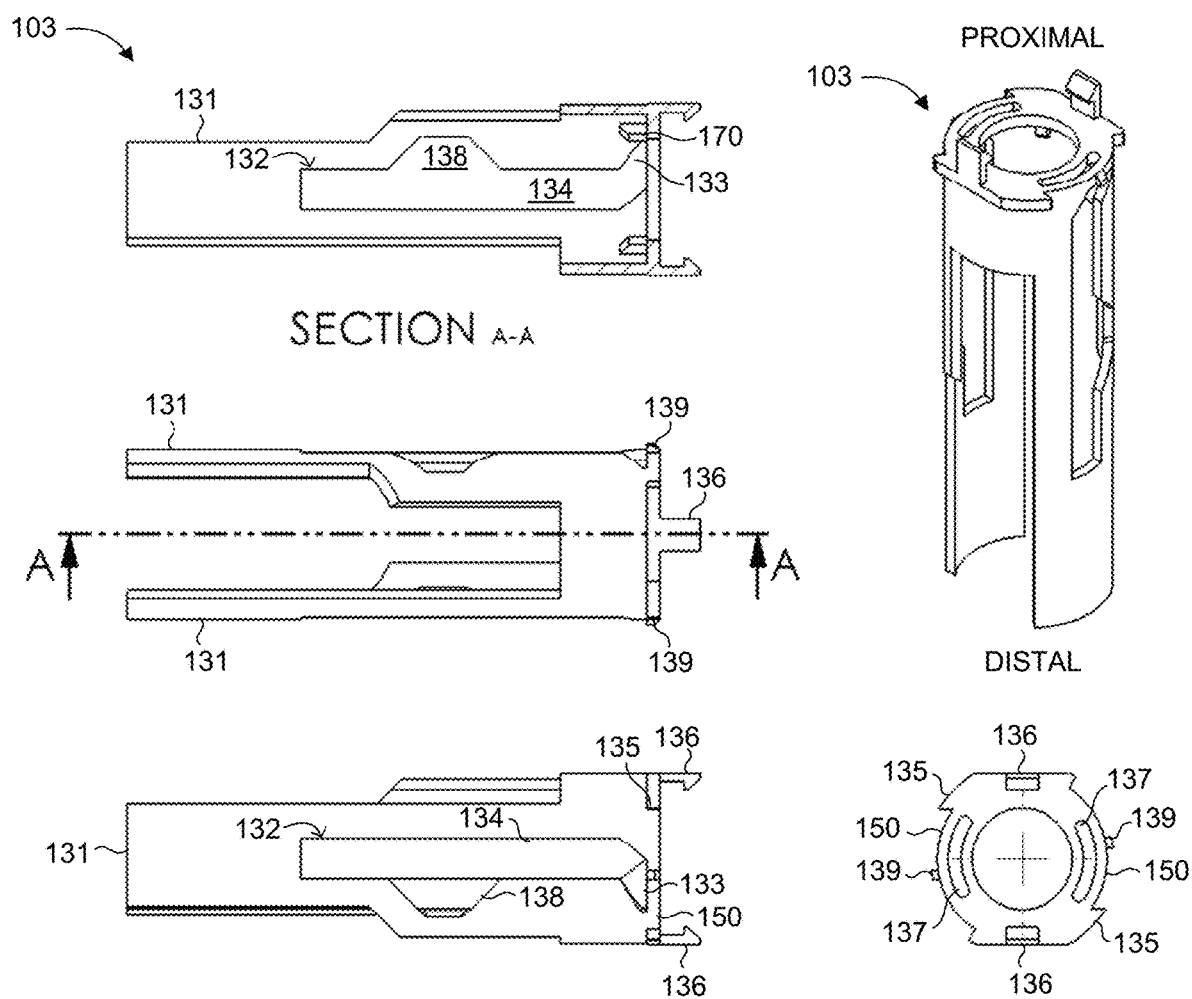
FIG. 3 is an illustration of a rotating sleeve for a safety needle assembly, constructed and operative in accordance with a first embodiment of the present invention, the illustration including a perspective view, side and top views, and a sectional view of the rotating sleeve.

FIG. 3 is an illustration of rotating sleeve (ROS) 103 of safety needle assembly 100, including a perspective view, side and top views, and a sectional view thereof. ROS 103 is generally cylindrical or tubular shaped with a hollow core, and includes a pair of extending arms 131 extending distally from a flange wall 170 at the proximal end of ROS 103. The inner diameter and axial length of ROS 103 are larger than that of inner tube 123 of internal housing 102. Each extending arm 131 has an opening or guiding slot 132 consisting of different slot sections: a short helical-shaped slot portion 133 at the proximal edge; an elongated straight slot portion 134 distal of helical-shaped slot portion 133; and a semi-hexagonal shaped extension slot portion 138 extending from the middle of straight slot portion 134. Flange wall 170 has a pair of arc-shaped openings 137 symmetrically arranged on opposite sides. Flange wall 170 is further characterized by notched flanges 135 protruding radially outwards on opposite sides, adjacent to openings 137. Each notched flange 135 is characterized by a wide notch 150. A pair of teeth 139 projects radially outwards from the perimeter of flange wall 170 in between notched flanges 135. ROS 103 further includes a pair of holding snaps 136, which are short protrusions projecting proximally from the edges of flange wall 170, arranged orthogonal to wide notches 150. It is noted that certain components of ROS 103 are described herein for exemplary purposes as being of a plurality, such as: two extending arms 131; two arc-shaped openings 137; two notched flanges 135; two holding snaps 136; and two teeth 139. However, ROS 103 may more generally be configured with any number of these respective components, such as for example, by including only one extending arm 131; one arc-shaped opening; one notched flange 135; one holding snap 136; and/or one tooth 139, in an alternative embodiment. In a further alternative embodiment, ROS 103 may be configured with an outer diameter that is smaller than the inner diameter of inner tube 123 of IH 102. Correspondingly, the pair of directing protrusions 125 of IH 102 may project radially inwards from the inner wall of inner tube 123 (i.e., rather than projecting radially outwards), and the triangular-shaped ridge 180 of locking snap 128 of IH 102 may protrude radially inwards from the outer surface of locking snap 128 (rather than protruding radially outwards) and generally face distally.

Biasing element 104 may be embodied, for example, by a compression spring, or more generally by any suitable device or mechanism configured to apply an axial biasing force against ROS 103 and IH 102.

Figure 4:
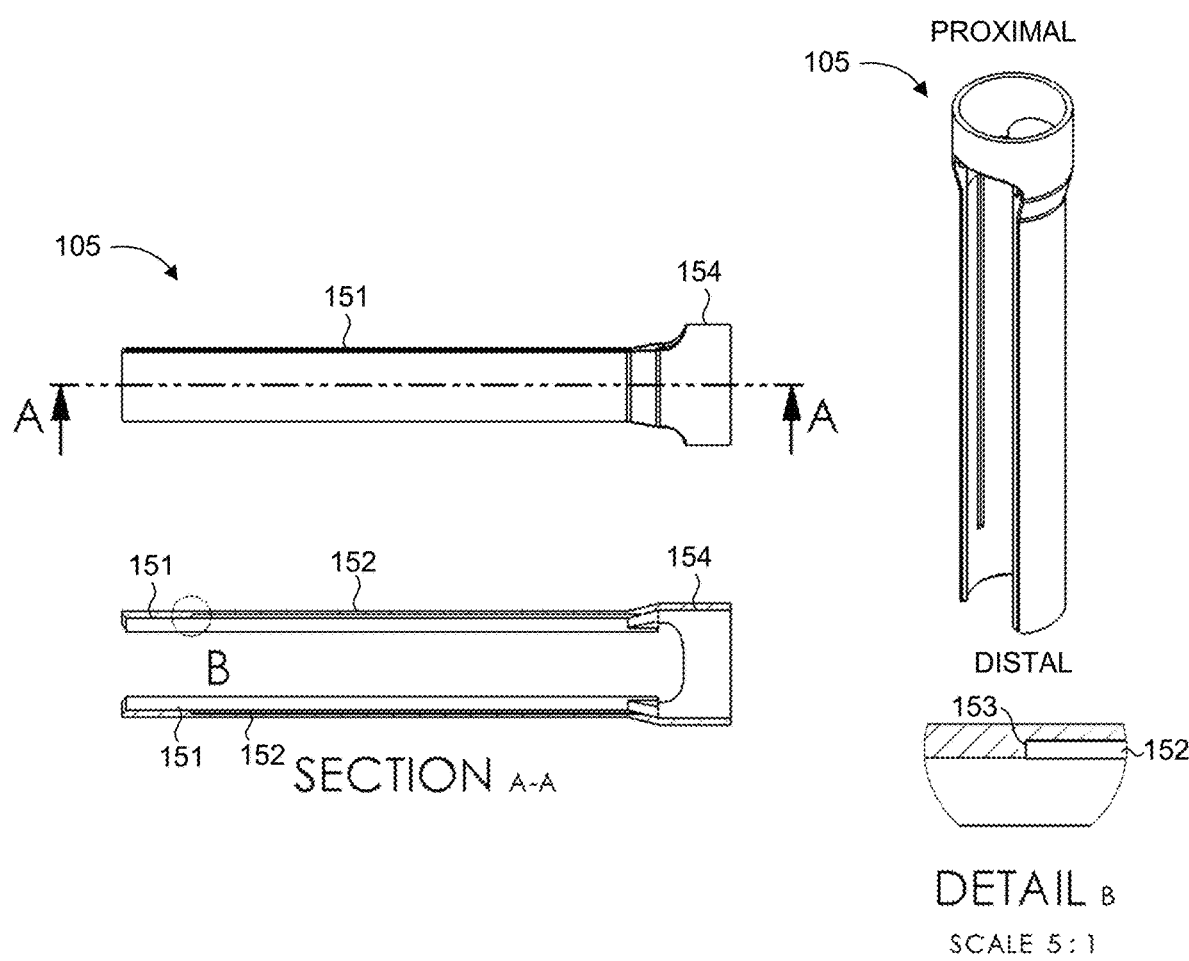
FIG. 4 is an illustration of an activation fork for a safety needle assembly, constructed and operative in accordance with a first embodiment of the present invention, the illustration including a perspective view, a side view, a sectional view, and a detailed view of the activation fork.

FIG. 4 is an illustration of activation fork (AF) 105 of safety needle assembly 100, including a perspective view, a side view, a sectional view, and a detailed view thereof. AF 105 is generally cylindrical or tubular shaped with a hollow core and includes a pair of arc-shaped guiding arms 151 extending distally from an end member 154 at the proximal end of AF 105. End member 154 is generally circular and "ring" shaped, i.e., with a hollow central portion, but may alternatively be a different shape or form, such as a filled (non-hollow) plate. End member 154 has a slightly larger radius than that of guiding arms 151 (along the radial axis). Each guiding arm 151 has a groove 152 extending longitudinally along the inner surface thereof, where the groove 152 terminates at a shoulder 153 at the distal end of guiding arm 151. It is noted that AF 105 may alternatively be configured with only a single guiding arm 151, or more generally may be configured with any number of guiding arms 151, but is described herein for exemplary purposes as including two guiding arms 151.

Figure 5:
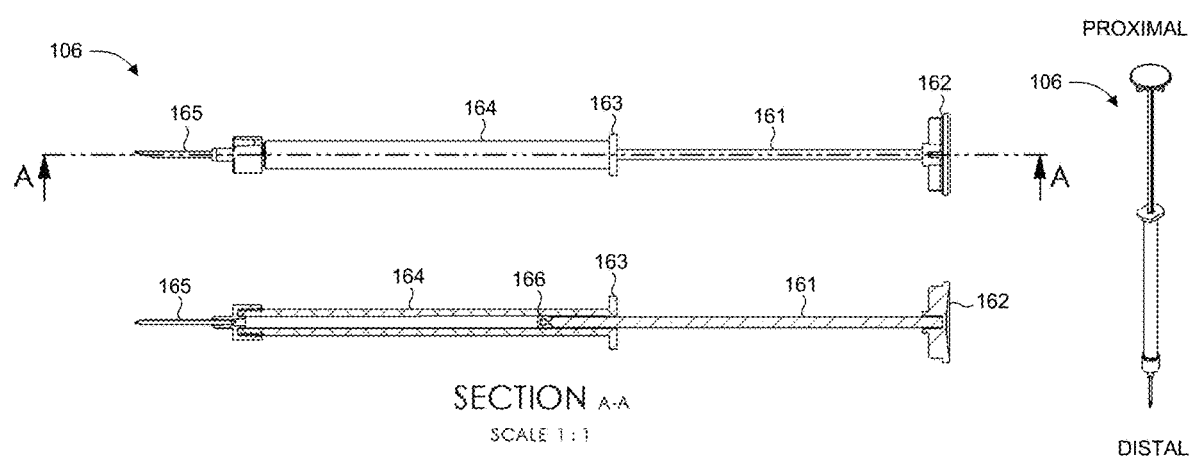
FIG. 5 is an illustration of a syringe of a safety needle assembly, constructed and operative in accordance with a first embodiment of the present invention, the illustration including a perspective view, a side view, and a sectional view of the syringe.

FIG. 5 is an illustration of syringe 106 of safety needle assembly 100, including a perspective view, a side view, and a sectional view thereof. Syringe 106 includes a cylindrical syringe chamber 164, which is bordered at its proximal end by a syringe flange 163. Syringe 106 further includes a needle 165 which extends from the distal end of syringe 106, distally from syringe chamber 164. Syringe 106 further includes a syringe plunger rod 161 bordered at its proximal end by a finger rest 162, which is typically a disc with its surface orthogonal to the longitudinal axis. A plunger stopper 166 is disposed at the distal end of plunger rod 161. Plunger rod 161 is slidable advanceable within syringe chamber 164, such that when plunger rod 161 is pressed forward (in a distal direction) in syringe chamber 164, such as due to the application of force against finger rest 162, an injectant substance contained within syringe chamber 164 is propelled distally by plunger stopper 166 through needle 165.

Figure 6:
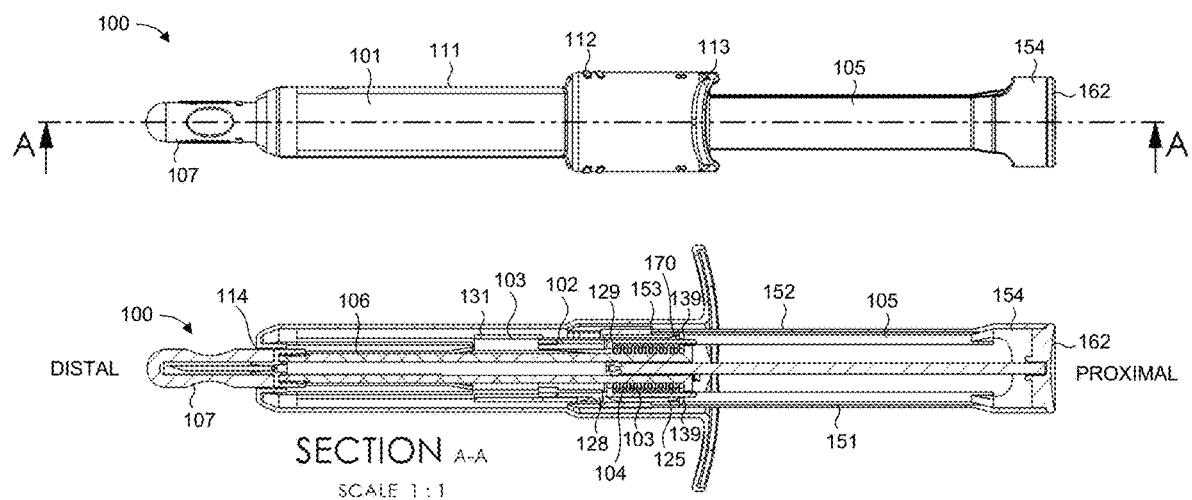
FIG. 6 is an illustration of a safety needle assembly in a storage state, constructed and operative in accordance with a first embodiment of the present invention, the illustration including a first side view and a corresponding sectional view of the safety needle assembly.
Figure 7:
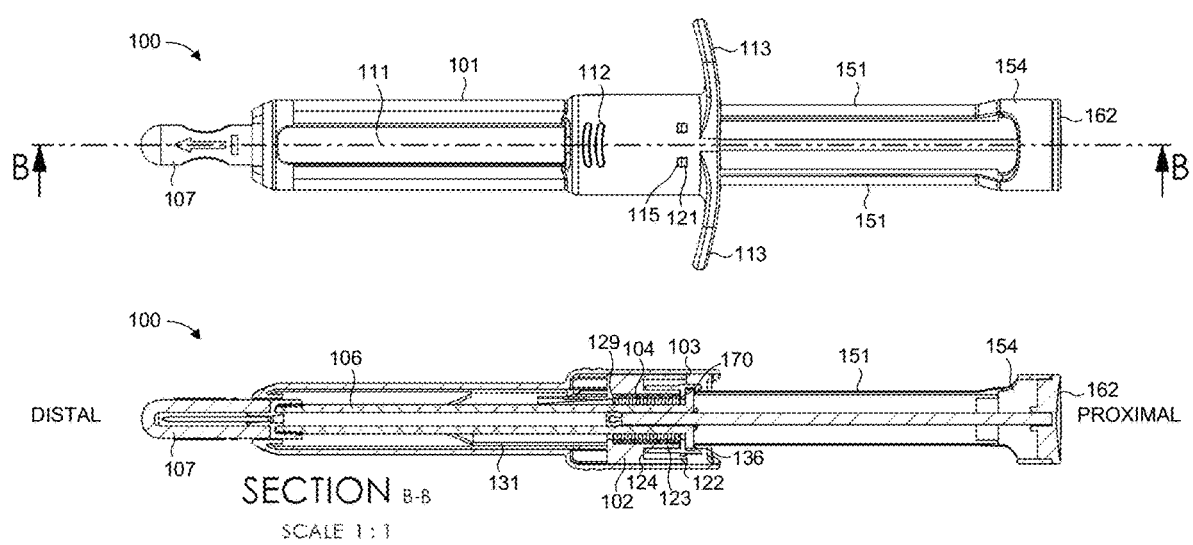
FIG. 7 is an illustration of a safety needle assembly in a storage state, constructed and operative in accordance with a first embodiment of the present invention, the illustration including a second side view and a corresponding sectional view of the safety needle assembly.
Figure 8:
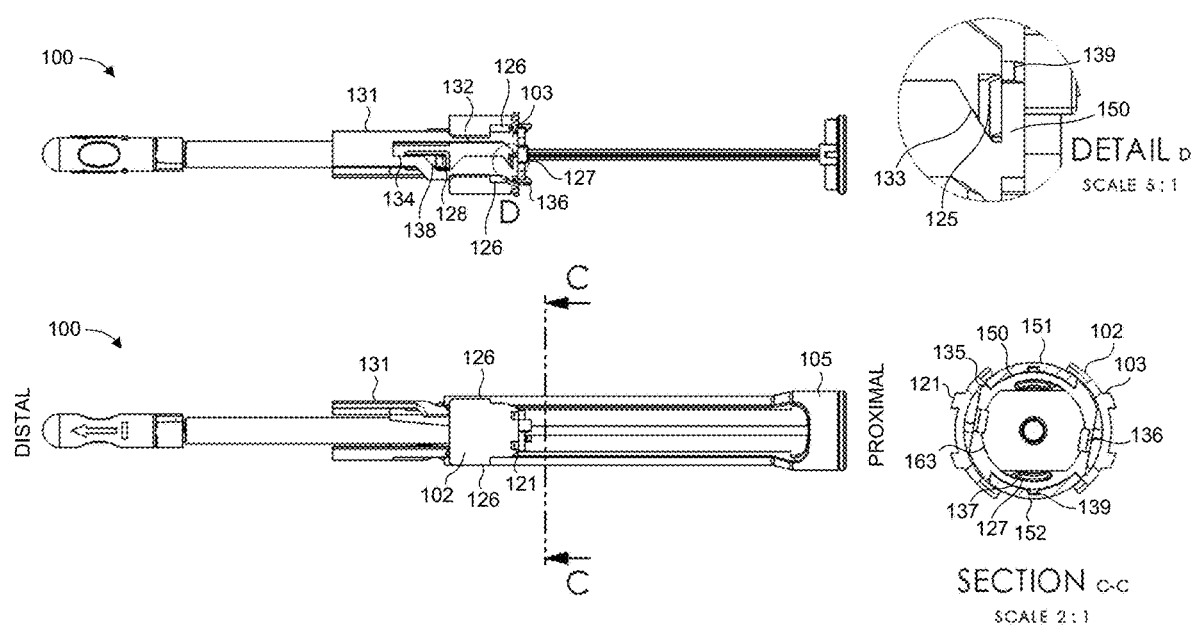
FIG. 8 is an illustration of the internal components of a safety needle assembly in a storage state, constructed and operative in accordance with a first embodiment of the present invention, the illustration including a side view and a detailed view of the safety needle assembly where the external housing and activation fork are concealed from view, the illustration further including a side view and a sectional view where only the external housing is concealed from view.

FIGS. 6 through 8 provide different views of safety needle assembly 100 in a "storage state" or a "non-deployment state", representing the configuration of assembly 100 when not in use (i.e., before implementing an injection). Internal housing 102 is concentrically arranged within external housing 101 and is fixedly coupled to external housing 101 by connecting protrusions 121 of internal housing 102 engaging with apertures 115 at the proximal end of external housing 101. In the event that external housing 101 and internal housing 102 are formed as a single integrated component, then protrusions 121 of internal housing 102 and apertures 115 of external housing 101 can be eliminated and outer tube 122 of internal housing 102 can be formed as part of external housing 101. ROS 103 is also concentrically arranged within external housing 101. In particular, ROS 103 is disposed between outer tube 122 and inner tube 123 of internal housing 102, where extending arms 131 extend through the distal end of internal housing 102 and directing protrusions 125 on the outer wall of inner tube 123 are positioned within helical-shaped slot portion 133 of guiding slots 132 of respective extending arms 131. Locking snaps 128 of internal housing 102 are positioned within slot extensions 138 of guiding slots 132 of respective extending arms 131. Orienting protrusions 127 at the proximal end of inner tube 123 are positioned through arc-shaped openings 137 of flange wall 170 of ROS 103.

BE 104 is disposed within inner tube 123, and supported at its distal end by base wall 129 of internal housing 102 and supported at its proximal end by flange wall 170 of ROS 103. Guiding arms 151 of AF 105 are positioned between ROS 103 and outer tube 122 of IH 102. In particular, end member 154 at the proximal end of AF 105 is coupled to finger rest 162 of syringe plunger rod 161, while guiding arms 151 of AF 105 are guided by guiding ribs 126 on the inner part of outer tube 122. Guiding arms 151 are also positioned inside wide notch 150 of notched flange 135 at proximal end of ROS 103, and teeth 139 of notched flange 135 are inserted in groove 152 on the inner surface of guiding arms 151. Syringe 106 is positioned within inner tube 123 of IH 102 and coupled to ROS 103 by holding snaps 136.

BE 104 applies an axial force (e.g., a spring force) that biases ROS 103 to the proximal direction. ROS 103 is rotatable and axially movable but is prevented from rotation and axial movement when in storage position by AF 105 (i.e., due to the positioning of guiding arms 151 within wide notch 150 of notched flange 135). Syringe 106 is rotatable and axially movable but is prevented from such when in storage position, as holding snaps 136 and flange wall 170 prevent axial motion of syringe flange 163 relative to ROS 103, while orienting protrusions 127 prevent rotation of syringe flange 163. AF 105 is limited from further proximal motion by teeth 139 of ROS 103 engaging with shoulder 153 of guiding arm 151, preventing the removal of AF 105 from assembly 100.

When assembly 100 is in a storage state, syringe needle 165 extends at least partially through distal opening 114 and is encased by a needle guard 107. Needle guard 107 is a short thin tube which is opened at its proximal end and closed at its distal end. The proximal edge of needle guard 107 is partially embedded within opening 114. Needle guard 107 is tightly wrapped around the base of needle 165. Needle guard 107 serves to prevent contamination or needle-stick injury from an exposed needle 165, and acts as a barrier for the injectant substance when assembly 100 is in a storage state.

Figure 9:
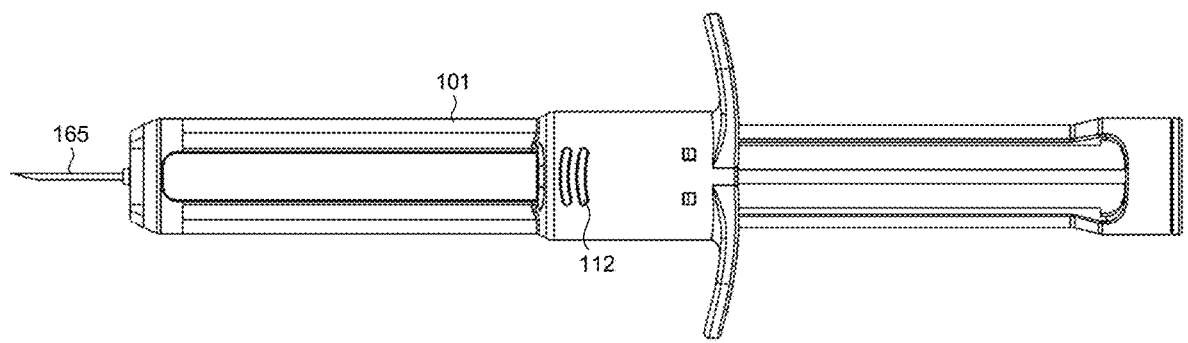
FIG. 9 is a side view illustration of a safety needle assembly during a needle insertion stage, operative in accordance with a first embodiment of the present invention.
Figure 10:
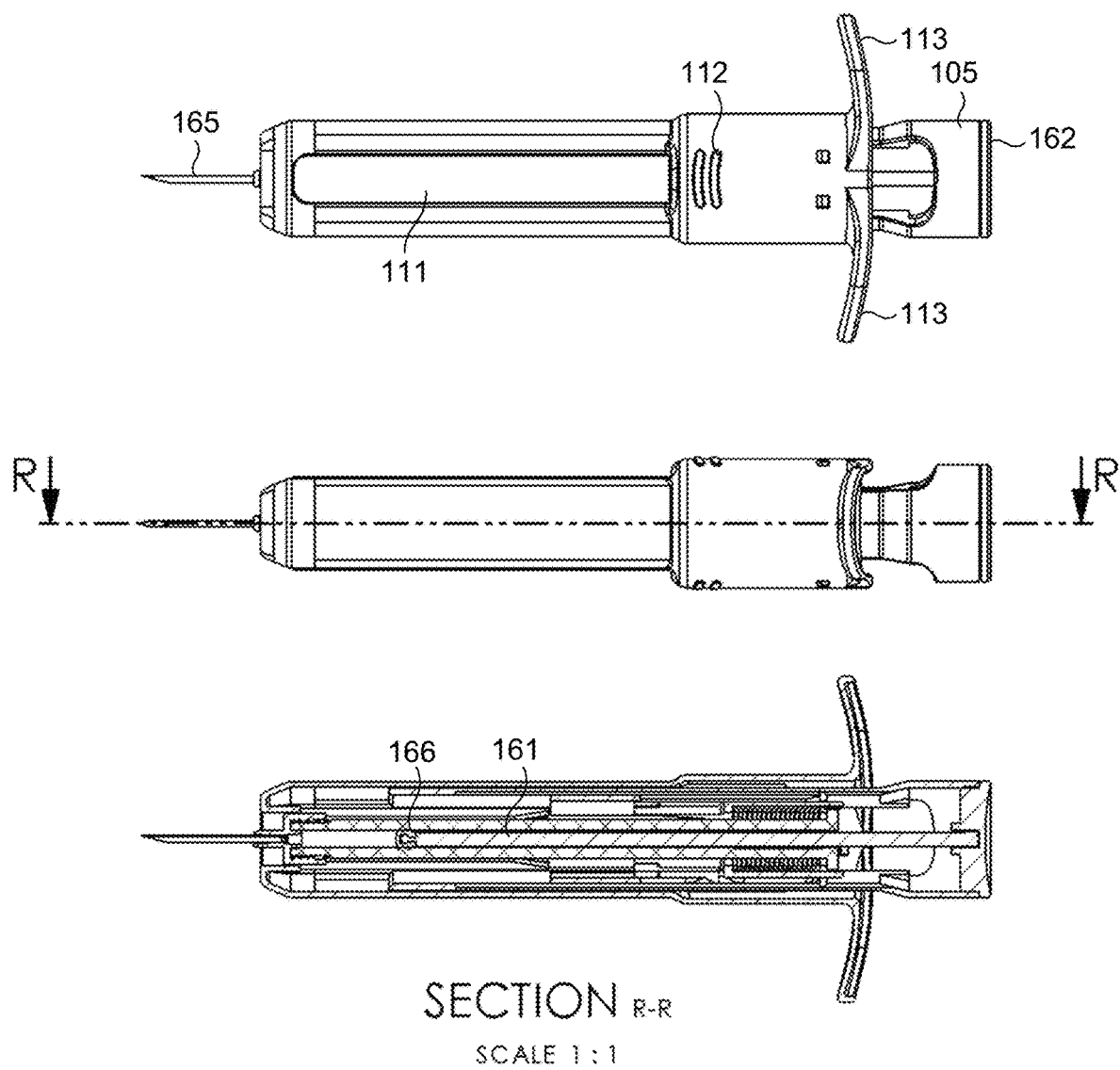
FIG. 10 is an illustration of a safety needle assembly during an injection stage, operative in accordance with a first embodiment of the present invention, the illustration including orthogonal side views, and sectional views of the safety needle assembly.

To deploy assembly 100 for performing an injection, a user (e.g., a medical clinician) holds assembly 100, preferably via grip 112, and removes needle guard 107, such as by pulling needle guard 107 in the distal direction, to expose needle 165. The user inserts the exposed distal end of needle 165 into an injection site (e.g., a body region of a patient to be injected). FIG. 9 is a side view illustration of safety needle assembly 100 during a needle insertion stage. After needle 165 has been inserted into the injection site, the user presses syringe finger rest 162 which pushes plunger rod 161 in the distal direction together with AF 105. The distal advancement of plunger rod 161 mutually advances plunger stopper 166 within syringe chamber 164, which propels the injectant substance distally within chamber 164 to pass through the distal aperture of needle 165 and enter the injection site. The progress of plunger rod 161 and plunger stopper 166 along chamber 164 and the passage of the injectant substance can be viewed through windows 111. FIG. 10 is an illustration of safety needle assembly 100 during an injection stage, including orthogonal side views and a sectional view.

Figure 11:
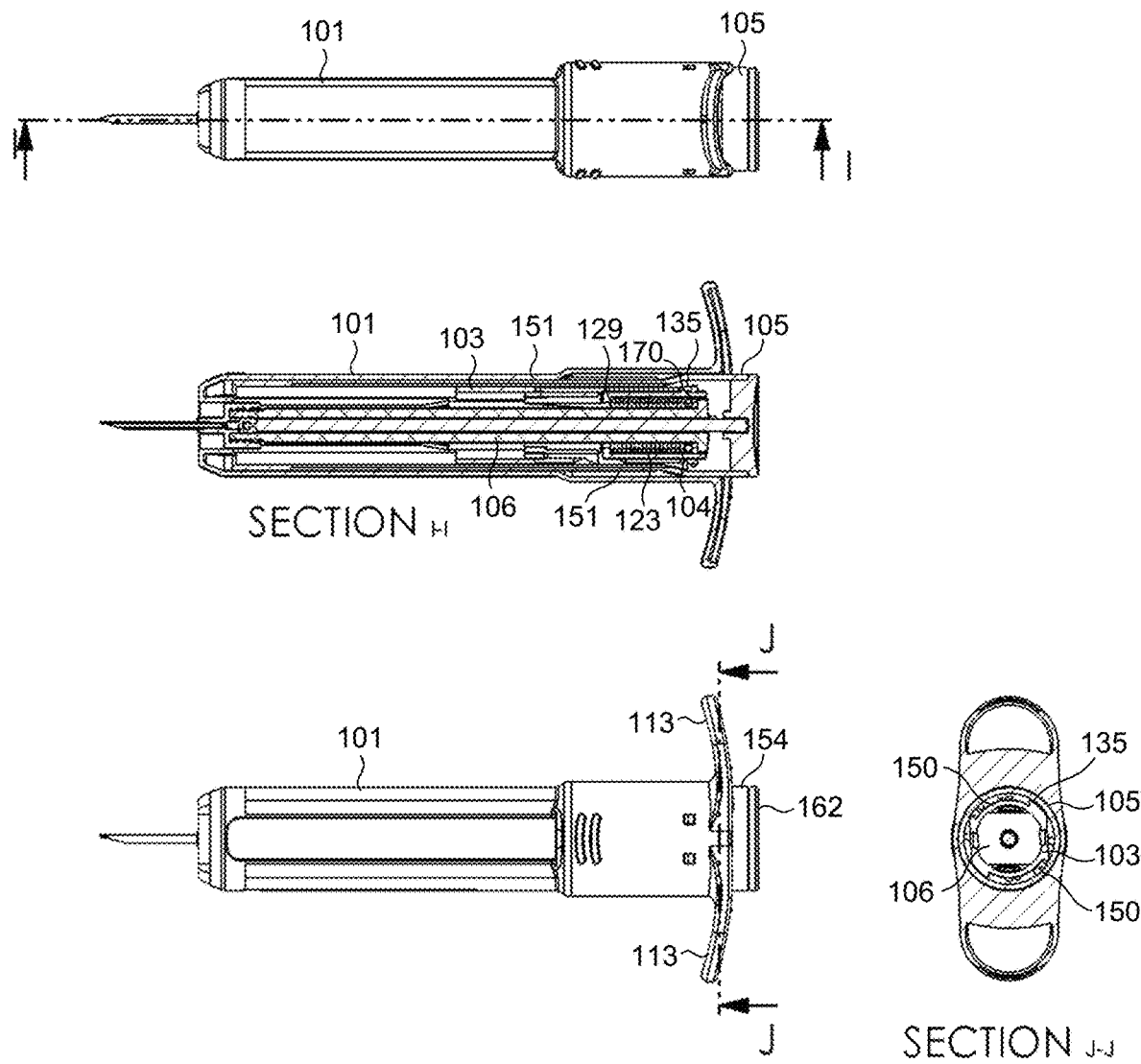
FIG. 11 is an illustration of a safety needle assembly during the end of the injection stage, operative in accordance with a first embodiment of the present invention, the illustration including orthogonal side views, and sectional views of the safety needle assembly.

The distal advancement of syringe plunger rod 161 continues until guiding arms 151 of AF 105 pass through wide notches 150 of notched flange 135 of ROS 103, allowing for rotation of ROS 103 inside end member 154 of AF 105. Syringe 106 and ROS 103 are held in place by the force applied by the user pressing (distally) against finger rest 162 at the end of syringe plunger rod 161. FIG. 11 is a side view illustration of safety needle assembly 100 during the end of an injection stage, including orthogonal side views and a sectional view, showing the respective alignments of ROS 103, AF 105 and syringe 106 at this stage.

Figure 28:
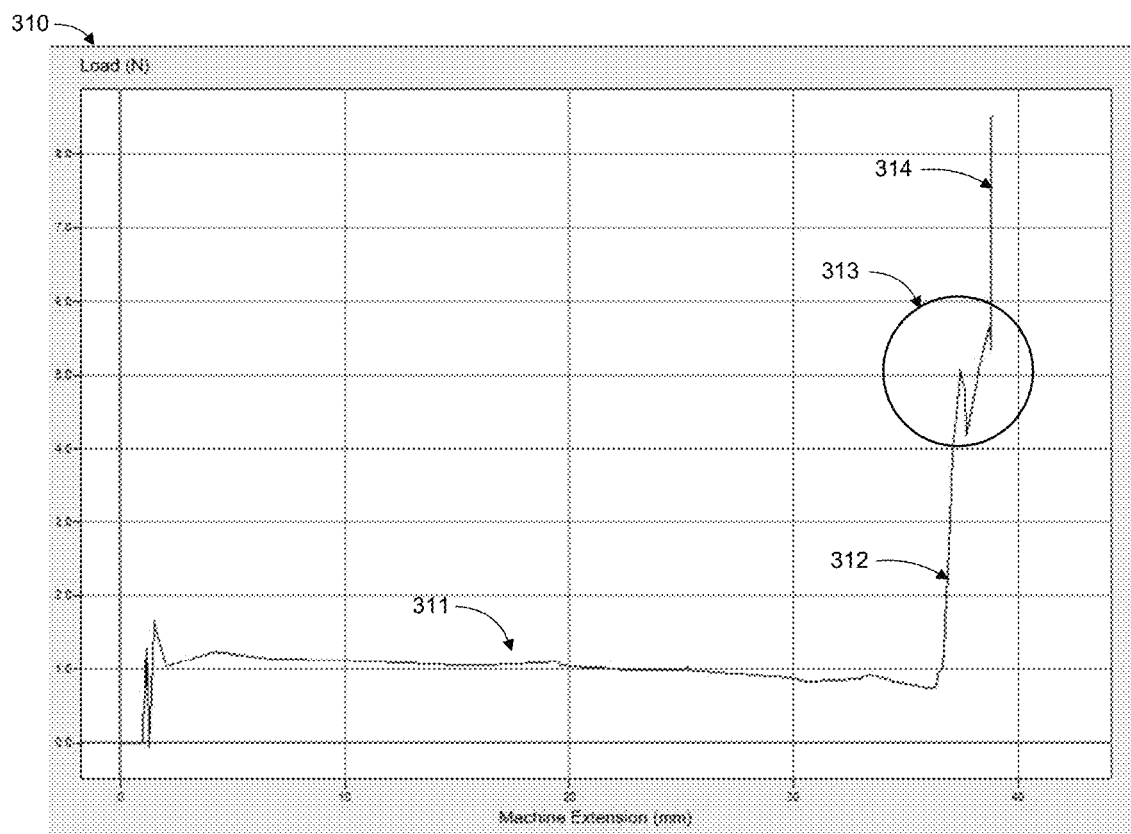
FIG. 28 is a graph of resistive force exerted against the user depressing the syringe plunger rod, as a function of the plunger rod displacement, of a standard safety needle assembly having an automatic retraction mechanism known in the art.
Figure 29:
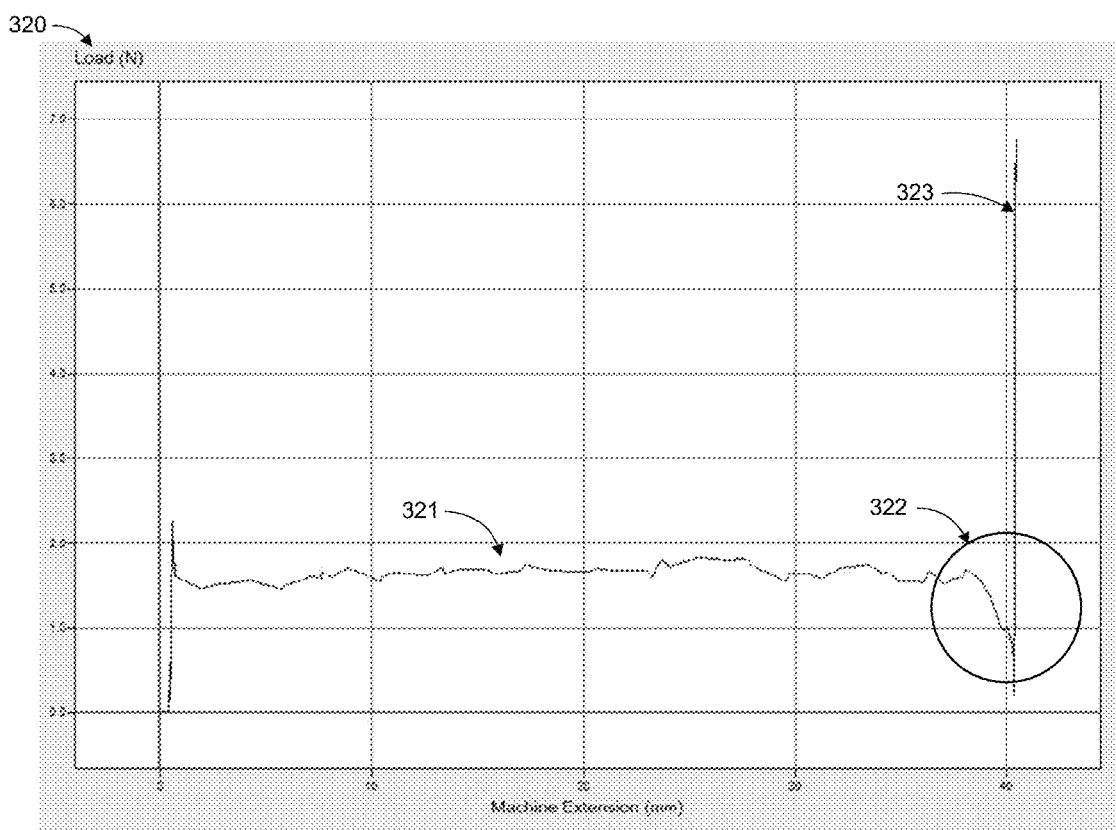
FIG. 29 is a graph of resistive force exerted against the user via the syringe finger rest, as a function of the plunger rod displacement, of a safety needle assembly operative in accordance with an embodiment of the present invention.
Figure 30:
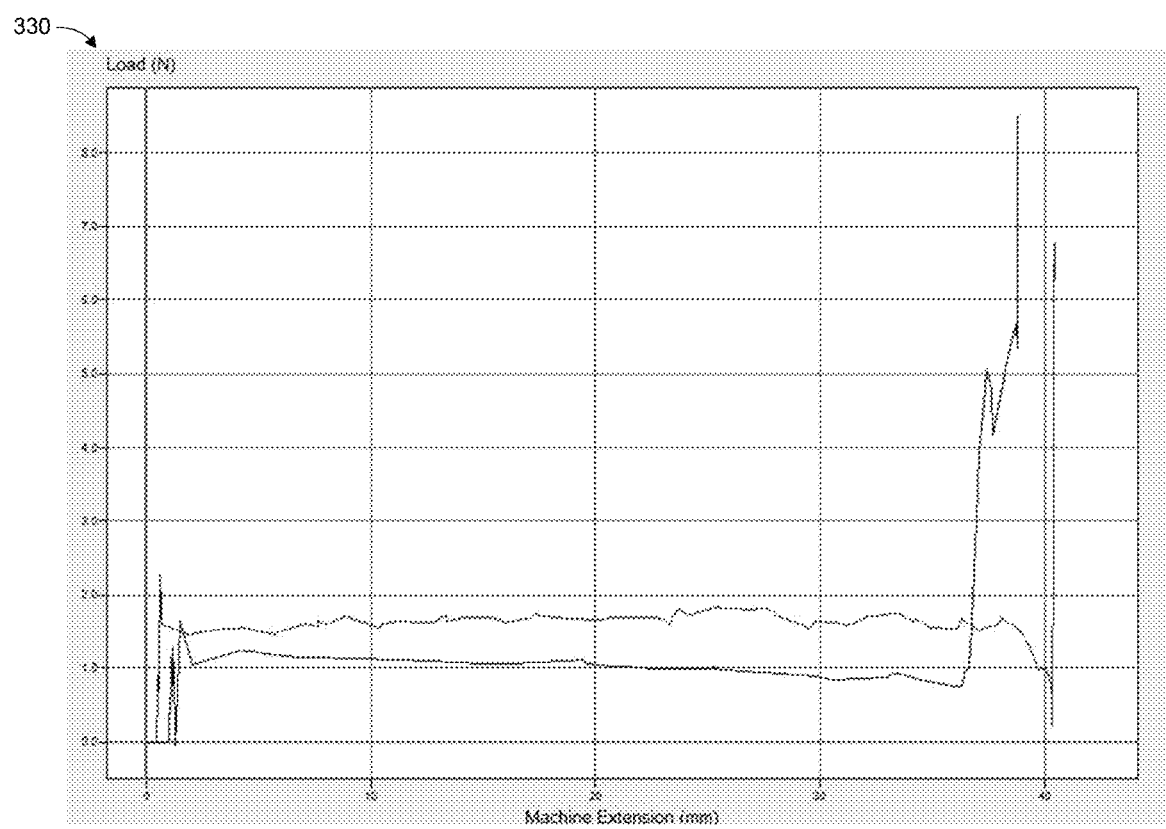
FIG. 30 is a comparison of the graph of FIG. 28 with the graph of FIG. 29.

Safety needle assembly 100 provides a smooth and substantially constant opposing resistive force during the advancement of syringe plunger rod 161, without an abrupt force increase needed to activate the safety retraction mechanism as in conventional (partially automated) safety syringes. The smooth and substantially constant resistance compels the user to fully depress syringe plunger rod 161 (by continuing to press against finger rest 162) without prematurely terminating the distal advancement of plunger rod 161 along syringe chamber 164 before the injection process has been fully carried out and the safety mechanism has been activated. Reference is now made to FIGS. 28, 29 and 30. FIG. 28 is a graph, generally referenced 310, of resistive force exerted against the user depressing the syringe plunger rod, as a function of the plunger rod displacement, of a standard safety needle assembly having an automatic retraction mechanism known in the art. FIG. 29 is a graph, generally referenced 320, of resistive force exerted against the user depressing the syringe plunger rod, as a function of the plunger rod displacement, of a safety needle assembly operative in accordance with an embodiment of the present invention. The x-axis of graphs 310, 320 represents the displacement or advancement of the syringe plunger along the syringe chamber (denoted as "machine extension") in millimeters (mm), while the y-axis represents the opposing or resistive force exhibited by the syringe (denoted as "load"), in Newtons (N). Graph 310 is characterized by an initial flat portion (referenced 311) representing an initial constant resistive force exhibited by the syringe of a standard safety needle assembly during the initial stages of the injection. After the syringe plunger has advanced beyond a certain point, there is an abrupt spike in resistive force, shown by curve portion 312 at approximately 37 mm. To overcome this resistive spike, the user must apply an increased counterforce to keep depressing the plunger and maintain its advancement in order to complete the injection process and to activate the retraction mechanism. As the syringe plunger advances further, the resistive force exhibits rapid conjoining peaks at curve portion 313 (at approximately 38-39 mm), signifying that the retraction restraint has been effectively released so as to trigger the activation of the retraction mechanism (where the pair of peaks represent the successive release of corresponding snaps which previously restrained the retraction mechanism in this example). The retraction mechanism activation is generally accompanied by an audible indication, such as a click sound, to signify the activation. A biasing force from the compression spring (or other biasing element) is subsequently applied against the activated retraction mechanism, producing an indefinite resistive force increase at curve portion 314. Thus, as seen in graph 310, a substantial user applied counterforce, of approximately 4 N, is required in order to overcome the resistive force needed to ensure full advancement of the syringe plunger and completion of the injection to activate the retraction mechanism in a standard partially automated retractable needle assembly.

In contrast, no such substantial user counterforce is needed for assembly 100. Graph 320 is also characterized by an initial flat portion 321 representing an initial constant resistive force during the initial injection phase. However, this constant resistive force continues throughout the advancement of the syringe plunger until the retraction mechanism is activated (due to the process elaborated upon further hereinbelow) at approximately 40 mm advancement. This is followed by a brief drop in resistive force (at curve portion 322), as the remainder of the injectant substance is expelled from the syringe needle, followed by an indefinite increase (at curve portion 323) due to the biasing force applied by biasing element 104. Accordingly, the relative constant resistance encountered in assembly 100 compels the user to continue to fully depress syringe plunger rod 161 (by pressing distally against finger rest 162), without prematurely terminating the distal advancement along syringe chamber 164 before the injection process has been fully carried out and the safety mechanism has been activated. A visual comparison of graphs 310 and 320 can be seen in FIG. 30.

Figure 12:
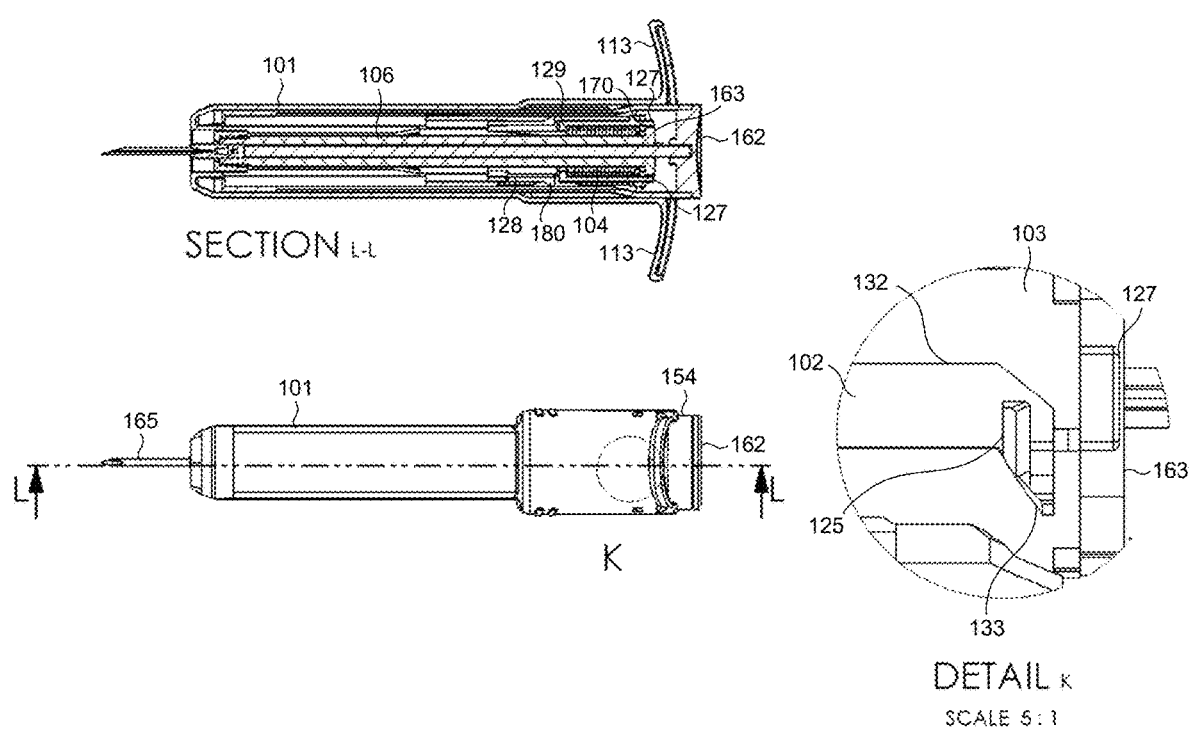
FIG. 12 is an illustration of a safety needle assembly during a first portion of a syringe retraction stage, operative in accordance with a first embodiment of the present invention, the illustration including a side view, a sectional view, and a detailed view of the safety needle assembly, where the external housing and the activation fork are concealed from view.
Figure 13:
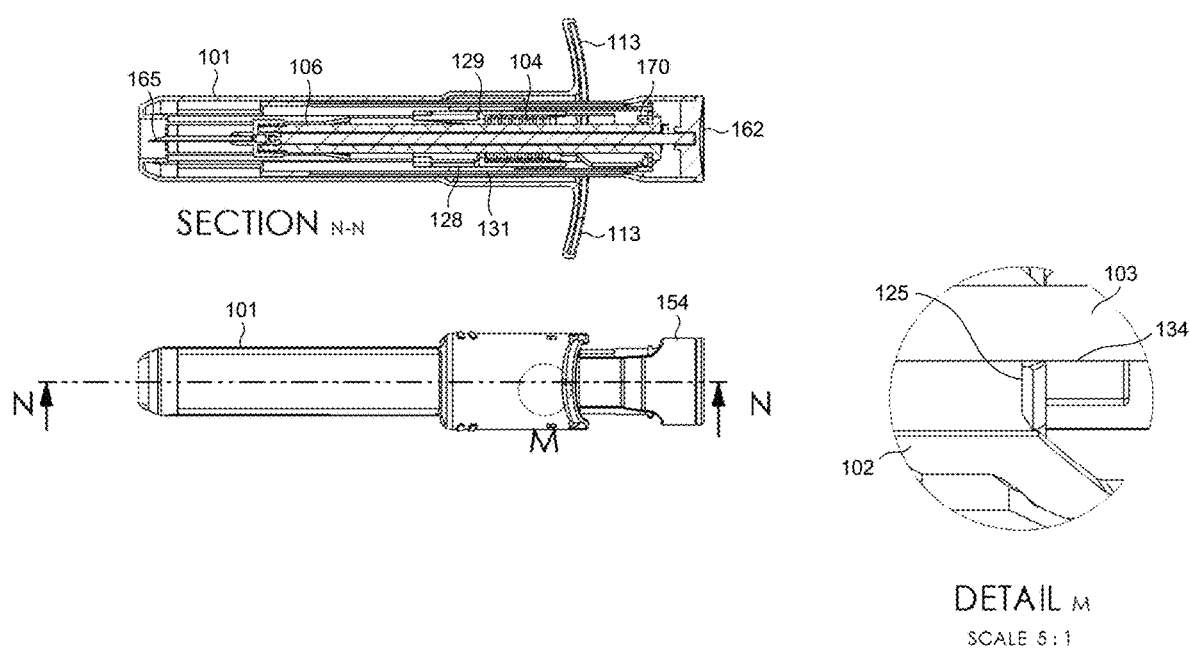
FIG. 13 is an illustration of a safety needle assembly during a second portion of the syringe retraction stage, operative in accordance with a first embodiment of the present invention, the illustration including a side view, a sectional view, and a detailed view of the safety needle assembly, where the external housing and the activation fork are concealed from view.

After the injection process is completed, the user releases the distal force applied to syringe plunger rod 161 by stopping to press finger rest 162, which reduces the axial force applied to syringe 106 and ROS 103. This allows the biasing force of BE 104 to move ROS 103 axially toward the proximal direction, resulting in directing protrusions 125 of IH 102 (initially positioned within helical-shaped slot portion 133 of guiding slots 132) urging rotation of ROS 103. Orienting protrusions 127 of IH 102 prevent rotation of syringe 106 by engaging syringe flange 163, thus limiting syringe 106 to axial motion. The rotation of ROS 103 causes locking snaps 128 to be repositioned out of slot extensions 138 and into elongated straight slot portion 134 of guiding slot 132. The rotation of ROS 103 also causes directing protrusions 125 to be repositioned out of helical-shaped slot portion 133 and into elongated straight slot portion 134 of guiding slot 132. This in turn allows for further axial movement of ROS 103 in the proximal direction. The proximal motion of ROS 103 causes ridge 180 on the outer surface of locking snap 128 to engage the distal end of guiding slots 132 and bend radially inwards to allow further proximal advancement of ROS 103. The proximal axial movement of ROS 103 is accompanied by the mutual proximal axial movement of syringe 106, which in turn causes syringe needle 165 to retract into the assembly housing (external housing 101 and/or internal housing 102). When the distal end of guiding slots 132 engages directing protrusions 125, the proximal motion of ROS 103 is restricted, while the distal end of extending arms 131 fully passes locking snaps 128, enabling locking snaps 128 to deflect radially outwards and return to a relaxed (unbent) position where proximal surface 181 of locking snaps 128 restricts distal movement of ROS 103 and syringe 106. FIG. 12 is an illustration of safety needle assembly 100 during a first portion of a syringe retraction stage, including a side view, a sectional view, and a detailed view thereof, where external housing 101 and AF 105 are concealed, providing a view of the internal components of assembly 100 at this stage. FIG. 13 is an illustration of safety needle assembly 100 during a second portion of a syringe retraction stage, including a side view, a sectional view, and a detailed view thereof, where external housing 101 and AF 105 are concealed, providing a view of the internal components of assembly 100 at this stage.

Figure 14:
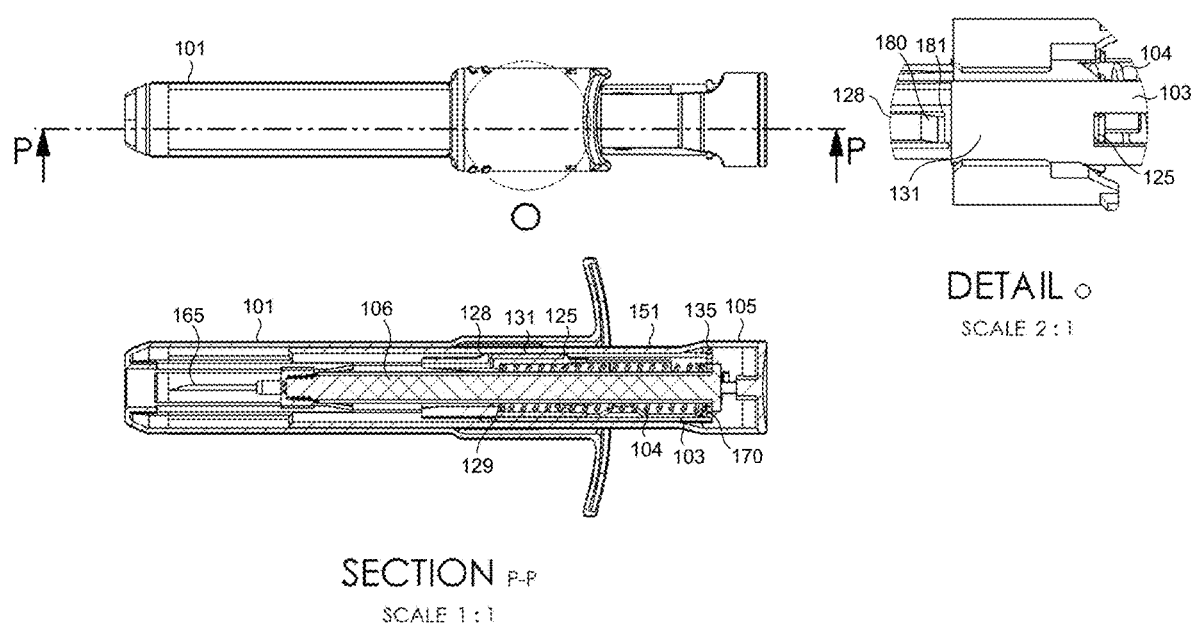
FIG. 14 is an illustration of a safety needle assembly in a discard state, constructed and operative in accordance with a first embodiment of the present invention, the illustration including a side views a sectional view and a detailed view of the safety needle assembly, where the external housing and activation fork are concealed from view.

After syringe 106 has been fully retracted such that needle 165 is completely positioned within EH 101 and/or IH 102, the distal end of extending arms 131 of ROS 103 are positioned between respective directing protrusions 125 and locking snaps 128 of IH 102. This places assembly 100 in a "safe discard state", as directing protrusions 125 prevents further proximal motion of ROS 103 and syringe 106, while locking snaps 128 prevents distal motion of ROS 103 and syringe 106. Furthermore, AF 105 is restricted from being distally pulled out of assembly 100 due to the alignment of AF guiding arms 151 relative to ROS 103 as the proximal end of AF guiding arms 151 has a smaller radius than that of notched flange 135. The user may then safely dispose of needle 165 and assembly 100 when in the safe discard state. FIG. 14 is an illustration of safety needle assembly 100 in a discard state, including side views, a sectional view, and a detailed view thereof, where external housing 101 and AF 105 are concealed, providing a view of the internal components of assembly 100 at this stage.

Safety needle assembly 100 may further include an indicator (not shown), configured to denote the progress of the injection process, and to signify that the injectant substance has been fully injected, such as by a visual indication, an audible indication and/or a tactile indication. For example, the indicator may be embodied by windows 111 of EH 101, which provides visibility of the progress of plunger stopper 116 during the injection. The indicator may further facilitate the user to continue to depress syringe plunger rod 161 all the way without prematurely terminating the applied force before the injection process has been fully carried out. For another example, the indicator may be a "click" sound that is audible by the user at the end of the injection process when ROS 103 disengages from guiding arms 151 of AF 105. The release of ROS 103 may also provide a tactile indication to the user, due to the corresponding release of BE 104 applying a proximal force through syringe 106 to the user pressing finger rest 162.

Figure 15:
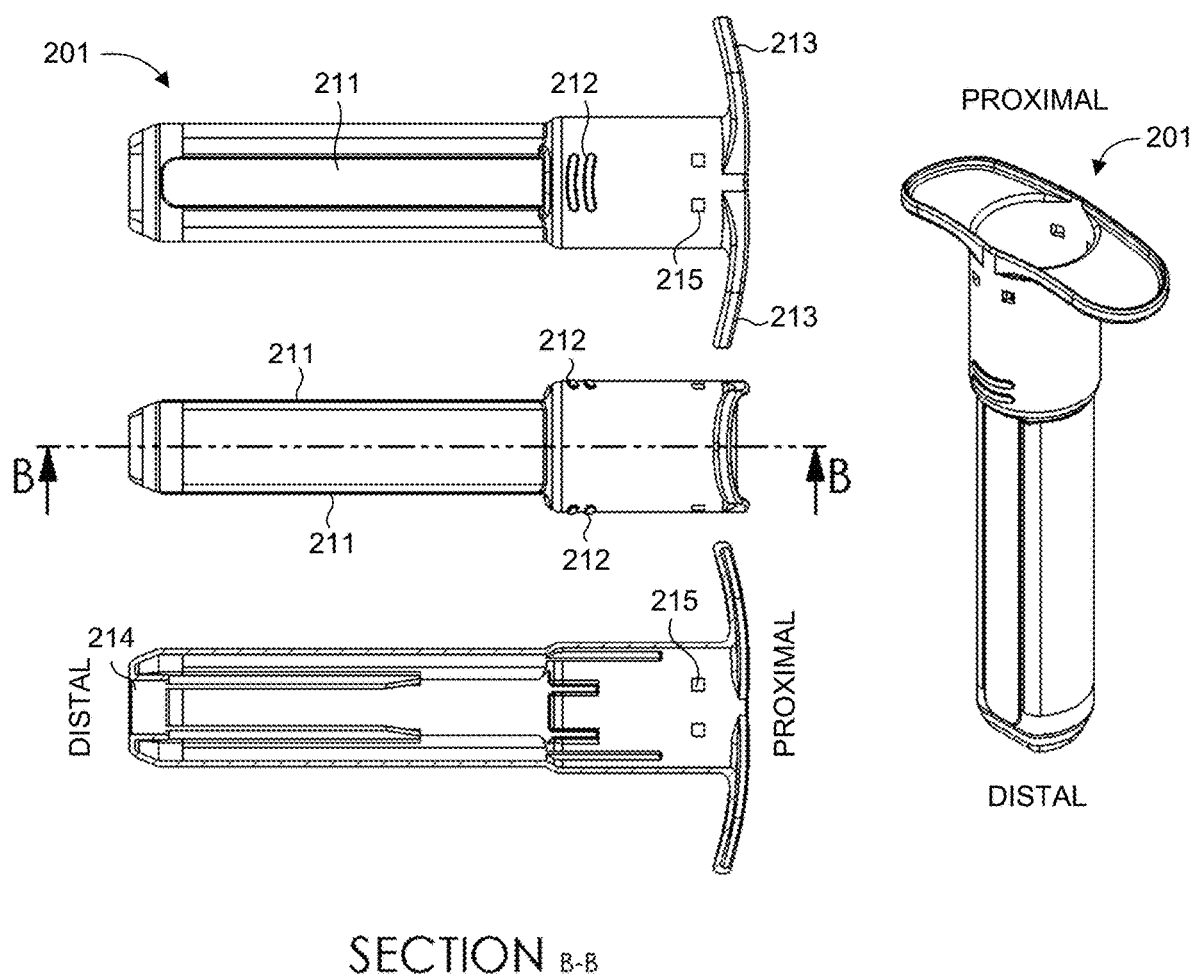
FIG. 15 is an illustration of an external housing for a safety needle assembly, constructed and operative in accordance with a second embodiment of the present invention, the illustration including a perspective view, orthogonal side views, and a sectional view of the housing.
Figure 16:
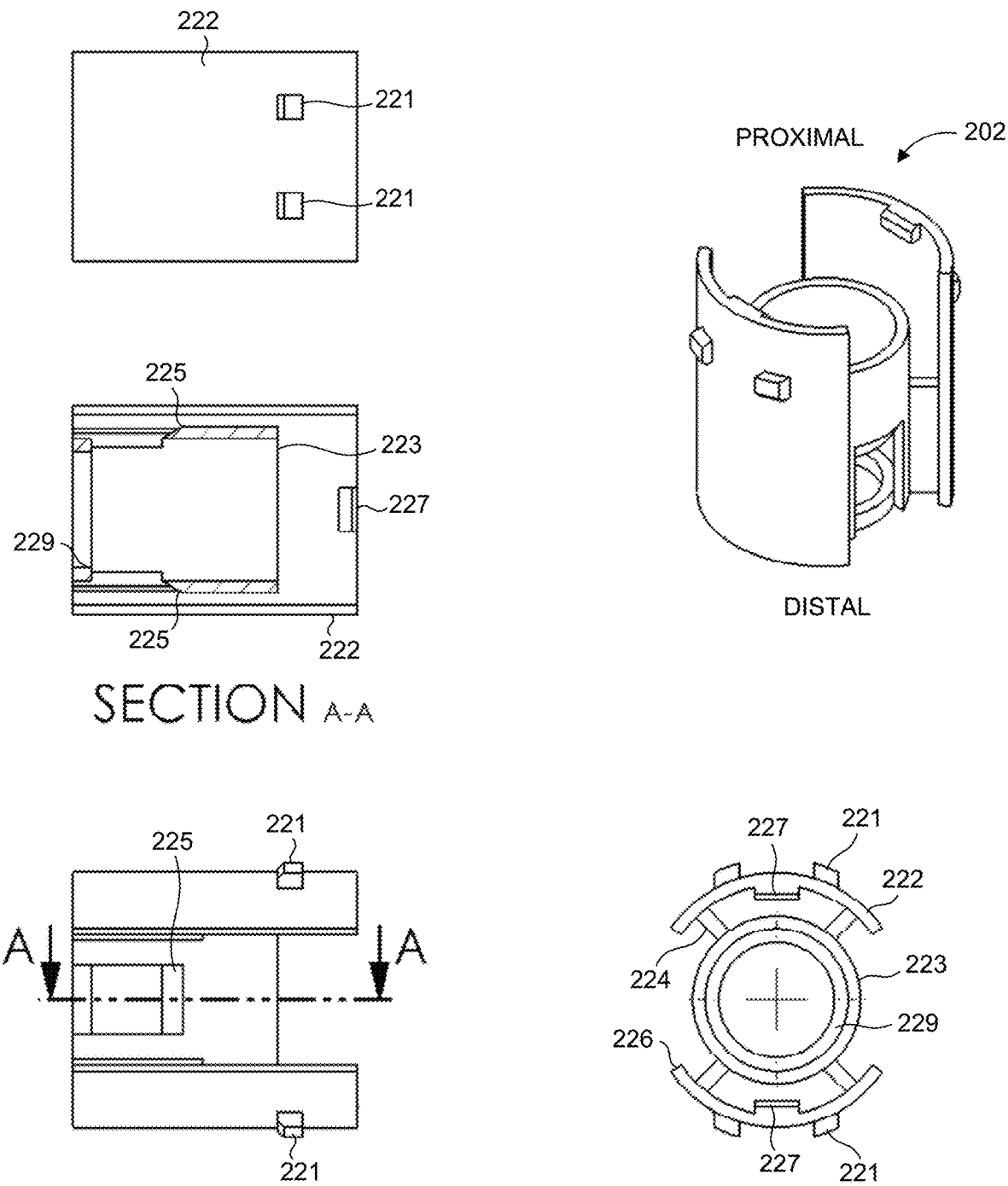
FIG. 16 is an illustration of an internal housing for a safety needle assembly, constructed and operative in accordance with a second embodiment of the present invention, the illustration including a perspective view, side and top views, and a sectional view of the internal housing.

Reference is now made to FIGS. 15 through 27, which collectively illustrate a safety needle assembly, generally referenced 200, according to a second embodiment of the present invention. Assembly 200 includes an external housing (EH) 201, an internal housing (IH) 202, a locking sleeve (LOS) 203, a biasing element (BE) 204, an activation fork (AF) 205, and a syringe 206. Assembly 200 has a distal end and a proximal end, which is depicted in FIG. 15 in the context of external housing 201, where the distal end faces away from the user holding assembly 200 and towards the injection site. Assembly 200 is also defined by a longitudinal axis, extending lengthwise along the assembly between the proximal and distal ends, where an "axial" direction corresponds to a direction parallel to the longitudinal axis (i.e., towards or away from the proximal or distal ends), whereas a "radial" direction corresponds to a direction orthogonal to the longitudinal axis, and extending radially therefrom.

External housing 201 of assembly 200 (illustrated in FIG. 15) is identical to external housing 101 of assembly 100 (illustrated in FIG. 1).

Internal housing 202 of assembly 200 (illustrated in FIG. 16) includes an inner tube 223 concentrically disposed within an outer tube 222, where inner tube 223 is affixed to outer tube 222 via a plurality of (e.g., four) radially extending connecting ribs 224. A base wall 229 is positioned within inner tube 223. Guiding ribs 226 are situated on opposite sides on the inner part of outer tube 222. IH 202 includes two pairs of short connecting protrusions 221, each pair extending radially outwards at the proximal end of outer tube 222 at a respective side thereof. IH 202 further includes a pair of stopping protrusions 227 extending radially inwards from the inner surface of outer tube 222 at the proximal end thereof. Inner tube 223 includes gripping slopes 225 on opposite sides thereof. Each gripping slope 225 is characterized by an outwardly sloping surface near the distal end of inner tube 223. Gripping slopes 225 are situated perpendicular to stopping protrusions 227.

It should be noted that the "external housing" and the "internal housing" can be considered two parts of a single component which can be collectively referred to as a "housing". Accordingly, external housing 201 and internal housing 202 are represented herein as two separated pieces or components for convenience of manufacturing considerations, but can alternatively can be manufactured as a single integral component using different manufacturing technologies.

Locking sleeve (LOS) 203 of assembly 200 (illustrated in FIG. 17) is a cylindrical tube with a hollow core and includes a pair of extending arms 231 extending distally from a flange wall 270 at the proximal end of LOS 203. The inner diameter and axial length of LOS 203 are larger than inner tube 223 of internal housing 202. LOS 203 further includes a pair of stopping protrusions 238 extending distally from flange wall 270 on opposite sides in between (and orthogonal to) extending arms 231. Stopping protrusion 238 is characterized by a narrow flat-edged flap extending distally from a wider base portion adjacent to flange wall 270, where the length of stopping protrusion 238 is slightly shorter than that of extending arm 231. Each extending arm 231 includes a gripping snap 232 at the proximal end of LOS 203. Gripping snap 232 has a radially inward facing slope 233 at the distal end thereof. Each extending arm 231 further includes a locking snap 235 positioned adjacent to and distally from the respective gripping snap 232. Locking snap 235 has a deflecting slope 237 at the distal end thereof, the deflecting slope 237 facing proximally and radially inwards. LOS 203 includes arcuate ridges 234 extending proximally from the edges of flange wall 270, proximate to gripping snaps 232 of extending arms 231. LOS 203 further includes a pair of holding snaps 236, which are short protrusions projecting proximally from the edges of flange wall 270 in between (and orthogonally to) ridges 234. It is noted that certain components of LOS 203 are described herein for exemplary purposes as being of a plurality, such as: two extending arms 231; two stopping protrusions 238; two gripping snaps 232 (i.e., one on each extending arm 231); two locking snaps 235 (i.e., one on each extending arm 231); and two holding snaps 236. However, LOS 203 may more generally be configured with any number of these respective components, such as for example, by including only one extending arm 231 (with a respective gripping snap 232 and respective locking snap 235); one stopping protrusions 238; and one holding snap 236, in an alternative embodiment. In a further alternative embodiment, LOS 203 may be configured with an outer diameter that is smaller than the inner diameter of outer tube 222 of IH 202. Correspondingly, gripping slopes 225 of IH 202 may be configured with an inwardly sloping surface at the distal end of outer tube 222 (i.e., rather than an outwardly sloping surface at the distal end of inner tube 223). Furthermore, gripping snap 232 of LOS 203 may be configured with a radially outward facing slope (i.e., rather than a radially inward facing slope), and locking snap 235 may be configured with a deflecting slope 237 facing proximally and radially outwards (i.e., rather than radially inwards) in such an embodiment.

The term "moving sleeve (MOS)" will be used herein to encompass both a rotating sleeve (ROS) 103 as in assembly 100 and a locking sleeve (LOS) 203 as in assembly 200, in accordance with embodiments of the present invention.

Biasing element 204 may be embodied, for example, by a compression spring, or more generally by any suitable device or mechanism configured to apply an axial biasing force against LOS 203 and IH 202.

Activation fork (AF) 205 of assembly 200 (illustrated in FIG. 18) is a cylindrical tube with a hollow core and includes a pair of arc-shaped guiding arms 251 extending distally from an end member 254 at the proximal end of AF 205. End member 254 is generally circular and "ring" shaped, i.e., with a hollow central portion, but may alternatively be a different shape or form, such as a filled (non-hollow) plate. Each guiding arm 251 includes an activation opening 252 at the proximal end adjacent to end member 254. Each guiding arm 251 further includes a locking opening 255 positioned distally from and adjacent to activation opening 252. It is noted that AF 205 may alternatively be configured with only a single guiding arm 251, or more generally may be configured with any number of guiding arms 251, but is described herein for exemplary purposes as including two guiding arms 251.

In accordance with an alternative embodiment, gripping snap 232 and locking snap 235 of LOS 203 may be integrated into a single unified snap. Correspondingly, activation opening 252 and locking opening 255 of AF 205 may be integrated into a single unified opening. In accordance with another alternative embodiment, locking snap 235 of LOS 203 may be incorporated into internal housing 202 while being positioned and functioning in a manner similar to locking snap 128 of assembly 100 (illustrated in FIG. 2), in which case locking opening 255 of AF 205 may be eliminated.

Syringe 206 of assembly 200 (illustrated in FIG. 19) is generally identical to syringe 106 of assembly 100 (illustrated in FIG. 5). Syringe 206 includes a syringe chamber 264, a syringe flange 263, a needle 265, a syringe plunger rod 261, a plunger stopper 266, and a finger rest 262. Syringe 206 does not include cut-outs (i.e., unlike the cutouts present on syringe 106 of assembly 100).

Figure 20:
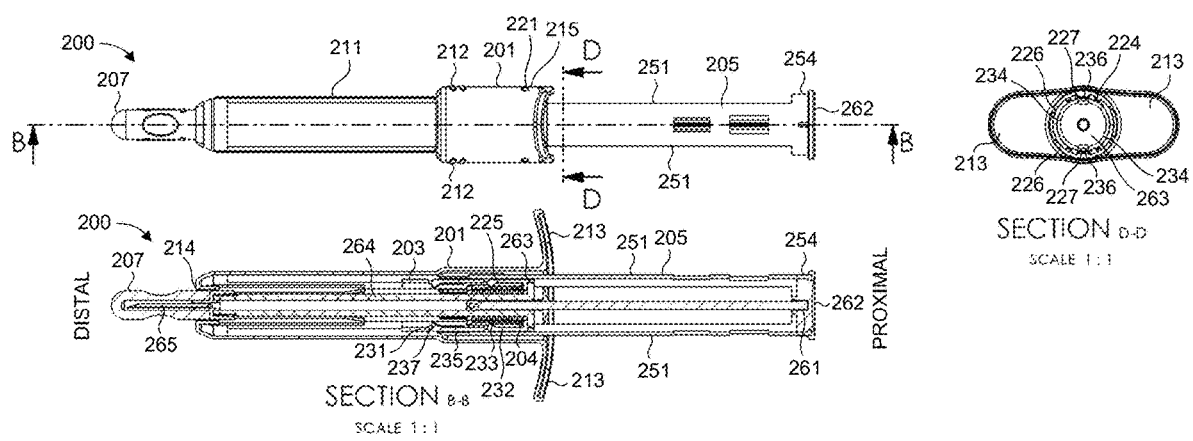
FIG. 20 is an illustration of a safety needle assembly in a storage state, constructed and operative in accordance with a second embodiment of the present invention, the illustration including a first side view, a corresponding side sectional view, and a top sectional view of the safety needle assembly.
Figure 21:
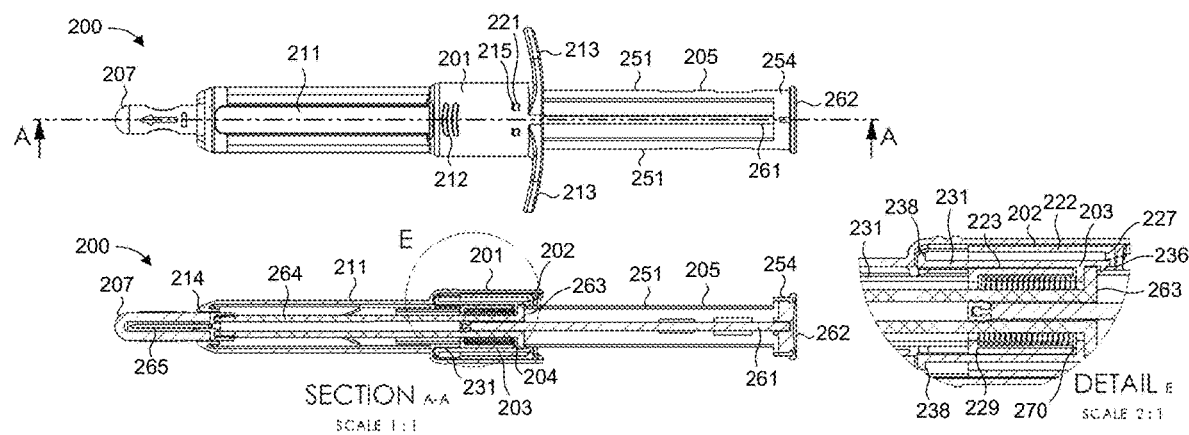
FIG. 21 is an illustration of a safety needle assembly in a storage state, constructed and operative in accordance with a second embodiment of the present invention, the illustration including a second side view, a corresponding sectional view, and a detailed view of the safety needle assembly.

FIGS. 20 and 21 provide different views of safety needle assembly 200 in a "storage state" or a "non-deployment state", representing the configuration of assembly 200 when not in use (i.e., before implementing an injection). IH 202 is concentrically arranged within EH 201 and is fixedly coupled to EH 201 by connecting protrusions 221 of IH 202 engaging with apertures 215 at the proximal end of EH 201. LOS 203 is also concentrically arranged within EH 201. In particular, LOS 203 is disposed between outer tube 222 and inner tube 223 of IH 202, where extending arms 231 extend through the distal end of IH 202, and where gripping snaps 232 are positioned such that the inward slope 233 of each gripping snap 232 is supported by gripping slope 225 of inner tube 223 of IH 202. Stopping protrusions 227 of IH 202 are aligned angularly with stopping protrusions 238 of LOS 203. BE 204 is disposed within IH 202, and supported at its distal end by base wall 229 of IH 202 and supported at its proximal end by flange wall 270 of LOS 203.

AF 205 is positioned between LOS 203 and outer tube 222 of IH 202. In particular, end member 254 at the proximal end of AF 205 is coupled to finger rest 262 of syringe 206, while guiding arms 251 of AF 205 are guided by guiding ribs 226 on the inner part of outer tube 222. The distal end of guiding arms 251 are positioned between gripping snap 232 of LOS 203 and outer tube 222 of IH 202. Syringe 206 is positioned within inner tube 223 of IH 202 and coupled to LOS 203 by holding snaps 236. Syringe 206 is concentric to LOS 203 by ridges 234 on flange wall 270.

BE 204 applies an axial force (e.g., a spring force) that biases LOS 203 to the proximal direction. Gripping snaps 232 of LOS 203 are compelled by gripping slope 225 to deflect radially outwards when LOS 203 is biased to the proximal direction. When assembly 200 is in a storage state, guiding arms 251 of AF 205 prevents gripping snaps 232 from deflecting radially outwards, which in turn prevents LOS 203 from moving proximally. Syringe 206 is rotatable and axially movable but is prevented from axial movement when in storage position by holding snaps 236 which locks syringe flange 263 axially relative to LOS 203. When assembly 200 is in a storage state, syringe needle 265 extends at least partially through distal opening 214 and is encased by a needle guard 207 (analogous to needle guard 107 of assembly 100).

Figure 22:
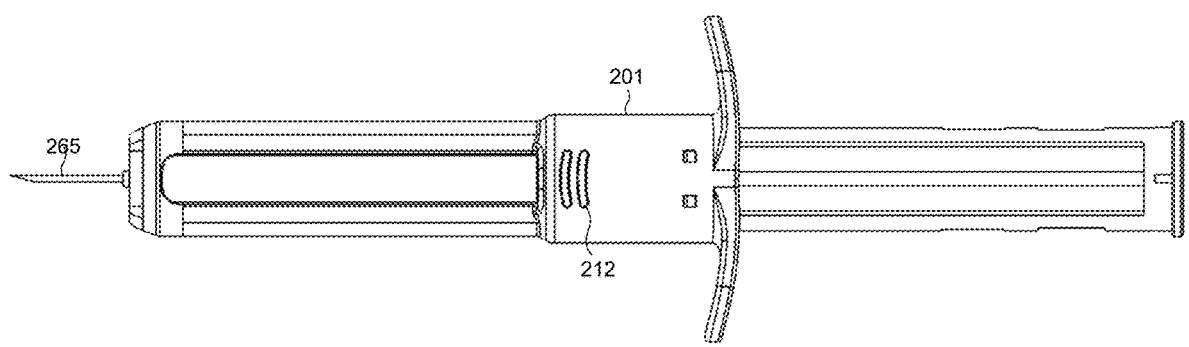
FIG. 22 is a side view illustration of a safety needle assembly during a needle insertion stage, operative in accordance with a second embodiment of the present invention.
Figure 23:
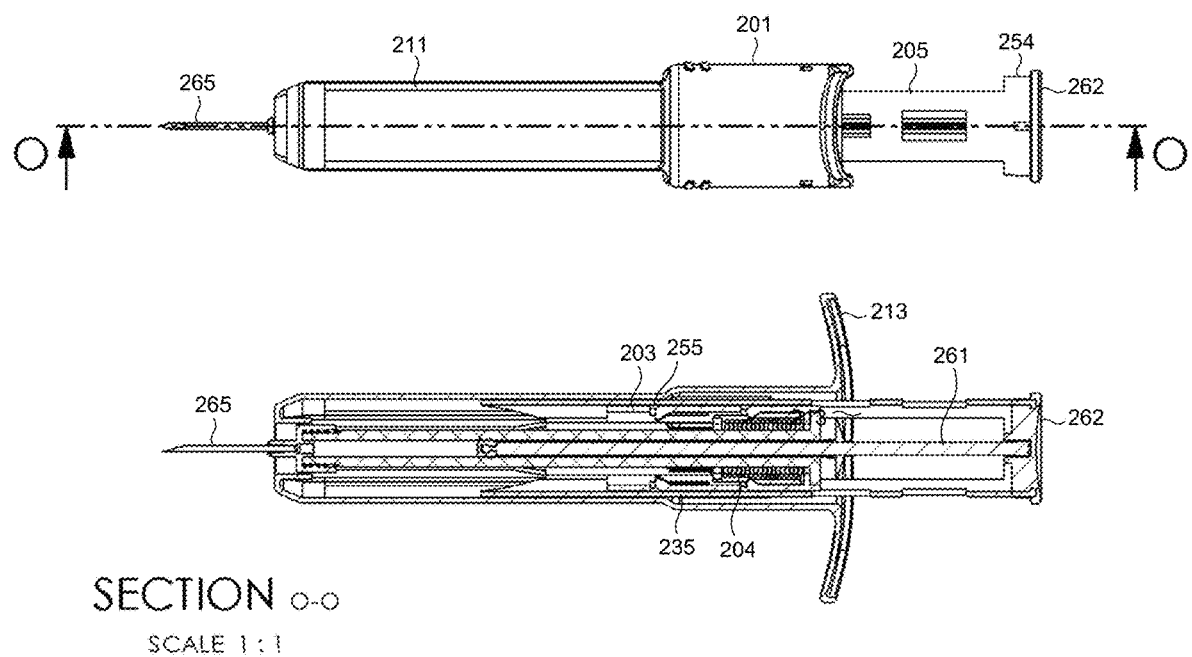
FIG. 23 is a side view illustration of a safety needle assembly during an injection stage, operative in accordance with a second embodiment of the present invention.

To deploy assembly 200 for performing an injection, a user (e.g., a medical clinician) holds assembly 200, preferably via grip 212, and removes needle guard 207, such as by pulling needle guard in the 207 distal direction, to expose needle 265. The user inserts the exposed distal end of needle 265 into an injection site (e.g., a body region of a patient to be injected). FIG. 22 is a side view illustration of safety needle assembly 200 during a needle insertion stage. After needle 265 has been inserted into the injection site, the user presses syringe finger rest 262 which pushes plunger rod 261 in the distal direction together with AF 205. The distal advancement of plunger rod 261 mutually advances plunger stopper 266 within syringe chamber 264, which propels the injectant substance distally within chamber 264 to pass through the distal aperture of needle 265 and enter the injection site. The progress of plunger rod 261 and plunger stopper 266 along chamber 264 and the passage of the injectant substance can be viewed through windows 211. FIG. 23 is a side view illustration of safety needle assembly 200 during an injection stage.

Figure 24:
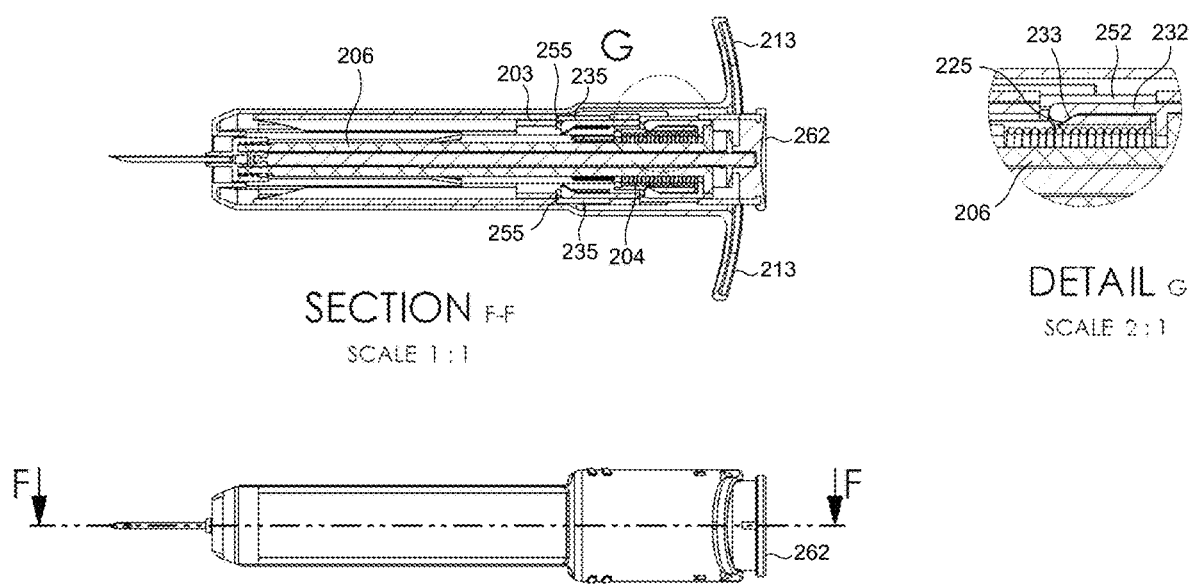
FIG. 24 is an illustration of a safety needle assembly during the end of the injection stage, operative in accordance with a second embodiment of the present invention, the illustration including a side view, a corresponding sectional view, and a detailed view of the safety needle assembly.

The distal advancement of syringe plunger rod 261 continues until activation openings 252 of guiding arms 251 of AF 205 aligns with gripping snaps 232 of LOS 203, and locking openings 255 of guiding arms 251 of AF 205 aligns with locking snaps 235 of LOS 203. This allows gripping snaps 232 and locking snaps 235 to deflect radially outwards through the respective openings (since they are no longer prevented from such deflection by guiding arms 251), causing axial movement of LOS 203 to the proximal direction. It is noted that gripping snaps 232 are slightly wider in size than locking openings 255, such that when locking openings 255 pass gripping snaps 232 as syringe plunger rod 261 advances distally, gripping snaps 232 will be unable to deflect through locking openings 255 and LOS 203 will remain in a non-activated position. Syringe 206 and LOS 203 are held in place by the force applied by the user fingers pressing (distally) against finger rest 262 at the end of syringe plunger rod 261. FIG. 24 is an illustration of safety needle assembly 200 during the end of an injection stage, including a side view, a corresponding sectional view and a detailed view, showing the respective alignments of LOS 203, AF 205 and syringe 206 at this stage.

Safety needle assembly 200 provides a smooth and substantially constant opposing resistive force during the advancement of syringe plunger rod 261, without an abrupt force increase needed to activate the safety retraction mechanism as in conventional (partially automated) safety syringes. The smooth and substantially constant resistance compels the user to fully depress syringe plunger rod 261 (by continuing to press against finger rest 262) without prematurely terminating the distal advancement of plunger rod 261 along syringe chamber 264 before the injection process has been fully carried out and the safety mechanism has been activated. Reference is made again to FIGS. 28, 29 and 30 and the relevant description provided hereinabove.

Figure 25:
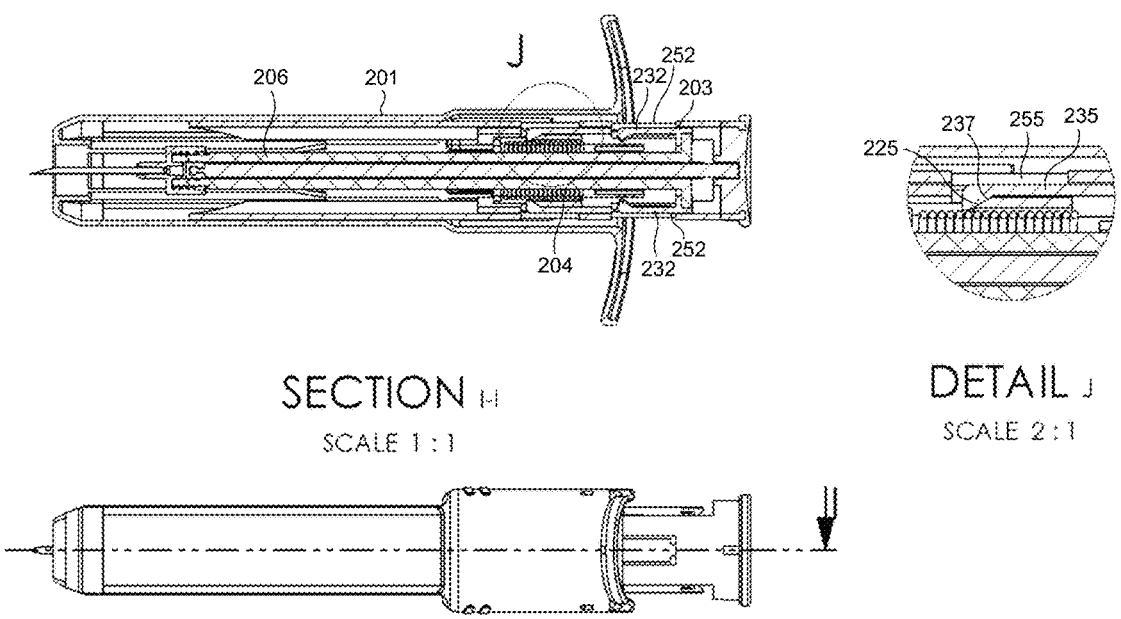
FIG. 25 is an illustration of a safety needle assembly during a syringe retraction stage, operative in accordance with a second embodiment of the present invention, the illustration including a side view, a sectional view, and a detailed view of the safety needle assembly.

After the injection process is completed, the user releases the distal force applied to syringe plunger rod 261 by stopping to press finger rest 262, which reduces the axial force applied to syringe 206 and LOS 203. This allows the biasing force of BE 204 to move LOS 203 axially to the proximal direction. Gripping snaps 232 are deflected radially outward through activation openings 252 until gripping snaps 232 pass the proximal end of inner tube 223 and return to their relaxed (non-deflected) position. At a certain proximal advancement of LOS 203, locking snaps 235 engage gripping slopes 225 of IH 202 and deflect radially outward through locking openings 255. The proximal motion of LOS 203 continues until stopping protrusions 238 of LOS 203 engage stopping protrusions 227 of IH 202, and locking snaps 235 pass the proximal end of inner tube 223 and return to their relaxed (non-deflected) position, restricting further LOS 203 movement. The proximal axial movement of LOS 203 is accompanied by the mutual proximal axial movement of syringe 206, which in turn causes syringe needle 265 to retract into the assembly housing (external housing 201 and/or internal housing 202). FIG. 25 is an illustration of safety needle assembly 200 during the syringe retraction stage, including a side view, a sectional view, and a detailed view thereof.

Figure 26:
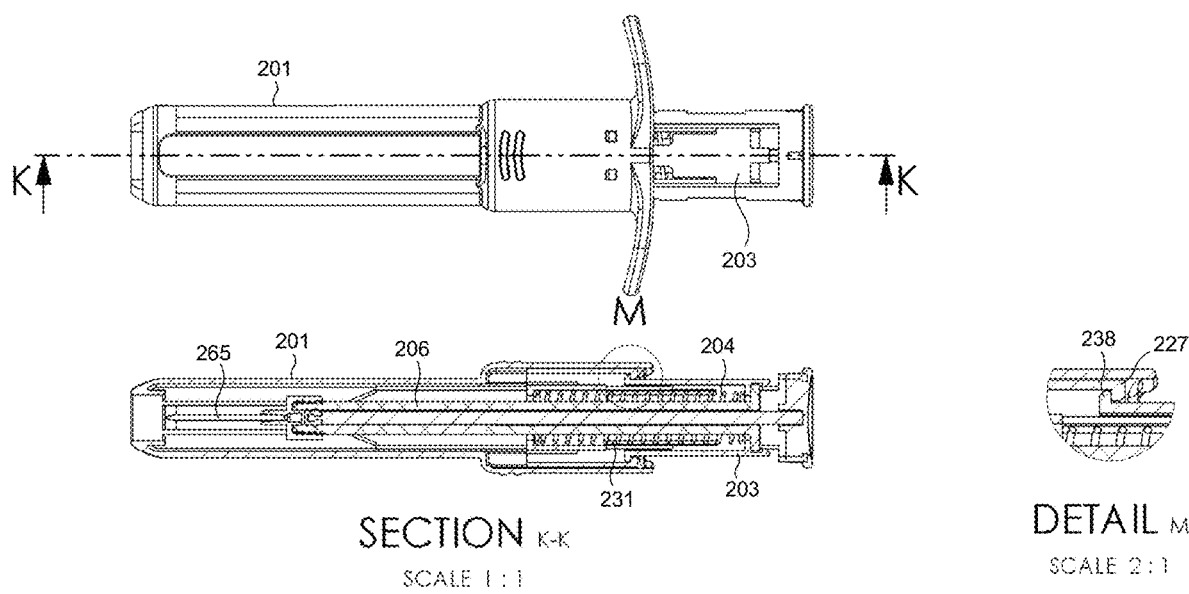
FIG. 26 is an illustration of a safety needle assembly in a discard state, constructed and operative in accordance with a second embodiment of the present invention, the illustration including a first side view, a corresponding sectional view, and a detailed view of the safety needle assembly.
Figure 27:
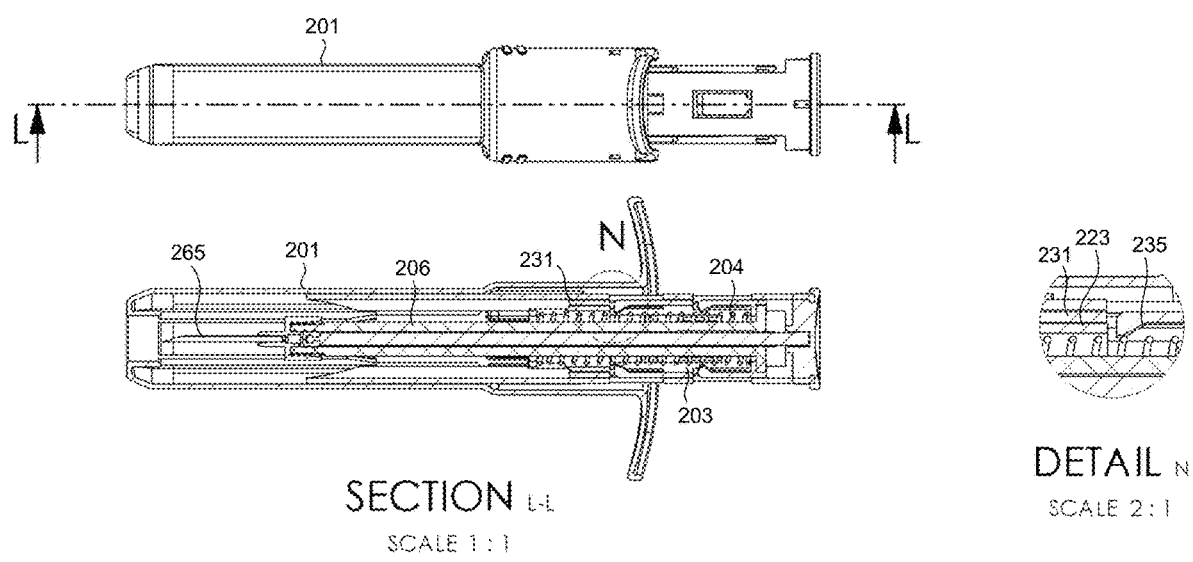
FIG. 27 is an illustration of a safety needle assembly in a discard position, constructed and operative in accordance with a second embodiment of the present invention, the illustration including a second side view, a corresponding sectional view, and a detailed view of the safety needle assembly.

After syringe 206 has been fully retracted such that needle 265 is completely positioned within EH 201 and/or IH 202, stopping protrusions 227 of IH 202 prevents further proximal motion of LOS 203 and syringe 206 when engaged with stopping protrusions 238, while locking snaps 235 prevents distal motion of LOS 203 and syringe 206. This places assembly 200 in a "safe discard state", allowing the user to safely dispose of needle 265 and assembly 200. FIGS. 26 and 27 are illustration of safety needle assembly 200 in a discard state, including respective side views, sectional views, and detailed views thereof.

Figure 31:
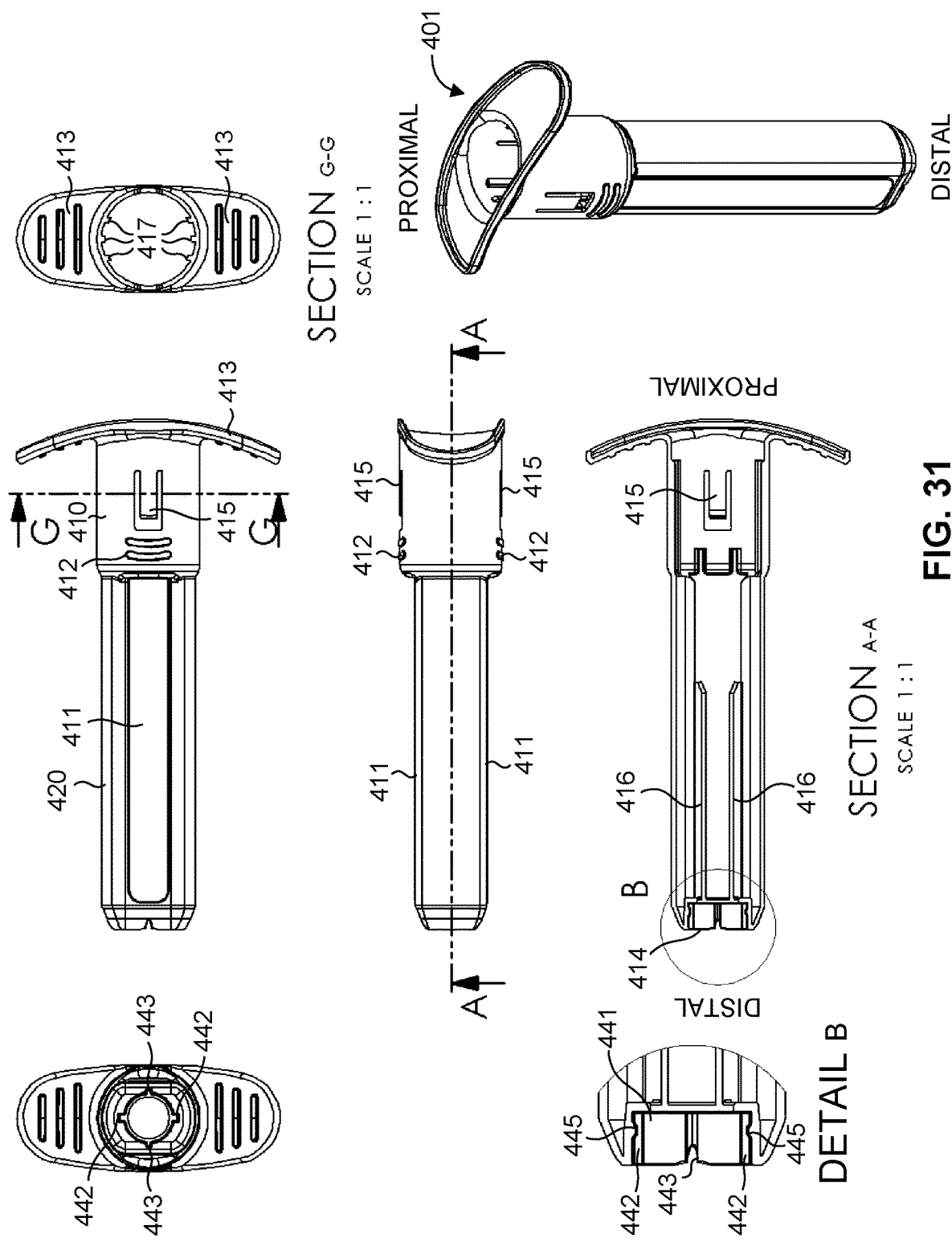
FIG. 31 is an illustration of an external housing for a safety needle assembly, constructed and operative in accordance with a third embodiment of the present invention, the illustration including a perspective view, orthographic views, sectional views, and a detailed view of the housing.
Figure 32:
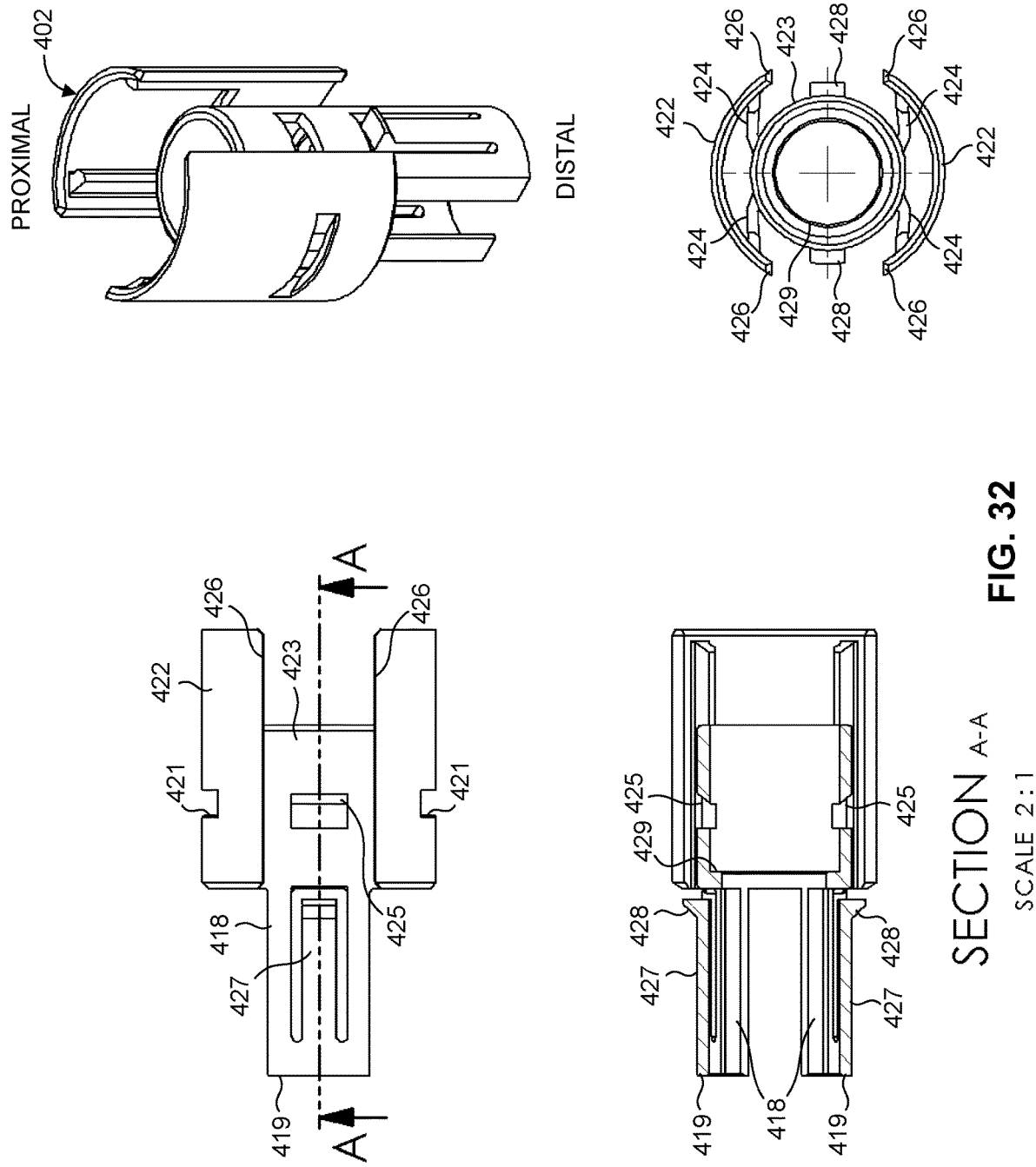
FIG. 32 is an illustration of an internal housing for a safety needle assembly, constructed and operative in accordance with a third embodiment of the present invention, the illustration including a perspective view, orthographic side and top views, and a sectional view of the internal housing.
Figure 33:
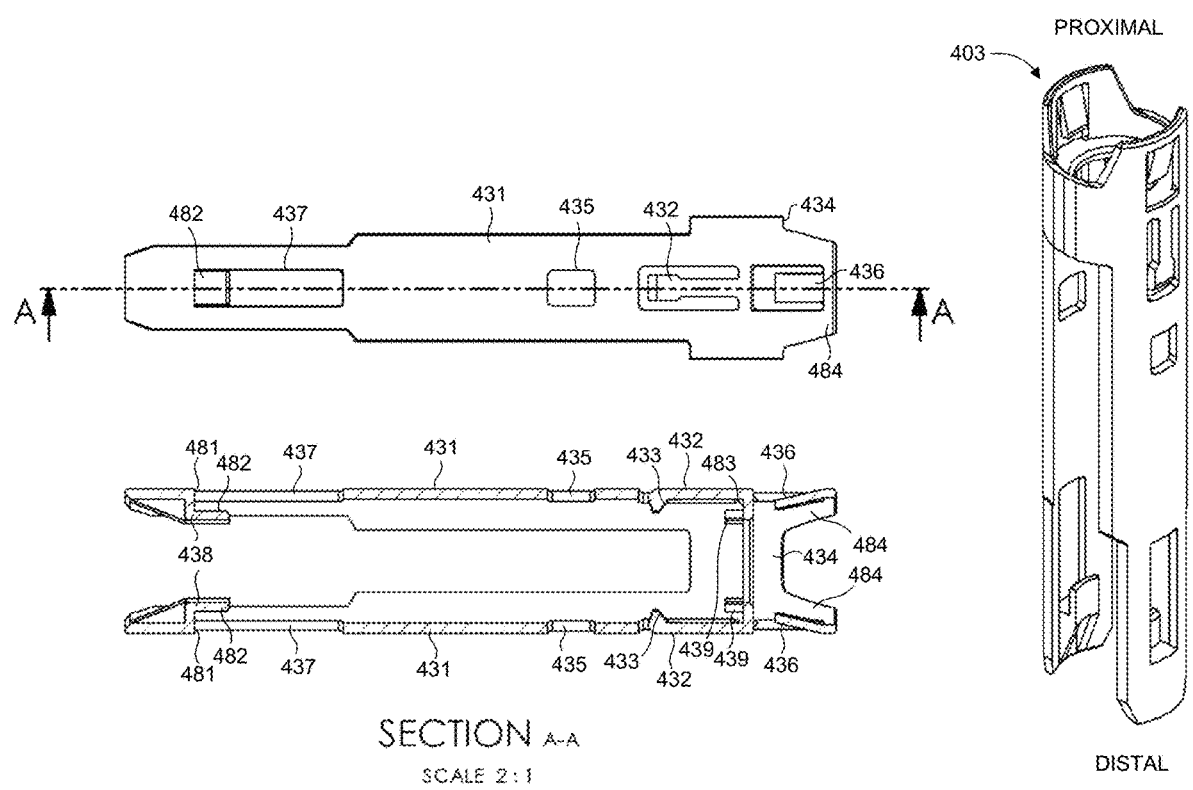
FIG. 33 is an illustration of a locking sleeve for a safety needle assembly, constructed and operative in accordance with a third embodiment of the present invention, the illustration including a perspective view, an orthographic side view, and a sectional view of the locking sleeve.
Figure 34:
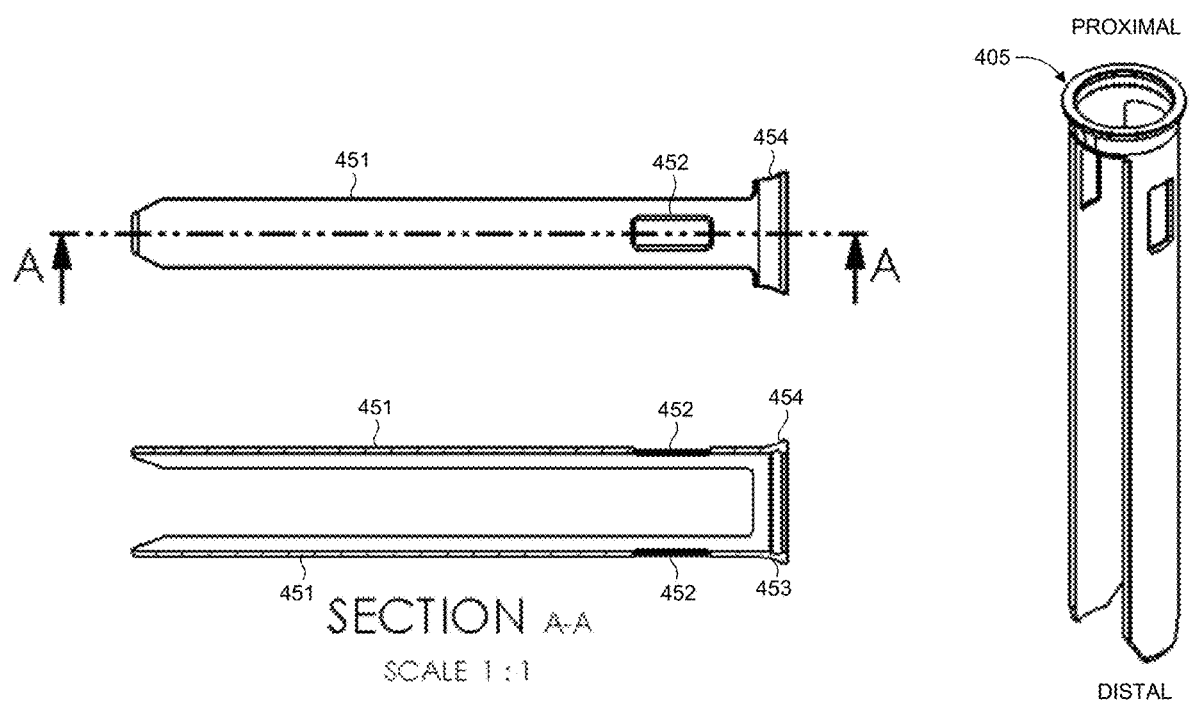
FIG. 34 is an illustration of an activation fork for a safety needle assembly, constructed and operative in accordance with a third embodiment of the present invention, the illustration including a perspective view, an orthographic side view, and a sectional view of the activation fork.
Figure 35:
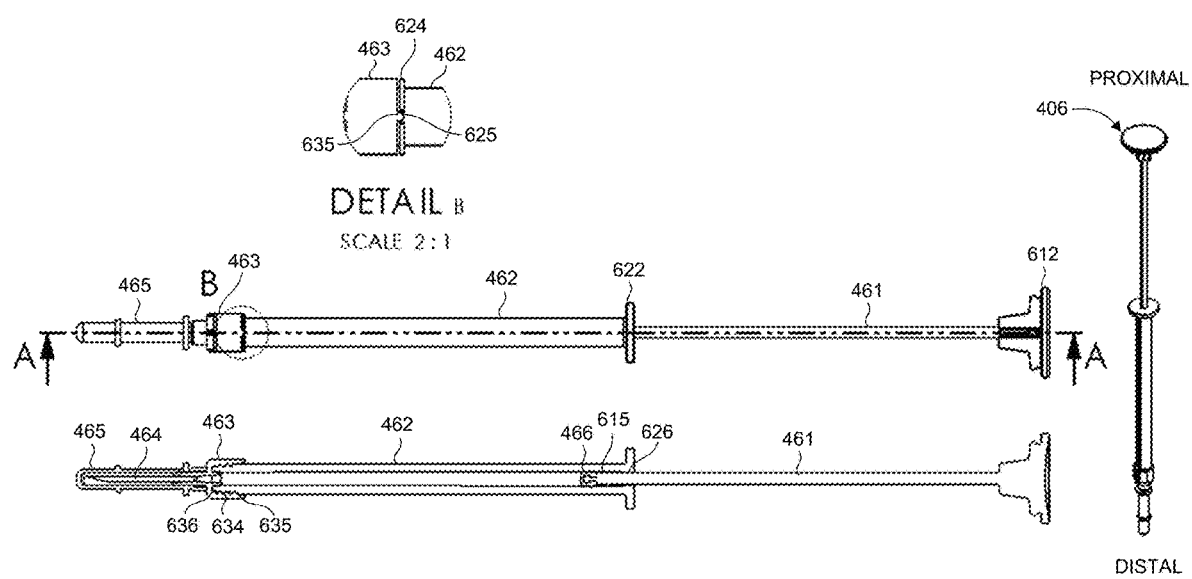
FIG. 35 is an illustration of a syringe of a safety needle assembly, constructed and operative in accordance with a third embodiment of the present invention, the illustration including a perspective view, an orthographic side view, a sectional view, and a detailed view of the syringe.

Reference is now made to FIGS. 31 through 47, which collectively illustrate a safety needle assembly, generally referenced 400, according to a third embodiment of the present invention. Assembly 400 includes an external housing (EH) 401, an internal housing (IH) 402, a locking sleeve (LOS) 403, a biasing element (BE) 404, an activation fork (AF) 405, a syringe 406, and an outer cap 407. Assembly 400 has a distal end and a proximal end, which is depicted in FIG. 31 in the context of external housing 401, where the distal end faces away from the user holding assembly 400 and towards the injection site. Assembly 400 is also defined by a longitudinal axis, extending lengthwise along the assembly between the proximal and distal ends, where an "axial" direction corresponds to a direction parallel to the longitudinal axis (i.e., towards or away from the proximal or distal ends), whereas a "radial" direction corresponds to a direction orthogonal to the longitudinal axis, and extending radially therefrom.

External housing (EH) 401 of assembly 400 (illustrated in FIG. 31) is generally analogous to EH 101 of assembly 100 (illustrated in FIG. 1). EH 201 of assembly 200 (illustrated in FIG. 15), but is adapted to engage with IH 402 via a pair of snaps 415 as described hereinbelow. EH 401 is configured to at least partially encase the other components of assembly 400. EH 401 includes a proximal EH body portion 410 which is substantially cylindrical shaped (i.e., having a substantially circular radial cross-section), and a distal EH body portion 420 which is tubular having a substantially rectangular radial cross-section with a pair of arc-shaped edges. EH 401 includes at least one grip 412 disposed at a proximal end thereof for enabling a user to hold or grip assembly 400 and facilitate the needle insertion. EH 401 further includes a flange 413, consisting of opposing ledges projecting radially outward at the proximal end of EH 401, for positioning the fingers of a user when depressing the syringe plunger during an injection. A pair of windows 411 are arranged lengthwise along the distal EH body portion 420 between grip 412 and the distal end of EH 401, to allow observation of the injectant substance throughout the injection process. EH 401 includes a pair of snaps 415 disposed on opposite sides of proximal EH body portion 410, to hold IH 402 in place. EH 401 includes a distal opening 414, through which the syringe needle passes during an injection. EH 401 further includes a plurality of distal ribs 416, arranged on the inner surface of distal EH body portion 420, and configured to radially support syringe hub 463 (as will be discussed further hereinbelow with reference to FIG. 35). A plurality of support ribs 417 protrude radially from a proximal opening at the proximal end of EH 401, and is configured to support guiding arms of activation fork 415 (as will be discussed further hereinbelow with reference to FIG. 34) and to prevent rotation of IH 402 within EH 401. The distal end of EH 401 is characterized by a distal EH tube 441 having a pair of thick slots 442 and a pair of thin slots 443 extending longitudinally along the outer circumferential surface of distal EH tube 441 and opposingly disposed. In particular, thick slots 442 are disposed symmetrically on opposing sides of distal EH tube 441, while thin slots 443 are disposed symmetrically on opposing sides in between thick slots 442. A respective thick slot indentation 445 extends radially inward from the proximal end of each thick slot 442, and is configured to engage a corresponding protrusion 475 of outer cap 407 (as will be discussed further hereinbelow with reference to FIG. 37).

Internal housing (IH) 402 of assembly 400 (illustrated in FIG. 32) is generally analogous to IH 102 of assembly 100 (illustrated in FIG. 2). IH 402 includes an inner tube 423 concentrically disposed within an outer tube 422, where inner tube 423 is affixed to outer tube 422 via a plurality of (e.g., four) radially extending connecting ribs 424. A base wall 429 is positioned within inner tube 423. Guiding ribs 426 are situated on opposite sides on the inner part of outer tube 422. IH 402 further includes a pair of locking snaps 427, located distally of outer tube 422 on a distally extending portion 418 of inner tube 423, and extending axially on opposite sides. IH 402 is characterized by a distal end 419. Each locking snap 427 includes a locking tooth 428 at a proximal end thereof. Locking tooth 428 may be characterized by a triangular protrusion extending radially outwards from the respective locking snap 427. When assembly 400 is in a storage position, each locking tooth 428 is positioned within a first locking window 435 of arms 431 of locking sleeve 403 (as will be described further hereinbelow with reference to FIG. 33). A pair of openings 421 are located on opposing sides of outer tube 422. IH 402 is positioned within proximal EH body portion 410 of EH 401. In particular, snaps on proximal EH body portion 410 engage with respective IH openings 421 of outer tube 422, so as to couple IH 402 to EH 401. Gripping slopes 425 are located on opposing sides of inner tube 423, where each gripping slope 425 is characterized by an outwardly sloping surface near the distal end of inner tube 423. It is noted that IH 402 does not include connecting protrusions or stopping protrusions, in contrast to IH 202 of assembly 200.

It is further noted that the "external housing" and the "internal housing" can be considered two parts of a single component which can be collectively referred to as a "housing". Accordingly, external housing 401 and internal housing 402 are represented herein as two separated pieces or components for convenience of manufacturing considerations, but can alternatively can be manufactured as a single integral component using different manufacturing technologies.

Figure 17:
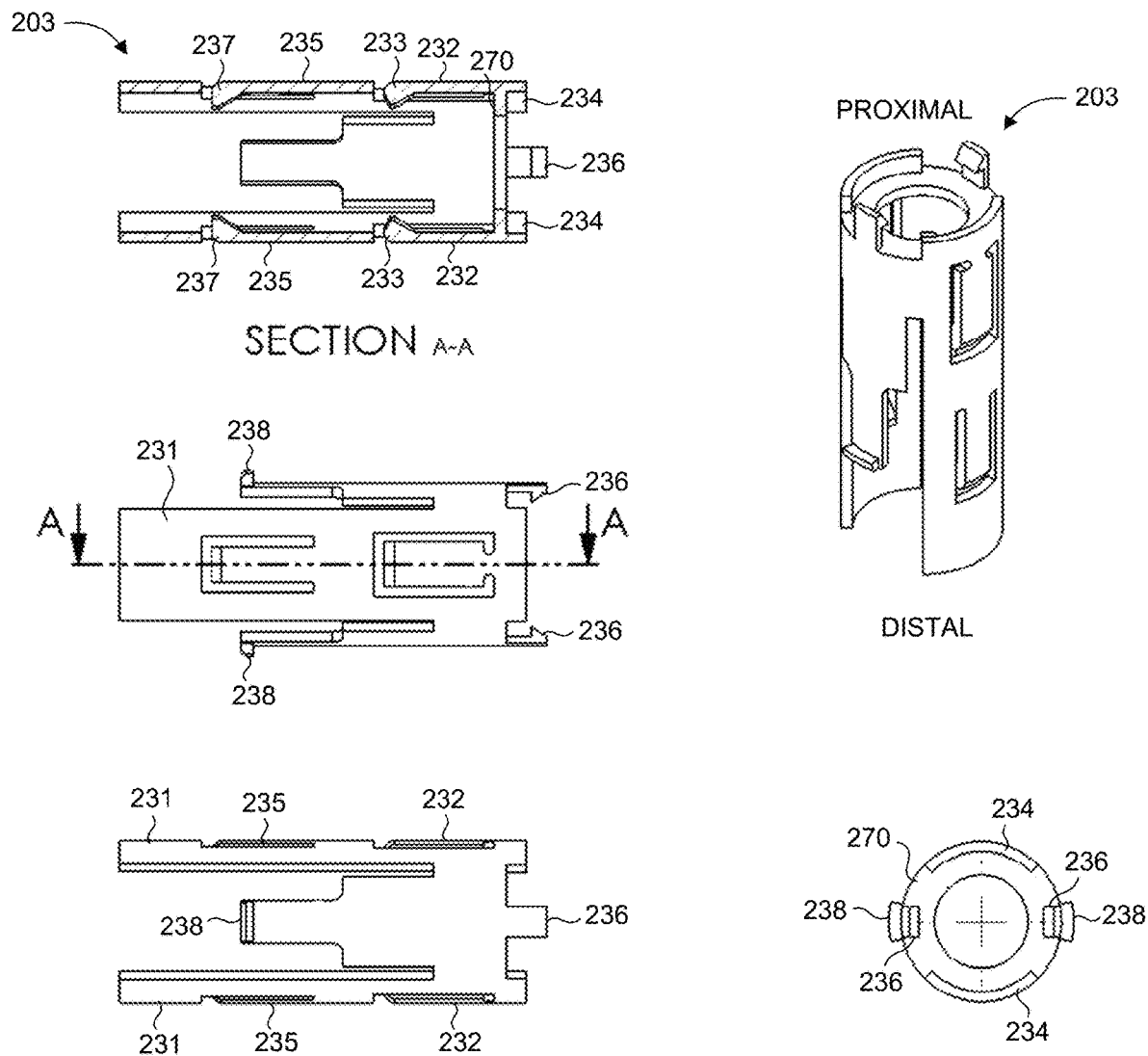
FIG. 17 is an illustration of a locking sleeve for a safety needle assembly, constructed and operative in accordance with a second embodiment of the present invention, the illustration including a perspective view, side and top views, and a sectional view of the locking sleeve.

Locking sleeve (LOS) 403 of assembly 400 (illustrated in FIG. 33) is similar to LOS 203 of assembly 200 (illustrated in FIG. 17). LOS 403 is tubular shaped with a hollow cylindrical body having an inner diameter and axial length larger than inner tube 423 of IH 402. LOS 403 includes a pair of extending arms 431 extending distally from a cylindrical wall 434 at the proximal end of LOS 403. Each extending arm 431 includes a gripping snap 432 at the proximal end of LOS 403. Gripping snap 432 has a radially inward facing slope 433 at the distal end thereof. Each extending arm 431 further includes a first locking window 435 positioned adjacent to and distally of the respective gripping snap 432, and a second locking window 437 positioned distally of first locking window 435 at the distal end of extending arm 431. Locking windows 435, 437 are openings extending through the respective extending arms 431 and configured to accommodate the locking tooth 428 and locking snap 427 of IH 402 when assembly 400 is in a storage position or a discard state. A pair of holding snaps 436 are positioned on cylindrical wall 434, projecting distally from opposing bridge portions 484 connecting the arcuate ridges of cylindrical wall 434. A stopping protrusion 438 is positioned at the distal end of each extending arm 431 adjacent to the respective second locking window 437. Stopping protrusion 438 faces radially inwards and includes a proximally facing ridge 481 and an axially parallel wall 482. LOS 403 is fitted over inner tube 423 of IH 402 when assembly 400 is in a storage position, such that extending arms 431 extend pass the distal end of IH 402 and are positioned between connecting ribs 424, and such that slope 433 of a respective gripping snap 432 is engaged with a corresponding gripping slope 425 of inner tube 423. Furthermore when assembly 400 is in a storage position, each locking tooth 428 of IH 402 is positioned within a respective first locking window 435 of LOS 403.

While certain components of LOS 403 are described for exemplary purposes as being of a plurality, LOS 403 may more generally be configured with any number of these respective components. LOS 403 may alternatively be configured with an outer diameter smaller than the inner diameter of outer tube 422 of IH 402. Correspondingly, gripping slopes 425 of IH 402 may be configured with an inwardly sloping surface at the distal end of outer tube 422 (i.e., rather than an outwardly sloping surface at the distal end of inner tube 423). Furthermore, gripping snap 432 of LOS 403 may be configured with a radially outward facing slope (i.e., rather than a radially inward facing slope 433). The term "moving sleeve (MOS)" as used herein further encompasses a locking sleeve (LOS) 403 in accordance with embodiments of the present invention.

Biasing element (BE) 404 (shown for example in FIGS. 38 and 39) may be embodied by a compression spring, or more generally by any suitable device or mechanism configured to apply an axial biasing force against LOS 403 and IH 402.

Figure 18:
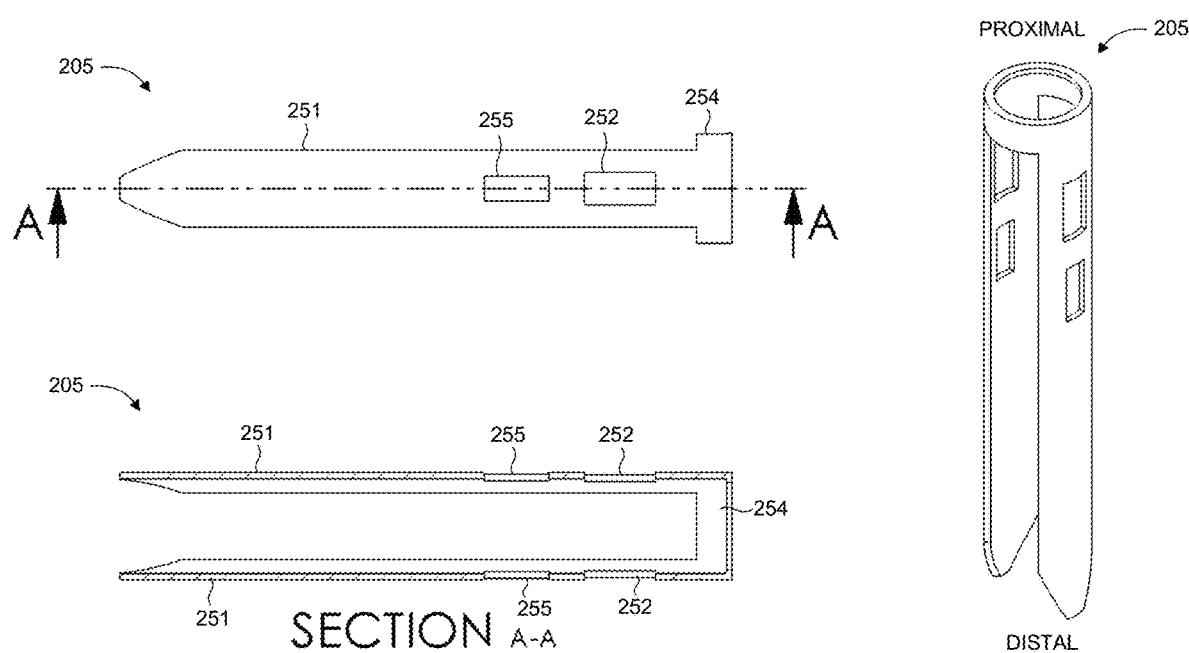
FIG. 18 is an illustration of an activation fork for a safety needle assembly, constructed and operative in accordance with a second embodiment of the present invention, the illustration including a perspective view, a side view, and a sectional view of the activation fork.
Figure 19:
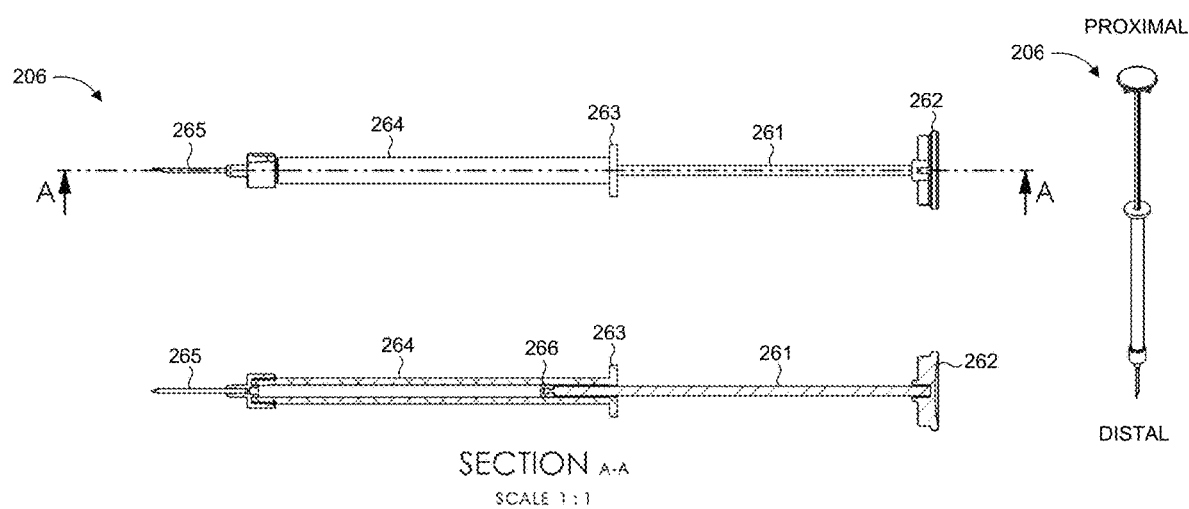
FIG. 19 is an illustration of a syringe of a safety needle assembly, constructed and operative in accordance with a second embodiment of the present invention, the illustration including a perspective view, a side view, and a sectional view of the syringe.

Activation fork (AF) 405 of assembly 400 (illustrated in FIG. 34) is similar to AF 205 of assembly 200 (illustrated in FIG. 18). AF 405 is tubular shaped with a hollow cylindrical body and includes a pair of arc-shaped guiding arms 451 extending distally from an end member 454 at the proximal end of AF 405. End member 454 is generally circular and ring-shaped (i.e., having a hollow central core), but may be an alternative shape or form (e.g., such as a filled non-hollow plate). Each guiding arm 451 includes an activation opening 452 at the proximal end adjacent to end member 454. End member 454 includes a groove 453, such as a circular groove, on the inner surface thereof. It is noted that AF 405 does not include locking openings on each guiding arm, in contrast to AF 205 of assembly 200. While certain components of AF 405 are described for exemplary purposes as being of a plurality, AF 405 may more generally be configured with any number of these respective components (e.g., having fewer or greater than two guiding arms 451).

Syringe 406 of assembly 400 (illustrated in FIG. 35) is similar to syringe 206 of assembly 200 (illustrated in FIG. 19) and syringe 106 of assembly 100 (illustrated in FIG. 5). Syringe 406 includes a syringe chamber 462, a syringe plunger rod 461, a syringe hub 463, a needle 464, a needle guard 465, and a plunger stopper 466. Syringe chamber 462 has a hollow cylindrical body with a chamber flange 622 at its proximal end. Plunger rod 461 is a cylindrical rod positioned concentrically within the hollow body of syringe chamber 462 with a finger rest 612 at its proximal end. The distal end of plunger rod 461 is coupled to plunger stopper 466, which is located within the hollow body of syringe chamber 462 so as to seal syringe chamber 462 from its proximal end. Needle 464 extends distally from the distal opening of syringe hub 463 at the distal end of syringe chamber 462, and is covered by needle guard 465 when assembly 400 is not in use. Plunger rod 461 is longitudinally advanceable within syringe chamber 462, such that when plunger rod 461 is compelled in a distal direction, such as by pressing against finger rest 612, an injectant substance contained within syringe chamber 462 is propelled distally by plunger stopper 466 through needle 464.

Syringe hub 463 includes a proximal hollow body portion 631 and a distal hollow body portion 632. A female screw 634 on the inner surface of proximal hollow body portion 631 is screwed around a male screw 623 of syringe chamber 462, thus engaging syringe hub 463 to syringe chamber 462. Syringe hub 463 further includes an internal sleeve 636 which engages the inner side of the hollow cylindrical body of syringe chamber 462 in a manner that seals the two against each other. Needle 464 is contained within distal hollow body portion 632 of syringe hub 463. Syringe hub 463 further includes two hub teeth 635 located on the proximal end thereof. When syringe hub 463 is engaged to syringe chamber 462, hub teeth 635 are positioned within notches 625 of a ring 624 of syringe chamber 462, so as to prevent hub 463 from being unscrewed from syringe chamber 462.

Figure 36:
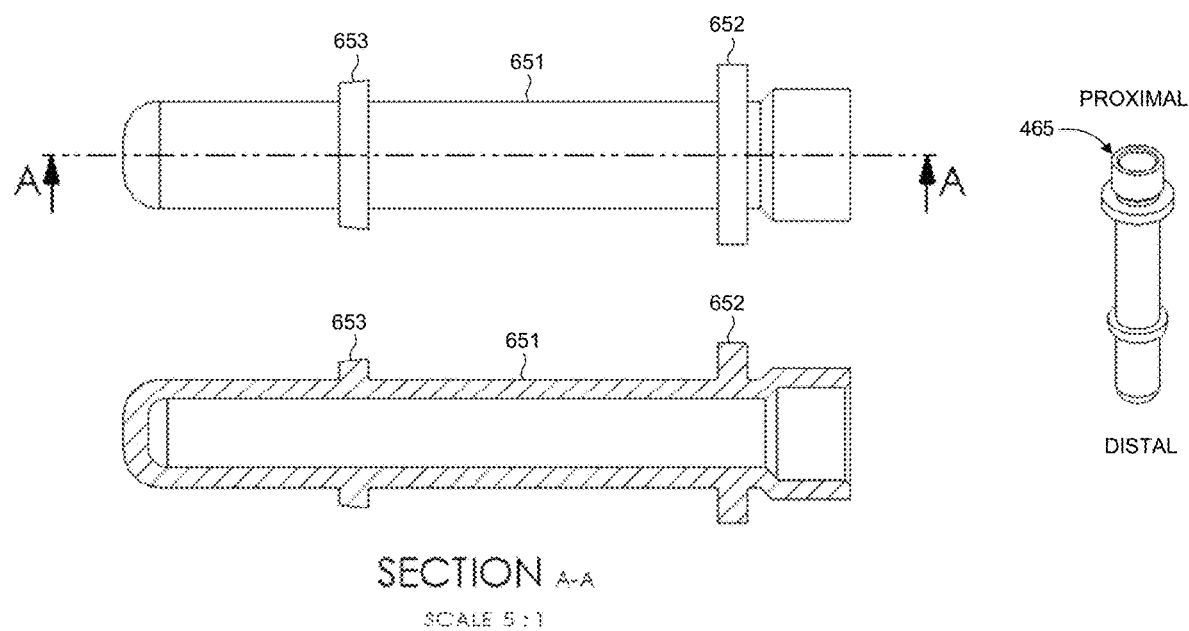
FIG. 36 is an illustration of a needle guard for a safety needle assembly, constructed and operative in accordance with a third embodiment of the present invention, the illustration including a perspective view, an orthographic side view, and a sectional view of the needle guard.

Needle guard 465 is illustrated in further detail in FIG. 36. Needle guard 465 includes a short cylindrical tube 651 which is opened at its proximal end and closed at its distal end. Needle 464 is encased within cylindrical tube 651, which overlaps the distal hollow portion 632 of syringe hub 463 at its proximal end so as to seal distal hollow portion 632. Needle guard 465 further includes a proximal ring 652 and a distal ring 653 radially encircling the outer circumferential surface of needle guard 465, where the diameter of distal ring 653 is smaller than that of proximal ring 652. Proximal ring 652 and distal ring 653 are configured to facilitate engagement of needle guard 465 and outer cap 407 as will be elaborated upon hereinbelow. It is appreciated that needle guard 465 is directed to prevent contamination or needlestick injury from an exposed needle 464, and acts as a barrier for the injectant substance in syringe chamber 462 when assembly 400 is in a storage state.

Figure 37:
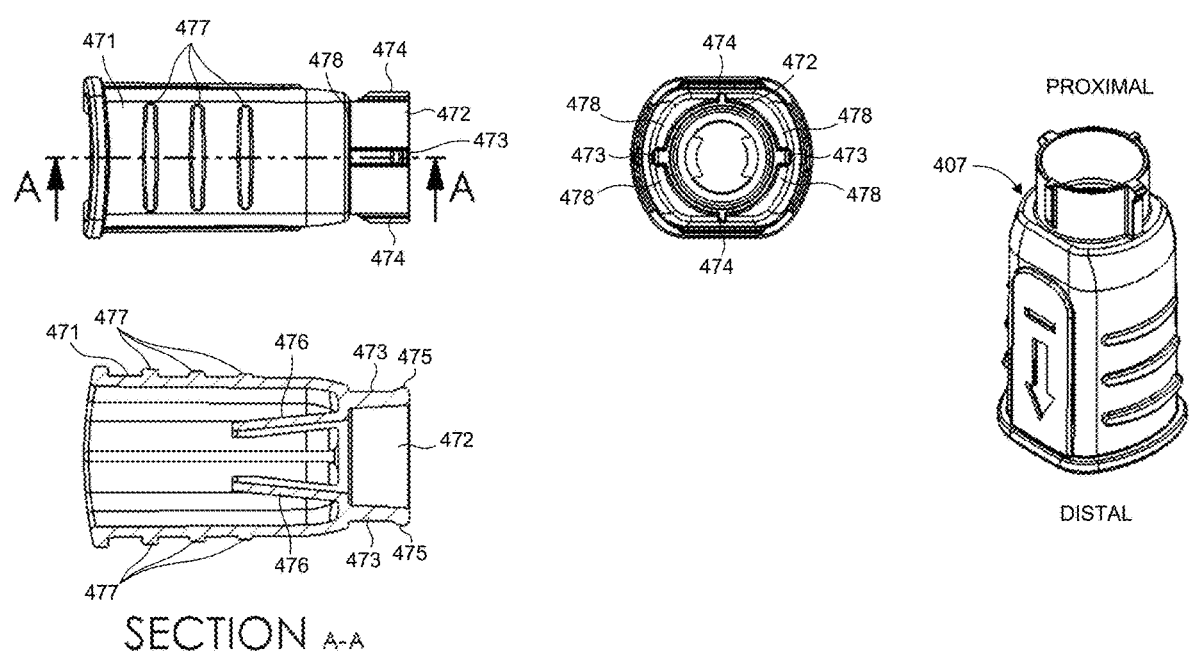
FIG. 37 is an illustration of an outer cap for a safety needle assembly, constructed and operative in accordance with a third embodiment of the present invention, the illustration including a perspective view, orthographic side and top views, and a sectional view of the outer cap.

Outer cap 407 is illustrated in FIG. 37. Outer cap 407 is positioned at the distal end of EH 401. Outer cap 407 includes a hollow cap body 471 and a hollow cap tube 472. Cap tube 472 is positioned proximally of cap body 471 and separated by a connecting wall 478, and cap tube 472 has a smaller diameter than cap body 471. Outer cap 407 includes a pair of thick ribs 473 and a pair of thin ribs 474 extending longitudinally on the outer circumferential surface of cap tube 472, such that thick ribs 473 are disposed symmetrically on opposite sides of cap tube 472, and thin ribs 474 are positioned orthogonal to thick ribs 473 and disposed symmetrically on opposite sides. A respective thick rib protrusion 475 extends radially outward from the proximal end of each thick rib 473 and is configured to engage a corresponding indentation 445 of thick slot 442 of distal EH tube 441 when assembly 400 is in a storage position to prevent detachment of outer cap 407 from EH 401. Outer cap 407 further includes two cap snaps 476 located within cap body 471. Cap snaps 476 extend distally from the inner portion of connecting wall 478 and are inclined radially inward. The outer surface of cap body 471 includes pulling grips 477 to facilitate manual pulling of outer cap 407. While certain components of outer cap 407 are described for exemplary purposes as being of a plurality, outer cap 407 may more generally be configured with any number of these respective components, such as having fewer than or more than two thick ribs 473 or thin ribs 474 or cap snaps 476. It is appreciated that one function of outer cap 407 may be to facilitate the distal pulling of needle guard 465 so as to expose needle 464 prior to deployment of syringe assembly 400. Another function of outer cap 407 may be to transfer energy shock directly to EH 401 so as to protect syringe 406 upon external impact of assembly 400, such as if assembly 400 is dropped.

Figure 38:
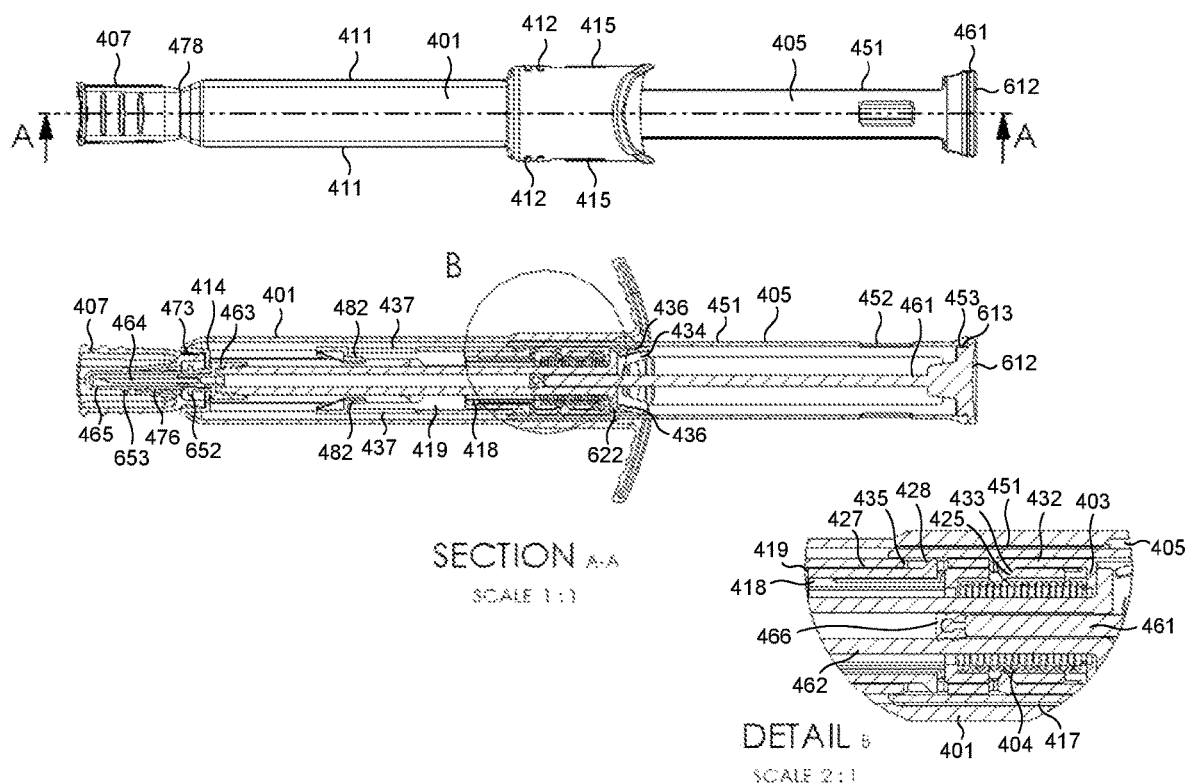
FIG. 38 is an illustration of a safety needle assembly in a storage state, constructed and operative in accordance with a third embodiment of the present invention, the illustration including a first orthographic side view, a corresponding sectional view, and a first detailed view of the safety needle assembly.
Figure 39:
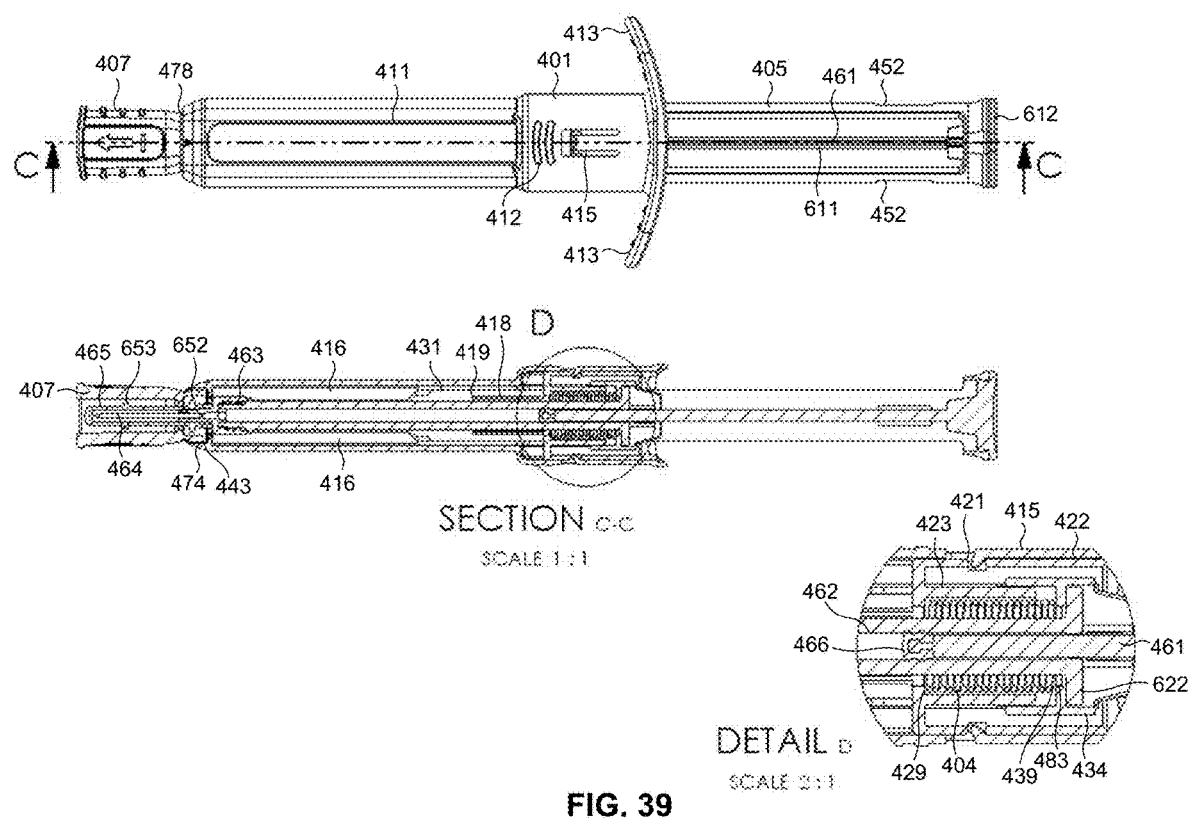
FIG. 39 is an illustration of a safety needle assembly in a storage state, constructed and operative in accordance with a third embodiment of the present invention, the illustration including a second orthographic side view, a corresponding sectional view, and a second detailed view of the safety needle assembly.

FIGS. 38 and 39 provide different views of safety needle assembly 400 in a storage state or a non-deployment state, representing the configuration of assembly 400 when not in use (i.e., before implementing an injection). IH 402 is disposed concentrically within EH 401 and is fixedly coupled to EH 401 by snaps 415 on proximal EH body portion 410 engaging with the respective connection openings 421 of IH outer tube 422. LOS 403 is also disposed concentrically within EH 401. LOS 403 is disposed between outer tube 422 and inner tube 423 of IH 402, with extending arms 431 extending past the distal end of IH 402, and with gripping snaps 432 positioned such that the inward slope 433 of each gripping snap 432 is supported by an opposing gripping slope 425 of inner tube 423. Stopping protrusions 438 of LOS 403 are aligned angularly with locking snaps 427 of IH 402. Locking teeth 428 of IH 402 are positioned within first locking windows 435 on guiding arms 431 of LOS 403. BE 404 is disposed within IH 402. BE 404 is supported at its distal end by base wall 429 of IH 402, and supported at its proximal end by flange wall 483 of LOS 403. BE 404 applies a biasing axial force that biases LOS 403 to the proximal direction, and compels gripping snaps 432 of LOS 403 to deflect radially outwards by gripping slope 425 of IH 402. However, the radial outward deflection of gripping snaps 432 is prevented by AF 405, as described further hereinbelow.

AF 405 is positioned between LOS 403 and outer tube 422 of IH 402. End member 454 of AF 405 is coupled to finger rest 612 of syringe 406, by groove 452 on inner surface of end member 454 engaging with a cylindrical outward facing protrusion 613 on finger rest 612. Guiding arms 451 of AF 405 are guided by connecting ribs 424 of IH 402, and are positioned between gripping snaps 432 of LOS 403 and guiding ribs 426 on inner surface of outer tube 422 of IH 402. Guiding arms 451 are also supported by support ribs 417 protruding radially from the inner surface proximal end of proximal EH body portion 410, preventing the radial deflection of gripping snaps 432, which in turn prevents LOS 403 from being displaced proximally by the biasing force applied by BE 404.

Syringe 406 is disposed concentrically within inner tube 423 of IH 402. Barrel flange 622 of syringe chamber 462 is positioned between flange wall 483 and holding snaps 436 of LOS 403, which prevents axial movement of syringe 406 relative to LOS 403. Syringe needle 464 extends at least partially through distal opening 414 and is encased by needle guard 465. Outer cap 470 covers needle guard 465 distally of EH 401. Cap tube 472 of outer cap 470 is positioned within EH distal tube 441 of EH 401, and cap body 471 is positioned distally of EH distal opening 414, such that connecting wall 478 effectively prevents outer cap 407 from being fully enveloped within EH 401. Thick ribs 473 and thin ribs 474 on cap tube 472 are correspondingly positioned within respective thick slots 442 and thin slots 443 on EH distal tube 441, thereby rotationally orienting outer cap 407 in a specific manner in relation to EH 401. The greater thickness of thick ribs 473 relative to thin ribs 474 prevents outer cap 407 from engaging with EH 401 differently from the intended manner, such as in a perpendicular orientation, since thick ribs 473 are physically incapable of embedding within thin slots 443 of EH distal tube 441. Furthermore, thick rib protrusions 475 are embedded within corresponding thick slot indentations 445 of EH distal tube 441, so as to prevent outer cap 407 from disengaging from EH 401 (without applying a sufficient distal axial pulling force on outer cap 407). Needle guard 465 is positioned distally of EH 401 within outer cap 407, such that the distal end of outer cap 407 is distal of the distal end of needle guard 465. The distal end of cap snaps 476 are positioned proximal of distal ring 653 of needle guard 465, and the inner portion of connecting wall 478 is positioned distal of proximal ring 652 of needle guard, thus coupling outer cap 407 with needle guard 465. When outer cap 407 is pulled distally so as to expose needle 464 prior to insertion, the distal end of cap snaps 476 engages with distal ring 653 so as to distally pull needle guard 465 along with outer cap 407. After their removal from EH 401 and syringe 406, needle guard 465 and outer cap 407 remain integrally coupled to one another, as cap snaps 476 are fixedly embedded between proximal ring 652 and distal ring 653.

To deploy assembly 400 for performing an injection, a user (e.g., a medical clinician) holds assembly 400, such as via grip 412. The user removes needle guard 465 by pulling outer cap 407 in a distal direction, such as via pulling grips 477. The pulling of outer cap 407 compels thick rib protrusions 475 to disengage from respective thick slot indentations 445 of EH distal tube 441, and cap snaps 476 to engage with distal ring 653 of needle guard 465, thereby pulling needle guard 465 distally along with outer cap 407 so as to expose needle 464. As needle guard 465 is pulled, the inner surface of hub tube 651 slides off the outer surface of distal hub body portion 632 of syringe hub 463. Following their removal, needle guard 465 remains encased within outer cap 407 by cap snaps 476 being fixedly embedded between proximal ring 652 and distal ring 653 of needle guard 465.

Figure 40:
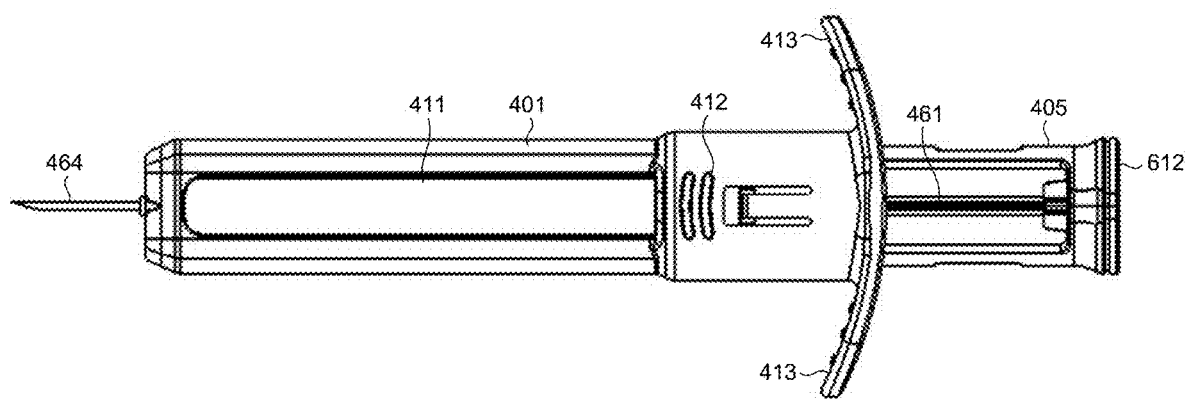
FIG. 40 is an orthographic side view illustration of a safety needle assembly during an injection stage, operative in accordance with a third embodiment of the present invention.

The user inserts the exposed distal end of needle 464 into an injection site (e.g., a body region of a patient to be injected), such as by holding EH 401 at grip 412 and pushing needle 464 into the injection site. After needle 464 has been inserted, the user presses syringe finger rest 612 distally while applying a counterforce against EH flange 413, compelling axial movement of plunger rod 461 in the distal direction together with AF 405. The distal advancement of plunger rod 461 mutually advances plunger stopper 466 within syringe chamber 462, which propels the injectant substance distally within chamber 462 to pass through the distal aperture of needle 464 and enter the injection site. The progress of plunger rod 461 and plunger stopper 466 along chamber 462 and the passage of the injectant substance can be viewed through windows 411 of EH 401. FIG. 40 illustrates safety needle assembly 400 during an injection stage.

Figure 41:
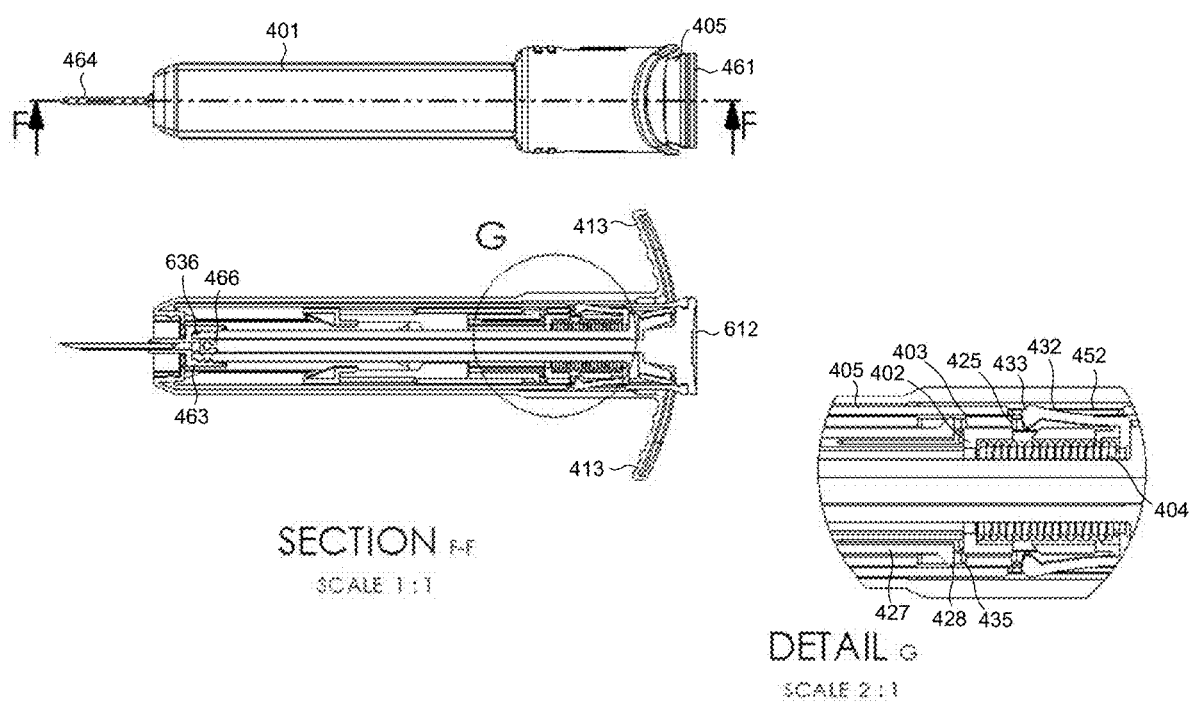
FIG. 41 is an illustration of a safety needle assembly during a syringe activation stage, operative in accordance with a third embodiment of the present invention, the illustration including an orthographic side view, a corresponding sectional view, and a detailed view of the safety needle assembly.

Toward the end of the injection, when plunger stopper 466 has reached a position adjacent to internal sleeve 363 of syringe hub 463 and the injectant substance is nearly completely administered, activation openings 452 of guiding arms 451 of AF 405 align with gripping snaps 432 of LOS 403. This allows gripping snaps 432 to deflect radially outwards through the respective activation openings 452 (since they are no longer prevented from such deflection by guiding arms 451), compelling an axial displacement of LOS 403 to the proximal direction (due to the biasing force applied by BE 404). Syringe 406 and LOS 403 are held in place by the clamping force applied by the user pressing against finger rest 612 and against EH flange 413, allowing the user to complete the injection. FIG. 41 illustrates safety needle assembly 400 during a syringe activation or end of injection, showing the respective alignments of LOS 403, AF 405 and syringe 406 at this stage.

Safety needle assembly 400 provides a smooth and substantially constant opposing resistive force during the advancement of syringe plunger rod 461, without an abrupt force increase needed to activate the safety retraction mechanism as in conventional (partially automated) safety syringes. The smooth and substantially constant resistance compels the user to fully depress syringe plunger rod 461 (by continuing to press against finger rest 612) without prematurely terminating the distal advancement of plunger rod 461 along syringe chamber 462 before the injection process has been fully carried out and the safety mechanism has been activated. Reference is made again to FIGS. 28, 29 and 30 and the relevant description provided hereinabove.

After the injection process is completed and the injectant substance is fully administered, the user releases the distal force applied to syringe plunger rod 461 by reducing the clamping force between finger rest 612 and EH flange 413. This gradually reduces the axial force applied to syringe 406 and LOS 403, allowing the biasing force of BE 404 to move LOS 403 axially to the proximal direction. As LOS 403 moves proximally, gripping snaps 432 are deflected radially outward through activation openings 452 (due to the interaction between inward slope 433 of LOS 403 and gripping slope 425 of IH 402), until gripping snaps 432 pass the proximal end of inner tube 423, allowing gripping snaps 432 to return to their relaxed (non-deflected) position. At a certain proximal advancement of LOS 403, locking snaps 427 of IH 402 engage first locking windows 435 of LOS 403 and deflect radially inwards, allowing for further advancement of LOS 403.

Figure 42:
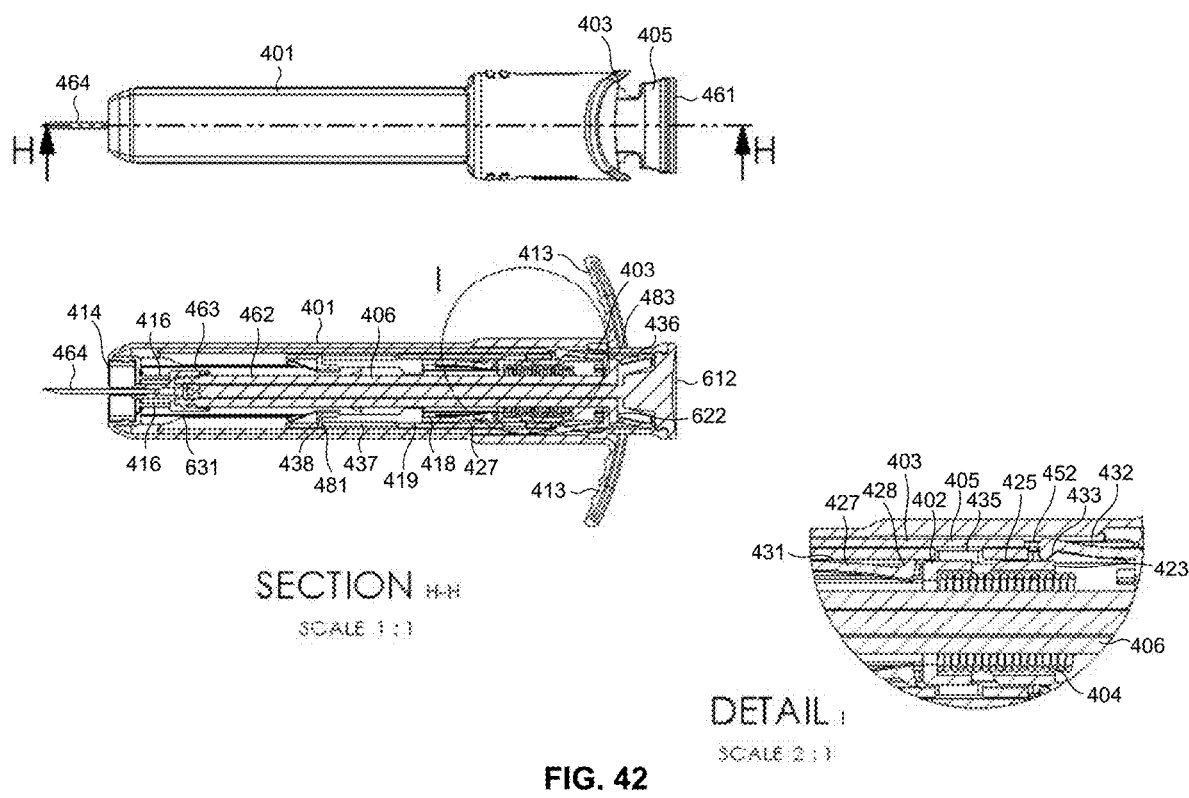
FIG. 42 is an illustration of a safety needle assembly during a syringe retraction stage, operative in accordance with a third embodiment of the present invention, the illustration including an orthographic side view, a corresponding sectional view, and a detailed view of the safety needle assembly.

The proximal motion of LOS 403 continues until proximally facing ridges 481 of stopping protrusions 438 of LOS 403 engages distal end 419 of IH 402. At this point, locking snaps 427 of IH 402 are aligned such that locking teeth 428 are positioned within second locking windows 437 of LOS 403 and no longer supported by guiding arms 431, allowing locking snaps 427 to return to their relaxed (non-deflected) position, restricting further LOS 403 movement. The proximal axial movement of LOS 403 is accompanied by the mutual proximal axial movement of syringe 406, due to the engagement of barrel flange 622 with flange wall 483, which in turn causes syringe hub 463 and syringe needle 464 to retract (proximally) into the assembly housing (EH 401 and/or IH 402) through opening 414. As syringe hub 463 retracts, proximal hub body portion 631 is guided by distal ribs 416 of distal EH body portion 420. At the end of the syringe retraction, needle 464 is completely positioned within the assembly housing, such that the distal end of needle 464 is proximal of the distal end of EH 401 and/or IH 402. FIG. 42 illustrates safety needle assembly 400 during a syringe retraction stage.

Figure 43:
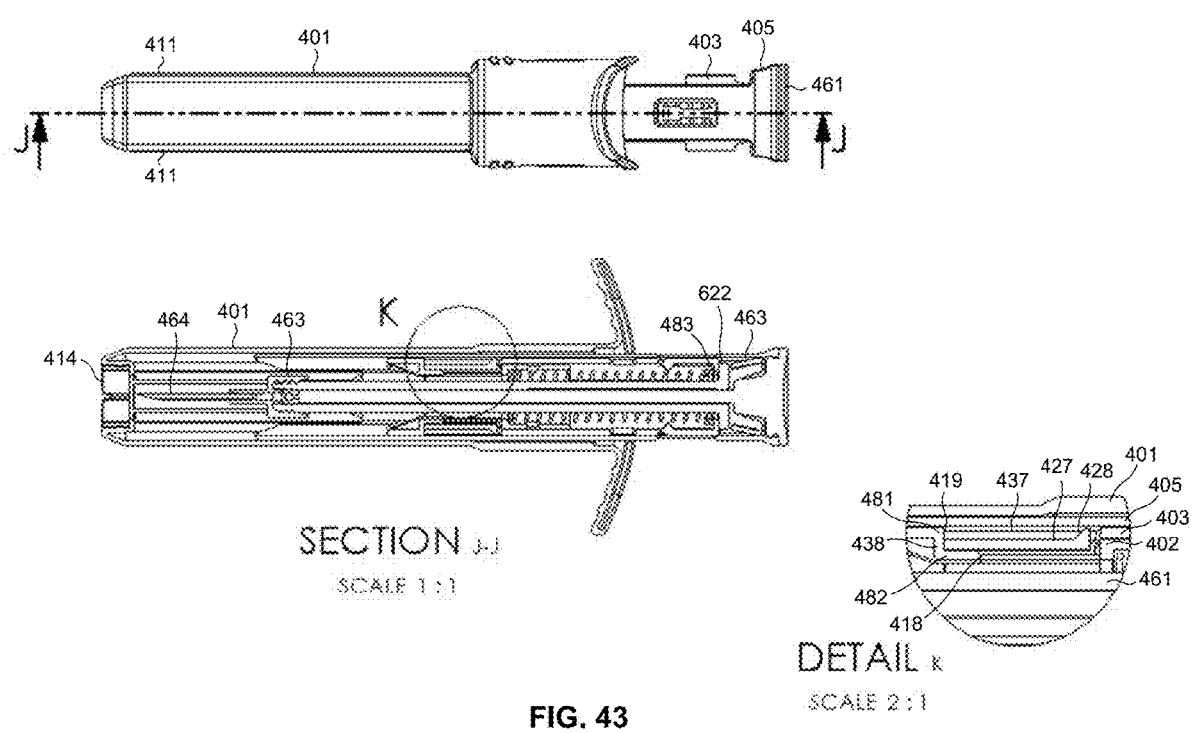
FIG. 43 is an illustration of a safety needle assembly in a discard state, constructed and operative in accordance with a third embodiment of the present invention, the illustration including an orthographic side view, a corresponding sectional view, and a detailed view of the safety needle assembly.

When syringe 406 is fully retracted, the engagement of the proximal end of locking teeth 428 with the proximal end of second locking windows 437 prevents LOS 403 and syringe 406 from moving distally and re-exposing needle 464 through distal opening 414. The engagement of IH distal end 419 with proximally facing ridges 481 of stopping protrusions 438 prevents LOS 403 and syringe from moving proximally and exposing needle 464 through the proximal end of EH 401. Syringe 406 is prevented from disengaging from LOS 403 due to the interaction between barrel flange 622 and flange wall 483 from the distal side and holding snaps 436 from the proximal side. The engagement of axially parallel walls 482 of stopping protrusions 438 with the inner surface of distally extending portion 418 of inner tube 423 of IH 402 prevents guiding arms 431 from being deflected radially outwards. Syringe needle 464 is now locked in its entirety within EH 401 as can be viewed through EH windows 411. This places assembly 400 in a discard state, allowing for safe disposal of needle 464 and assembly 400. FIG. 43 illustrates safety needle assembly 400 during a discard state.

It will be appreciated that the disclosed safety needle assemblies (100, 200, 400) provides for automatic retraction of the needle (165, 265, 464) after the injection has been completed, while avoiding premature termination of the injection process, and avoiding non-activation of the safety retraction mechanism, while still providing the user with an indication of how and when the injection has been properly carried out.

While certain embodiments of the disclosed subject matter have been described, so as to enable one of skill in the art to practice the present invention, the preceding description is intended to be exemplary only. It should not be used to limit the scope of the disclosed subject matter, which should be determined by reference to the following claims.

The invention claimed is:

1. An automatically retracting safety needle assembly configured to receive a syringe, the assembly having a distal end and a proximal end, the assembly comprising:
    a housing, comprising an internal housing (IH), having a base wall situated at the distal end of the IH;
    a moving sleeve (MOS), at least partially disposed within the IH, the MOS comprising a flange wall, the MOS being axially movable;
    a biasing element (BE), disposed within the IH, the BE being supported between said base wall and said flange wall, the BE is configured to bias the MOS to the proximal direction;
    said syringe, disposed in and movable axially within the IH, and coupled to the MOS, said syringe is configured to receive a plunger rod thereinto;
    an activation fork (AF), partially disposed within the IH, the AF comprising at least one guiding arm, the at least one guiding arm being coupled with the IH and the MOS so as to prevent proximal motion of the MOS when the assembly is in a non-deployment state; and
    a retraction mechanism, configured to automatically retract the syringe upon completion of injection,
    wherein the assembly is configured to be deployed for injection by advancing the plunger rod and the AF axially in the distal direction with respect to the IH, the plunger rod advancing until the at least one guiding arm of the AF allows proximal movement of the MOS, thereby causing retraction of said syringe, wherein the distal advancement of the plunger rod is substantially constant without an abrupt increase in resistive force to overcome for activating the retraction mechanism, allowing for safe disposal of the assembly.

2. The automatically retracting safety needle assembly of claim 1,
    wherein the housing further comprises an external housing, wherein the internal housing is fixedly coupled to the external housing.

3. The automatically retracting safety needle assembly of claim 1, wherein the movable sleeve (MOS) is a rotating sleeve (ROS) comprising:
    at least one extending arm, extending distally from the flange wall;
    a guiding slot on the extending arm, the guiding slot comprising: a helical-shaped slot portion at the proximal edge of the guiding slot; an elongated straight slot portion distal of the helical-shaped slot portion; and an extension slot portion extending from the straight slot portion;
    at least one notched flange, protruding radially outwards from the flange wall, the notched flange comprising a wide notch; and
    at least one holding snap, projecting proximally from the edge of the flange wall, wherein the IH further comprises at least one direction protrusion positioned inside the guiding slot, and wherein the at least one guiding arm of the AF is coupled with the IH and the ROS by insertion into guiding ribs of the IH, and by insertion into the wide notch of the notched flange of the ROS.

4. The automatically retracting safety needle assembly of claim 3, wherein the syringe is coupled to the ROS via the holding snap of the ROS, preventing axial motion of the syringe flange relative to the ROS when the assembly is in the non-deployment state.

5. The automatically retracting safety needle assembly of claim 3, wherein the flange wall of the ROS comprises at least one arc-shaped opening, and wherein the IH further comprises at least one orienting protrusion, configured to prevent rotation of the syringe, wherein the orienting protrusion is positioned through the arc-shaped opening of the flange wall of the ROS.

6. The automatically retracting safety needle assembly of claim 3, wherein the plunger advances until the at least one guiding arm of the AF passes through the wide notch of the notched flange of the ROS, allowing for rotation of the ROS relative to the AF, and allowing the biasing force of the BE to move the ROS in the proximal direction, resulting in the directing protrusion urging rotation of the ROS, until the directing protrusion is guided from the helical slot into the straight slot of the guiding slot of the ROS, allowing for further axial movement of the ROS in the proximal direction.

7. The automatically retracting safety needle assembly of claim 1, wherein the movable sleeve (MOS) is a locking sleeve (LOS) comprising:
- at least one extending arm, extending distally from the flange wall;
- a gripping snap, disposed on the extending arm, the gripping snap comprising an extending protrusion with a radially facing slope;
- at least one holding snap, projecting proximally from the edge of the flange wall,
- wherein the AF further comprises an activation opening, disposed on the at least one guiding arm, and
- wherein the at least one guiding arm of the AF is positioned between the gripping snap of the LOS and the IH, such that the at least one guiding arm prevents the gripping snap from deflecting radially, and preventing proximal movement of the LOS, when the assembly is in the non-deployment position.

8. The automatically retracting safety needle assembly of claim 7, wherein the LOS further comprises:
- a locking snap, disposed on the extending arm, the locking snap comprising an extending protrusion with a deflecting slope at the distal end thereof; and
- at least one LOS stopping protrusion, extending distally from the flange wall,
- wherein the AF further comprises a locking opening, disposed on the at least one guiding arm of the AF, and
- wherein the IH further comprises at least one IH stopping protrusion, extending radially inwardly.

9. The automatically retracting safety needle assembly of claim 7, wherein the plunger rod is advanced until the activation opening of the at least one guiding arm of the AF aligns with the gripping snap of the LOS, causing the gripping snap to deflect radially through the activation opening, allowing for proximal movement of the LOS due to the biasing force of the BE, with reciprocal axial movement of the syringe so as to proximally retract the syringe into the housing, until the gripping snap passes the proximal end of the IH and returns to a non-deflected position.

10. The automatically retracting safety needle assembly of claim 7, wherein the LOS further comprises:
- a first locking window, disposed on the extending arm, distally of the gripping snap;
- a second locking window, disposed on the extending arm, distally of the first locking window; and
- at least one LOS stopping protrusion, disposed at the distal end of the extending arm,
- wherein the IH further comprises at least one IH locking snap, disposed on a distally extending portion of the IH, the IH locking snap comprising a locking tooth at a proximal end thereof,
- wherein the LOS stopping protrusion is aligned angularly with the IH locking snap, and wherein the locking tooth of the IH locking snap is positioned within the first locking window, when the assembly is in the non-deployment position.

11. The automatically retracting safety needle assembly of claim 10, wherein during proximal movement of the LOS due to the biasing force of the BE, with reciprocal axial movement of the syringe so as to proximally retract the syringe into the housing, the stopping protrusion of LOS engages the distal end of the IH, preventing further proximal movement of the LOS, and the locking snap of the IH is aligned such that the locking tooth is positioned within the second locking window of the LOS, causing the locking snap to return to a non-deflected position, and the proximal end of the locking tooth engages the proximal end of the second locking window, preventing further distal movement of the LOS and the syringe.

12. A method for retracting a syringe received into an automatically retracting safety needle assembly, the method comprising:
- providing said automatically retracting safety needle assembly, the assembly having a distal end and a proximal end, the assembly comprising:
  - a housing, comprising an internal housing (IH), having a base wall situated at the distal end of the IH;
  - a moving sleeve (MOS), at least partially disposed within the IH, the MOS comprising a flange wall, the MOS being axially movable;
  - a biasing element (BE), disposed within the IH, the BE being supported between said base wall and said flange wall, the BE is configured to bias the MOS to the proximal direction;
  - said syringe, disposed in and movable axially within the IH, and coupled to the MOS, said syringe is configured to receive a plunger rod thereinto;
  - an activation fork (AF), partially disposed within the IH, the AF comprising at least one guiding arm, the at least one guiding arm being coupled with the IH and the MOS so as to prevent proximal motion of the MOS when the assembly is in a non-deployment state; and
  - a retraction mechanism, configured to automatically retract the syringe upon completion of injection, inserting a needle attached to said syringe into an injection site;
- advancing the plunger rod and the AF axially in the distal direction with respect to the IH, the plunger rod advancing until the at least one guiding arm of the AF allows proximal movement of the MOS, thereby causing retraction of said syringe, wherein the distal advancement of the plunger rod is substantially constant without an abrupt increase in resistive force to overcome for activating the retraction mechanism, allowing for safe disposal of the assembly.

13. The method of claim 12, wherein the movable sleeve (MOS) is a rotating sleeve (ROS) comprising:
- at least one extending arm, extending distally from the flange wall;
- a guiding slot on said extending arm, the guiding slot comprising: a helical-shaped slot portion at the proximal edge of the guiding slot; an elongated straight slot portion distal of the helical-shaped slot portion; and an extension slot portion extending from the straight slot portion;
- at least one notched flange, protruding radially outwards from the flange wall, the notched flange comprising a wide notch; and
- at least one holding snap, projecting proximally from the edge of the flange wall, wherein the IH further comprises at least one direction protrusion positioned inside the guiding slot, and
- wherein the at least one guiding arm of the AF is coupled with the IH and the ROS by insertion into guiding ribs of the IH, and by insertion into the wide notch of the notched flange of the ROS.

14. The method of claim 13, further comprising the procedure of releasing the pressing force upon completion of the injection, to allow the biasing force of the BE to move the ROS in the proximal direction, resulting in the directing protrusion of the IH urging the rotation of the ROS, until the directing protrusion is guided from the helical slot into the straight slot of the guiding slot of the ROS, allowing for further axial movement of the ROS in the proximal direction.

15. The method of claim 12, wherein the movable sleeve (MOS) is a locking sleeve (LOS) comprising:
- at least one extending arm, extending distally from the flange wall;
- a gripping snap, disposed on the extending arm, the gripping snap comprising an extending protrusion with a radially facing slope at the distal end thereof;
- at least one holding snap, projecting proximally from the edge of the flange wall, wherein the AF further comprises an activation opening, disposed on the guiding arm, and
- wherein the the at least one guiding arm of the AF is positioned between the gripping snap of the LOS and the IH, such that the at least one guiding arm prevents the gripping snap from deflecting radially, and preventing proximal movement of the LOS, when the assembly is in the non-deployment position.

16. The method of claim 15, wherein the LOS further comprises:
- a locking snap, disposed on the extending arm, the locking snap comprising an extending protrusion with a deflecting slope at the distal end thereof; and
- at least one LOS stopping protrusion, extending distally from the flange wall,
- wherein the AF further comprises a locking opening, disposed on the at least one guiding arm of the AF, and
- wherein the IH further comprises at least one IH stopping protrusion, extending radially inwardly.

17. The method of claim 15, further comprising the procedure of distally advancing the plunger rod and the AF until the activation opening of the at least one guiding arm of the AF aligns with the gripping snap of the LOS, causing the gripping snap to deflect radially through the activation opening, allowing for proximal movement of the LOS due to the biasing force of the BE, with reciprocal axial movement of the syringe so as to proximally retract the syringe into the housing, until the gripping snap passes the proximal end of the IH and returns to a non-deflected position.

18. The method of claim 15, further comprising the procedure of distally advancing the plunger rod and the AF until the locking opening of the at least one guiding arm of the AF aligns with the locking snap of the LOS, causing the locking snap to deflect radially through the locking opening, during proximal movement of the LOS due to the biasing force of the BE, with reciprocal axial movement of the syringe so as to proximally retract the syringe into the housing, until the locking snap passes the proximal end of the IH and returns to a non-deflected position, and the LOS stopping protrusion engages the IH stopping protrusion preventing further proximal movement of the LOS, and the locking snap restricts further distal movement of the LOS.

19. The method of claim 15, wherein the LOS further comprises:
- a first locking window, disposed on the extending arm, distally of the gripping snap;
- a second locking window, disposed on the extending arm, distally of the first locking window; and
- at least one LOS stopping protrusion, disposed at the distal end of the extending arm,
- and wherein the IH further comprises at least one IH locking snap, disposed on a distally extending portion of the IH, the IH locking snap comprising a locking tooth at a proximal end thereof,
- wherein the LOS stopping protrusion is aligned angularly with the IH locking snap, and wherein the locking tooth of the IH locking snap is positioned within the first locking window, when the assembly is in the non-deployment position.

20. The method of claim 19, further comprising the procedure of proximally retracting the syringe into the housing, during proximal movement of the LOS due to the biasing force of the BE, with reciprocal axial movement of the syringe such that the stopping protrusion of the LOS engages the distal end of the IH, preventing further proximal movement of the LOS, and aligning the locking snap of the IH such that the locking tooth is positioned within the second locking window of the LOS, causing the locking snap to return to a non-deflected position, and the proximal end of the locking tooth engages the proximal end of the second locking window, preventing further distal movement of the LOS and the syringe.

* * * * *